United States Patent
Cheng et al.

(10) Patent No.: US 12,055,536 B2
(45) Date of Patent: *Aug. 6, 2024

(54) DEVICE FOR DETECTION OF CELLULAR STRESS

(71) Applicants: Trustees of Boston University, Boston, MA (US); Northwestern University, Evanston, IL (US)

(72) Inventors: Ji-Xin Cheng, Newton, MA (US); Junjie Li, Arlington, MA (US); Yuying Tan, Allston, MA (US); Daniela Matei, Chicago, IL (US); Guangyuan Zhao, Chicago, IL (US)

(73) Assignees: Trustees of Boston University, Boston, MA (US); Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/317,637

(22) Filed: May 15, 2023

(65) Prior Publication Data
US 2023/0384288 A1 Nov. 30, 2023

Related U.S. Application Data

(63) Continuation of application No. 17/839,080, filed on Jun. 13, 2022, now Pat. No. 11,692,996.
(Continued)

(51) Int. Cl.
*G01J 3/44* (2006.01)
*G01N 27/30* (2006.01)
(Continued)

(52) U.S. Cl.
CPC ........... *G01N 33/492* (2013.01); *G01N 27/30* (2013.01); *G01N 27/416* (2013.01); *G01N 33/48735* (2013.01); *G01Q 60/60* (2013.01); *G16H 20/10* (2018.01); *G16H 50/30* (2018.01); *G01N 21/65* (2013.01); *G01N 2800/52* (2013.01)

(58) Field of Classification Search
CPC .... G01N 33/492; G01N 27/30; G01N 27/416; G01N 33/48735; G01N 21/65; G01N 2800/52; G01Q 60/60; G16H 20/10; G16H 50/30
See application file for complete search history.

(56) References Cited

U.S. PATENT DOCUMENTS

| | | | |
|---|---|---|---|
| 2013/0040292 A1* | 2/2013 | Fernandez Lopez | G01N 33/54326 427/214 |
| 2021/0055302 A1 | 2/2021 | Rao | |
| 2022/0133767 A1 | 5/2022 | Slack et al. | |

OTHER PUBLICATIONS

Schug, Zachary T. et al., "Acetyl-CoA Synthetase 2 Promotes Acetate Utilization and Maintains Cancer Cell Growth under Metabolic Stress," Cancer Cell 27, pp. 57-71 (2015).
(Continued)

*Primary Examiner* — Abdullahi Nur
(74) *Attorney, Agent, or Firm* — Cesari and McKenna, LLP; Steven M. Mills

(57) ABSTRACT

Disclosed is an assay for determining resistance in a target cell or tissue to a therapy associated with cellular stress using chemical microscopy and high-throughput single cell analysis to determine functional metabolic alteration, including determining metabolic reprogramming in a target cell or tissue to a therapy associated with cellular stress, and methods of using the assays.

20 Claims, 66 Drawing Sheets
Specification includes a Sequence Listing.

Related U.S. Application Data

(60) Provisional application No. 63/210,286, filed on Jun. 14, 2021.

(51) Int. Cl.

| | | |
|---|---|---|
| G01N 27/416 | (2006.01) | |
| G01N 33/487 | (2006.01) | |
| G01N 33/49 | (2006.01) | |
| G01Q 60/60 | (2010.01) | |
| G16H 20/10 | (2018.01) | |
| G16H 50/30 | (2018.01) | |
| G01N 21/65 | (2006.01) | |

(56) References Cited

OTHER PUBLICATIONS

Shen, D.W. et al., "Cisplatin resistance: a cellular self-defense mechanism resulting from multiple epigenetic and genetic changes," Pharmacol Rev 64, pp. 706-721 (2012).
Snaebjornsson, M.T. et al., "Greasing the Wheels of the Cancer Machine: The Role of Lipid Metabolism in Cancer," Cell Metab 31, pp. 62-76 (2020).
Sousa, C.M. et al., "Pancreatic stellate cells support tumour metabolism through autophagic alanine secretion," Nature 536, pp. 479-483 (2016).
Su, X. & Abumrad, N.A., "Cellular fatty acid uptake: a pathway under construction," Trends Endocrinol. Metab. 20, pp. 72-77 (2009).
Tadros, S. et al., "De Novo Lipid Synthesis Facilitates Gemcitabine Resistance through Endoplasmic Reticulum Stress in Pancreatic Cancer," Cancer Res. 77, pp. 5503-5517 (2017).
Van De Vaart, P.J. et al., "Intraperitoneal cisplatin with regional hyperthermia in advanced ovarian cancer: pharmacokinetics and cisplatin-DNA adduct formation in patients and ovarian cancer cell lines," Eur. J. Cancer 34, pp. 148-154 (1998).
Van Der Vusse, G.J. et al., "Critical steps in cellular fatty acid uptake and utilization," Molecular and Cellular Biochemistry 239, pp. 9-15 (2002).
Wagner, W. et al., "L- and D-lactate enhance DNA repair and modulate the resistance of cervical carcinoma cells to anticancer drugs via histone deacetylase inhibition and hydroxycarboxylic acid receptor 1 activation," Cell Commun Signal 13:36, DOI 10.1186/s12964-015-0114-x (2015).
Wang, D. & Lippard, S.J., "Cellular processing of platinum anticancer drugs," Nat. Rev. Drug Discov. 4, pp. 307-320 (2005).
Wang, Y. et al., "Frizzled-7 identifies platinum-tolerant ovarian cancer cells susceptible to ferroptosis," Cancer Res. 81, pp. 384-399 (2021).
Ward, Patrick S. & Thompson, Craig B., "Metabolic Reprogramming: A Cancer Hallmark Even Warburg Did Not Anticipate," Cancer Cell 21, pp. 297-308 (2012).
Yu, W. et al., "Cisplatin generates oxidative stress which is accompanied by rapid shifts in central carbon metabolism," Sci. Rep. 8:4306, DOI: 10.1038/s41598-018-22640-y (2018).
Yue, S. et al., "Cholesteryl ester accumulation induced by PTEN loss and PI3K/AKT activation underlies human prostate cancer aggressiveness," Cell Metabolism vol. 19, pp. 393-406 (2014).
Zaugg, K. et al., "Carnitine palmitoyltransferase 1C promotes cell survival and tumor growth under conditions of metabolic stress," Genes & Development 25, pp. 1041-1051 (2011).
Zhang, C., et al., "Coherent Raman scattering microscopy in biology and medicine," Annu. Rev. Biomed. Eng. 17, pp. 415-445 (2015).
Zhang, L. et al., "Spectral tracing of deuterium for imaging glucose metabolism," Nat. Biomed. Eng. 3, pp. 402-413 (2019).
Zhao, Y. et al., "Targeting cellular metabolism to improve cancer therapeutics," Cell Death Dis 4:e532, DOI:10.1038/cddis.2013.60 (2013).

Chen et al., "Metabolic Reprogramming of Chemoresistant Cancer Cells and the Potential Significance of Metabolic Regulation in the Reversal of Cancer Chemoresistance," Metabolites, vol. 10, No. 7, Jul. 2020, pp. 1-15.
Desbats et al., "Metabolic Plasticity in Chemotherapy Resistance," Frontiers in Oncology, vol. 10, Jan. 2020, pp. 1-20.
Du et al., "Raman-guided subcellular pharmaco-metabolomics for metastatic melanoma cells," Nature Communications, vol. 11, No. 1, Dec. 2020, pp. 1-16.
Huang et al., "Multiplex stimulated Raman scattering imaging cytometry reveals cancer metabolic signatures in a spatially, temporally, and spectrally resolved manner," Arxiv.org, Cornell University Library, Dec. 2019, pp. 1-42.
Li et al., "Reprogramming of glucose, fatty acid and amino acid metabolism for cancer progression," Cellular and Molecular Life Sciences, vol. 73, No. 2, Oct. 2015, pp. 377-392.
Tan et al., "Metabolic reprogramming from glycolysis to fatty acid uptake and beta-oxidation in platinum-resistant cancer cells," Nature Communications, vol. 13, No. 1, Aug. 2022, pp. 1-16.
Zhao et al., "Ovarian Cancer—Why Lipids Matter," Cancers, vol. 11, No. 12, Nov. 2019, pp. 1-16.
International Search Report of International Patent Application No. PCT/US2022/033303 mailed on Oct. 27, 2022.
Belotte, J. et al., "The role of oxidative stress in the development of cisplatin resistance in epithelial ovarian cancer," Reprod. Sci. 21, pp. 503-508 (2014).
Bergers, G. & Fendt, S.-M., "The metabolism of cancer cells during metastasis," Nat Rev Cancer 21, pp. 162-180 (2021).
Cao, Y., "Adipocyte and lipid metabolism in cancer drug resistance," J. Clin. Invest. 129(8), pp. 3006-3017 (2019).
Carpenter, A.E. et al., "CellProfiler: image analysis software for identifying and quantifying cell phenotypes," Genome Biology 7:R100, DOI:10.1186/GB-2006-7-10-r100 (2006).
Chae, Y.C. & Kim, J.H., "Cancer stem cell metabolism: target for cancer therapy," BMB Reports 51, pp. 319-326 (2018).
Cheng, J.X. & Xie, X.S., "Vibrational spectroscopic imaging of living systems: An emerging platform for biology and medicine," Science vol. 350, iss. 6264, DOI: 10.1126/science.aaa8870 (2015).
Condello, S. et al., "[beta]-Catenin-regulated ALDH1A1 is a target in ovarian cancer spheroids,". Oncogene 34, pp. 2297-2308 (2015).
Condello, S. et al., "Tissue tranglutaminase regulates interactions between ovarian cancer stem cells and the tumor niche," Cancer Res., 78, pp. 2990-3001 (2018).
Cotte, A.K. et al., "Lysophosphatidylcholine acyltransferase 2-mediated lipid droplet production supports colorectal cancer chemoresistance," Nature Communications 9:322, DOI 10.1038/s41467-017-02732-5 (2018).
Currie, E. et al., "Cellular fatty acid metabolism and cancer," Cell Metab. 18, pp. 153-161 (2013).
Doege, H. & Stahl, A., "Protein-mediated fatty acid uptake: novel insights from in vivo models," Physiology (Bethesda) 21, pp. 259-268 (2006).
Dong, R. et al., "Histologic and molecular analysis of patient derived xenografts of high-grade serous ovarian carcinoma," J. Hematol. Oncol. 9:92, DOI: 10.1186/s13045-016-0318-6 (2016).
Du, J. et al., "Raman-guided subcellular pharmaco-metabolomics for metastatic melanoma cells," Nat. Commun. 11:4830, DOI: 10.2038/s41467-020-18376-x (2020).
Eckert, M.A., et al., "The Effects of Chemotherapeutics on the Ovarian Cancer Microenvironment," Cancers (Basel) 13, DOI: 10.3390/cancers13133136 (2021).
Faubert, B. et al., "Metabolic reprogramming and cancer progression," Science 368, eaaw5473 (2020).
Fu, D. & Xie, X.S., "Reliable cell segmentation based on spectral phasor analysis of hyperspectral stimulated Raman scattering imaging data," Anal Chem 86, pp. 4115-4119 (2014).
Furuhashi, M. et al., "Treatment of diabetes and atherosclerosis by inhibiting fatty-acid-binding protein aP2," Nature 447, pp. 959-965 (2007).
Galluzzi, L. et al., "Molecular mechanisms of cisplatin resistance," Oncogene 31, pp. 1869-1883 (2012).

(56) References Cited

OTHER PUBLICATIONS

Ghanbari Movahed, Z., et al., "Cancer cells change their glucose metabolism to overcome increased ROS: One step from cancer cell to cancer stem cell?," Biomed. Pharmacother. 112, DOI: 10.1016/j.biopha.2019.108690 (2019).
Holohan, C. et al., "Cancer drug resistance: an evolving paradigm," Nat Rev Cancer 13, pp. 714-726 (2013).
Hu, F. et al., "Biological imaging of chemical bonds by stimulated Raman scattering microscopy," Nat Methods vol. 16, pp. 830-842 (2019).
Huang, K.C. et al., "Multiplex stimulated Raman scattering imaging cytometry reveals lipid-rich protrusions in cancer cells under stress condition," iScience 23, DOI: 10.1016/j.sci.2020.100953 (2020).
Itoh, T. et al., "Cisplatin induces production of reactive oxygen species via NADPH oxidase activation in human prostate cancer cells," Free Radical Research 45, pp. 1033-1039 (2011).
Iwamoto, H. et al., "Cancer Lipid Metabolism Confers Antiangiogenic Drug Resistance," Cell Metab. 28, pp. 104-117 (2018).
Johnson, S.W. et al., "Relationship between platinum-DNA adduct formation and removal and cisplatin cytotoxicity In cisplatin-sensitive and -resistant human ovarian cancer cells," Cancer Res. 54, pp. 5911-5916 (1994).
Kim, J. & Deberardinis, R.J., "Mechanisms and Implications of Metabolic Heterogeneity in Cancer," Cell Metab. 30, 434-446 (2019).
Koppenol, W.H. et al., "Otto Warburg's contributions to current concepts of cancer metabolism," Nat Rev Cancer 11, pp. 325-337 (2011).
Koundouros, N. & Poulogiannis, G., "Reprogramming of fatty acid metabolism in cancer," Br J Cancer 122, pp. 4-22 (2020).
Langdon, S.P. et al., "Characterization and properties of nine human ovarian adenocarcinoma cell lines," Cancer Res. 48, pp. 6166-6172 (1988).
Li, J. & Cheng, J.X., "Direct visualization of de novo lipogenesis in single living cells," Sci. Rep. vol. 4:6807, DOI: 10.1038/srep06807 (2014).
Li, J. et al., "Abrogating cholesterol esterification suppresses growth and metastasis of pancreatic cancer," Oncogene vol. 35, pp. 6378-6388 (2016).
Li, J. et al., "Lipid desaturation is a metabolic marker and therapeutic target of ovarian cancer stem cells," Cell Stem Cell 20, pp. 303-314 e305 (2017).
Liao, C.S. & Cheng, J.X., "In situ and in vivo molecular analysis by coherent Raman scattering microscopy," Annu. Rev. Anal. Chem. vol. 9, pp. 69-93 (2016).
Lin, J. et al. The roles of glucose metabolic reprogramming in chemo- and radio-resistance. J. Exp. Clin. Cancer Res. 38:218, DOI 10.1186/s13046-019-1214-z (2019).
Long, R. et al., "Two-color vibrational imaging of glucose metabolism using stimulated Raman scattering," Chem Commun (Camb) vol. 54, pp. 152-155 (2018).
Ma, Y. et al., "Fatty acid oxidation: An emerging facet of metabolic transformation in cancer," Cancer Lett. 435, pp. 92-100 (2018).
Martinez-Outschoorn, U.E. et al., "Cancer metabolism: a therapeutic perspective," Nat. Rev. Clin. Oncol. 14, pp. 11-31 (2017).
Marullo, R. et al., "Cisplatin induces a mitochondrial-ROS response that contributes to cytotoxicity depending on mitochondrial redox status and bioenergetic functions," PLoS One 8(11):e81162, DOI: 10.1371/journal.pone.0081162 (2013).
McArthur, M.J. et al., "Cellular uptake and intracellular trafficking of long chain fatty acids," Journal of Lipid Research 40, pp. 1371-1383 (1999).
Melone, M.A.B. et al., "The carnitine system and cancer metabolic plasticity," Cell Death Dis. 9:228, DOI: 10.1038/s41419-018-0313-7 (2018).
Miranda, F. et al., "Salt-Inducible Kinase 2 Couples Ovarian Cancer Cell Metabolism with Survival at the Adipocyte-Rich Metastatic Niche," Cancer Cell 30, pp. 273-289 (2016).
Mukherjee, A. et al., "Adipocyte-Induced FABP4 Expression in Ovarian Cancer Cells Promotes Metastasis and Mediates Carboplatin Resistance," Cancer Res 80, pp. 1748-1761 (2020).
Mullarky, E. & Cantley, L.C., "Diverting Glycolysis to Combat Oxidative Stress," Innovative Medicine (Nakao, K. et al., eds.), pp. 3-23 (Springer Japan, Tokyo; 2015).
Nieman, K.M. et al., "Adipocytes promote ovarian cancer metastasis and provide energy for rapid tumor growth," Nature Medicine 17, pp. 1498-1503 (2011).
Pascual, G. et al., "Targeting metastasis-initiating cells through the fatty acid receptor CD36," Nature 541, pp. 41-45 (2017).
Peck, B. et al., "Inhibition of fatty acid desaturation is detrimental to cancer cell survival in metabolically compromised environments," Cancer & Metab. 4:6 DOI 10.1186/s40170-016-0146-8 (2016).
Rahman, M. & Hasan, M., "Cancer Metabolism and Drug Resistance," Metabolites 5, pp. 571-600 (2015).
Rehman, S.K. et al., "Colorectal Cancer Cells Enter a Diapause-like DTP State to Survive Chemotherapy," Cell 184, pp. 226-242 (2021).
Robinson, M.D. et al., "edgeR: a Bioconductor package for differential expression analysis of digital gene expression data," Bioinformatics vol. 26, No. 1, pp. 139-140 (2010).
Rottenberg, S. et al., "The rediscovery of platinum-based cancer therapy," Nat Rev Cancer 21, pp. 37-50 (2021).

\* cited by examiner

DEVICE FOR DETECTION OF CELLULAR STRESS

CROSS-REFERENCE TO RELATED APPLICATION

This application is a continuation of U.S. application Ser. No. 17/839,080, filed Jun. 13, 2022, which claims the benefit under 35 U.S.C. § 119(e) of U.S. Provisional Application No. 63/210,286, filed Jun. 14, 2021, the contents of which are incorporated herein by reference in their entirety.

GOVERNMENT SUPPORT

This invention was made with government support under Contract No. CA224275 awarded by the National Institutes of Health. The government has certain rights in the invention.

SEQUENCE LISTING

The instant application contains a Sequence Listing which has been submitted electronically in XML format and is hereby incorporated by reference in its entirety. Said XML copy, created on May 15, 2023, is named BOS-0021CON.xml and is 31 KB bytes in size.

TECHNICAL FIELD

The disclosed technology relates to assays for determining resistance in a target cell or tissue to a therapy associated with cellular stress, and methods of using the assays.

BACKGROUND

Metabolic reprogramming in cancer cells has been recognized since the discovery of the Warburg effect in 1920s [1, 2]. Increased aerobic glycolysis is now widely considered as a hallmark of many cancers and clinically exploited as a target for cancer therapy and a cancer biomarker for diagnosis [3]. In the past decade, numerous studies have investigated the heterogeneity and complexity of cancer metabolism beyond the Warburg effect [4]. Metabolic reprogramming allows cancer cells to adapt to intrinsic or extrinsic cues from the microenvironment through plasticity and high flexibility in nutrient acquisition and utilization [5]. Particular attention has been paid to metabolic alterations associated with critical steps of cancer progression, such as metastasis initiation, circulation and colonization [5-7]. Metabolic reprogramming in cancer stem cells identified potential vulnerabilities for cancer stem cells targeting therapy [8, 9]. Cancer cells also rewire their metabolic dependencies within a specific microenvironment niche by interacting with stroma cells or with the surrounding adipocytes [11, 12]. Further, alterations in nutrient utilization under metabolic stress conditions have recently been reported [13-15]. Despite these recent advances, the understanding of cancer cell metabolism remains incomplete. One of the less studied areas is cancer metabolic reprogramming associated with resistance to therapy.

Therapeutic resistance remains one of the biggest challenges facing cancer treatment. Resistance to chemotherapy or molecularly targeted therapies is a major cause of tumor relapse and death [16]. Emerging studies support an association between metabolic reprogramming and cancer drug resistance [17, 18]. Several studies have linked the Warburg effect to resistance to radiation [19] and lactate production was shown to promote resistance to chemotherapy in cervical cancer [20]. Altered lipid metabolism has also been implicated in acquisition of drug resistance [21]. Increased de novo lipogenesis mediated by FASN facilitated gemcitabine resistance in pancreatic cancer [22] while cancer associated adipose tissue promoted resistance to antiangiogenic interventions by supplying fatty acid to cancer cells in regions where the glucose demand was insufficient [23]. Additionally, lipid droplet production mediated by lysophosphatidylcholine acyltransferase 2 promoted resistance of colorectal cancer cells to 5-fluorouracil and oxaliplatin [24]. It has been proposed that drug tolerant cells adopt a state of diapause similar to suspended embryonic development to survive chemotherapy toxic insults, in which cell proliferation and metabolic processes are suppressed [25]. These studies support that metabolic reprograming underlie development of drug resistance and point to potential metabolic vulnerabilities of resistant cancer cells, which remain underutilized.

Platinum-based drugs, including cisplatin, carboplatin and oxaliplatin, represent one class of the most widely used chemotherapy drugs [26]. Resistance to platinum is a barrier to effective treatment in multiple cancers, including ovarian, testicular, bladder, head and neck, non-small-cell lung cancer and others [27]. Understanding the metabolic reprograming underlying platinum resistant cancer cells is critical for development of effective treatment strategies. Yet, precisely profiling metabolic reprogramming using conventional technology is difficult, because within a cell population, only a small portion of cells is drug resistant or tolerant. In this study, by taking advantage of a hyperspectral stimulated Raman scattering (SRS) imaging platform, we depict the metabolic profile of platinum resistant cancer cells at the single cell level.

SRS microscopy is a recently developed label-free chemical imaging technique that detects the intrinsic chemical bond vibrations [28-31]. The value of SRS microscopy was demonstrated in identifying cholesteryl ester accumulation as a signature associated with multiple aggressive cancers [32, 33], discovering increased lipid desaturation in OC stem cells, and tracing metabolic flux by isotope labeling [34-36]. More recently, large-area hyperspectral SRS microscopy and high-throughput single cell analysis revealed lipid-rich protrusion in cancer cells under stress [37]. Raman spectromicroscopy based single cell metabolomics unveiled an important role of lipid unsaturation in aggressive melanoma [38]. This technology holds promise for understanding aerobic glycolysis and lipid metabolism associated with cellular stress.

SUMMARY

This disclosure provides an assay for determining resistance in a target cell or tissue to a therapy associated with cellular stress or perturbation, and methods of using the assay. One aspect of the disclosure is an assay for determining resistance in a target cell or tissue to a therapy associated with cellular stress comprising measuring with chemical microscopy a functional metabolic alteration or change in the target cell or tissue, and determining a metabolic index of resistance in the target cell or tissue to the therapy. The functional metabolic alteration or change is a change from glucose and glycolysis dependent anabolism and energy metabolism to fatty acid uptake and fatty acid oxidation dependent anabolism and energy metabolism. In embodiments, the metabolic index correlates to resistance to a therapy in the target cell when the metabolic alteration or change is a decrease in glucose and glycolysis dependent anabolism and an increase in fatty acid uptake and fatty acid oxidation dependent anabolism and energy metabolism. In some embodiments, the metabolic index further correlates to resistance to the therapy in the target cell when the metabolic change is a decrease in de novo lipogenesis in the target cell.

Another aspect of the disclosure is use of the disclosed assay in methods of treating or inhibiting resistance in a target cell or tissue to a therapy associated with cellular stress. Embodiments include a method of treating or inhibiting resistance in a target cell or tissue in a subject to a therapy associated with cellular stress in a subject by performing an assay as disclosed herein to determine a metabolic index of resistance in the target cell to the therapy, administering at least one inhibitor of fatty acid oxidation to the subject, and administering at least one therapy to the subject.

One embodiment of the method comprises measuring with chemical microscopy a functional metabolic change in glucose and glycolysis dependent anabolism and an increase in fatty acid uptake and oxidation in which the glucose and glycolysis dependent anabolism decreases and fatty acid uptake and oxidation increases.

In the disclosed embodiments, the target cell is a cell that may undergo metabolic reprogramming or alteration in response to cellular stress, such as a cancer cell, an immune cell, or a benign neoplasm. In the embodiments, the target cell is a cancer cell, for example ovarian, prostate, testicular, bladder, pancreatic, lung, breast, esophageal, head, and neck cancer. In the embodiments, the therapy is a cancer therapy that induces a metabolic alteration in the cell.

Other features and advantages of aspects of the disclosure will become apparent from the following more detailed description, taken in conjunction with the accompanying drawings, which illustrate, by way of example, the principles of aspects of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The teachings in the present disclosure will be more fully understood from the following description of various illustrative embodiments, when read together with the accompanying drawings. It should be understood that the drawings described below are for illustration purposes only and are not intended to limit the scope of the present teachings in any way.

FIG. 1A is an image of processing flow for high-throughput single cell analysis of lipids using hyperspectral stimulated Raman scattering (SRS) imaging; lipids were color-coded based on the colors of their parental cells; quantitative analysis of cell morphology, lipid quantity and intensity were also produced along with the images; image area is 500 µm by 500 µm. FIG. 1Q shows quantitative analysis of SRS signal from lipid in carboplatin sensitive and resistant ovarian tumor tissue by area fraction. Data for FIGS. 1P-1Q are presented as mean+SD; n=3 animals; two-sided Student's t test; P=0.043; * P<0.05. All scale bar: 20 µm.

FIG. 2A shows representative bright field and SRS images of PEO1 and PEO4 cells fed with glucose-$d_7$ for 3 days. FIG. 2B shows quantitative analysis of SRS signal of C-D bonds in glucose-$d_7$ fed PEO1 and PEO4 cells by mean intensity and area fraction; n=5. P=0.0076 and 0.0083. FIG. 2C shows representative bright field and SRS images of PEO1 and PEO4 cells fed with PA-$d_{31}$ for 6 h. FIG. 2D shows quantitative analysis of SRS signal of C-D bonds in PA-$d_{31}$ fed PEO1 and PEO4 cells by mean intensity and area fraction; n=6. P=0.0051 and $3\times10^{-5}$. FIG. 2E presents representative bright field and SRS images of PEO1 and PEO4 cells fed with OA-$d_{34}$ for 6 h. FIG. 2F shows quantitative analysis of SRS signal of C-D bonds in OA-d34 fed PEO1 (n=6) and PEO4 (n=7) cells by mean intensity and area fraction; P=0.030 and 0.0048. FIG. 2G presents representative SRS images of SKOV3 and SKOV3-cisR cells fed with glucose-$d_7$ for 3 days and quantitative analysis of SRS signal of C-D bonds by mean intensity. FIGS. 2H-2I present representative SRS images of SKOV3 and SKOV3-cisR cells fed with PA-$d_{31}$ for 6 h (FIG. 2H) (n=5. P=0.0010) and fed with OA-$d_{34}$ for 6 h and quantitative analysis of SRS signal of C-D bonds by mean intensity (FIG. 2I) (n=8. P=$2.2\times10^{-5}$). The results in all the bar charts are shown as means+SD. All statistical significance was analyzed using one-sided Student's t test. *P<0.05, P<0.01, and *P<0.001. All scale bar: 20 µm. FIGS. 2J-2K present representative bright field and SRS images of OVCAR5 and OVCAR5-cisR cells (FIG. 2J) and of COV362 and COV362-cisR cells (FIG. 2K), fed with glucose-$d_7$ for 3 days, PA-$d_{31}$ for 6 h, or OA-$d_{34}$ for 6 h; n=6. FIG. 2L shows representative sum of hSRS and phasor mapped lipid image of SKOV3 and SKOV3-cisR cells treated with vehicle or 10 µM C-75. FIG. 2M shows quantitative analysis of SRS signal from lipid in SKOV3 and SKOV3-cisR cells treated with vehicle or 10

μM C-75. The results are shown as means+SD, n=6-8. *P<0.05, P<0.01, and *P<0.001.

Figure 3A:
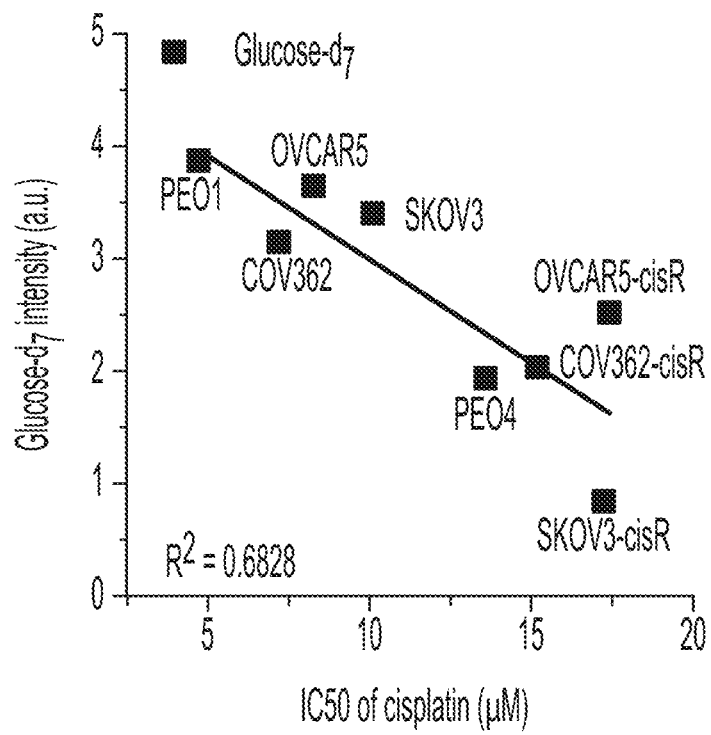
Figure 3B:
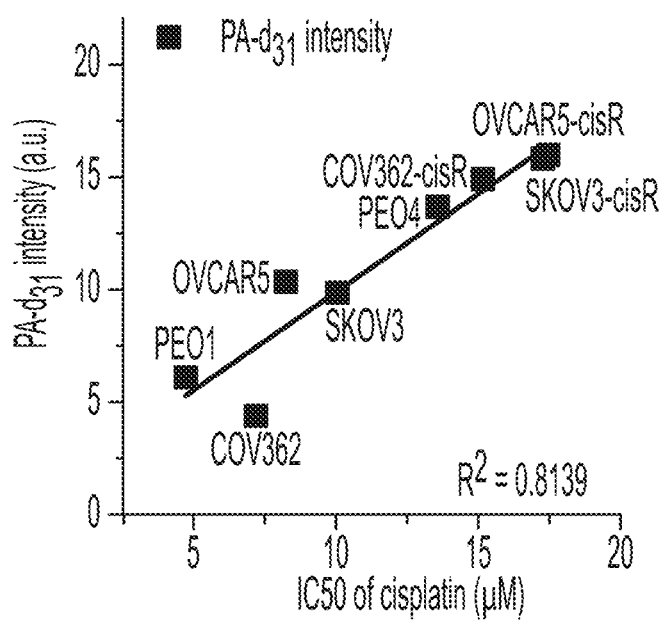
Figure 3C:
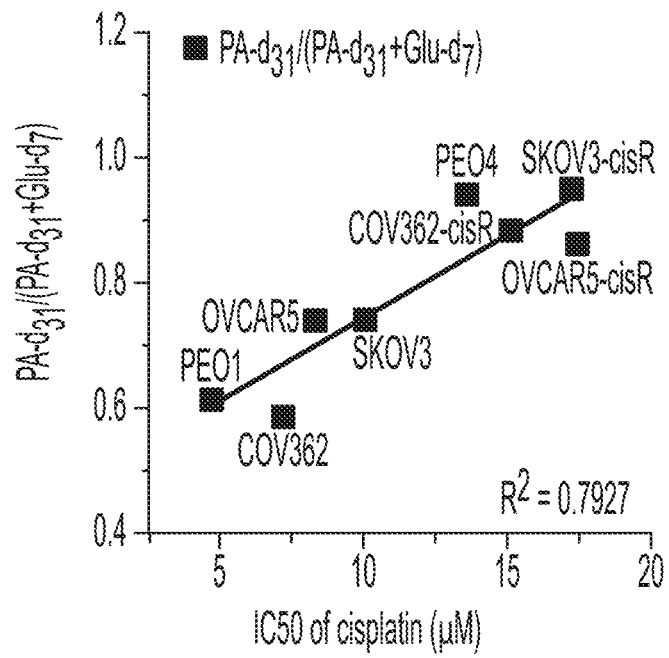
Figure 3D:
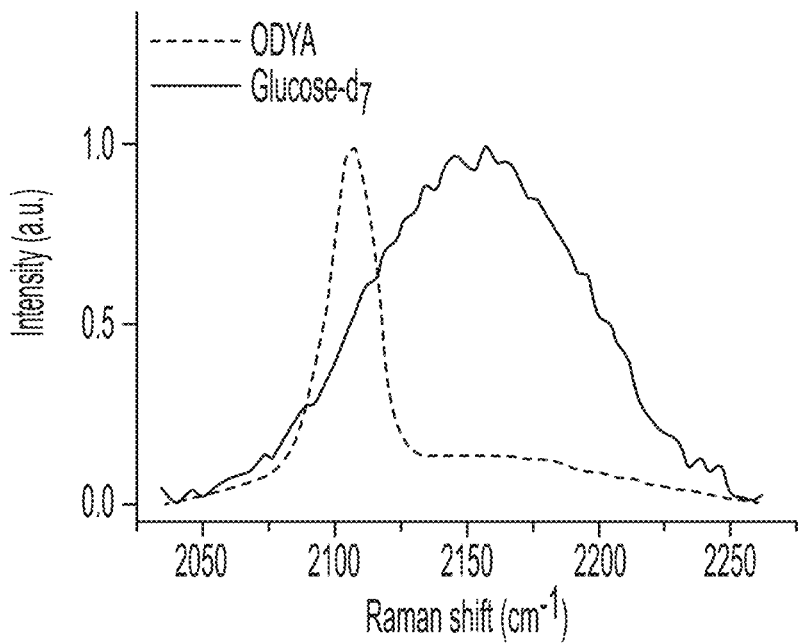
Figure 3E:
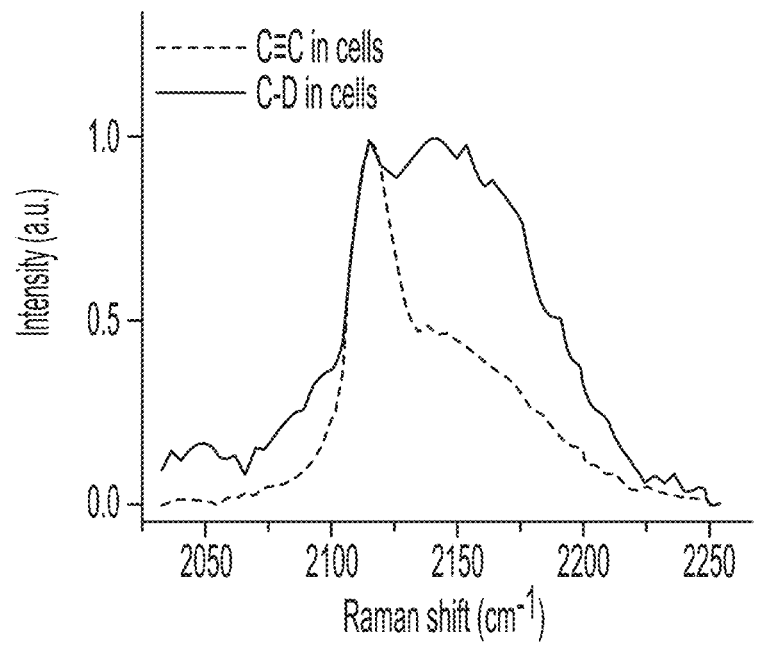
Figure 3F:
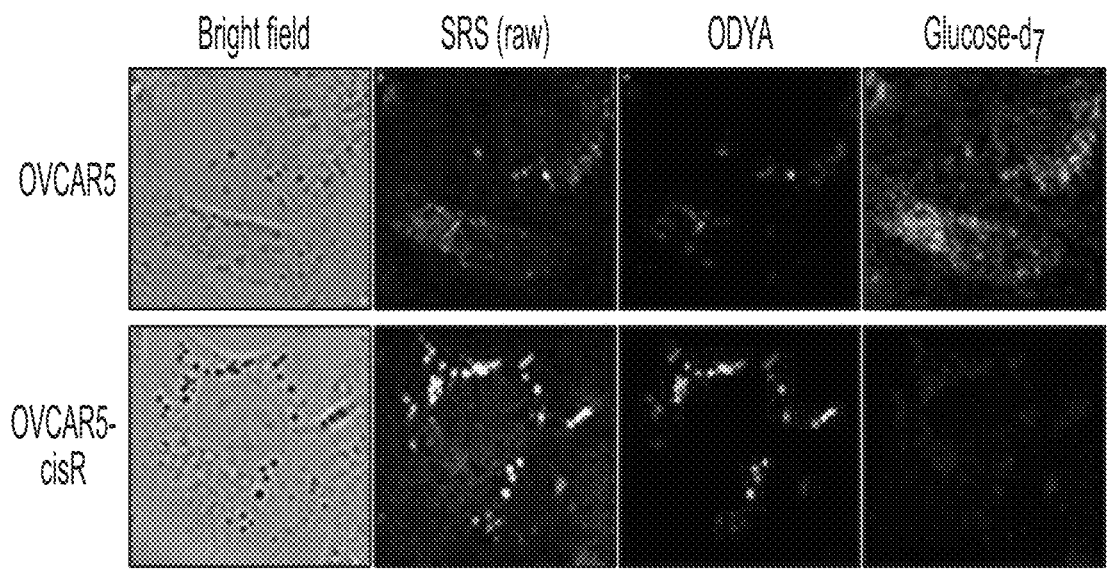
Figure 3G:
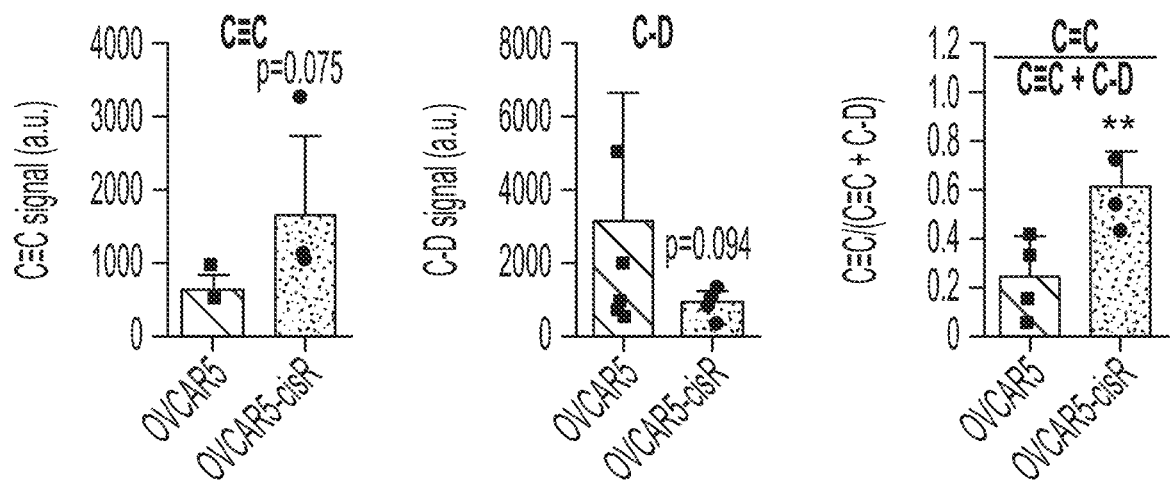
Figure 3H:
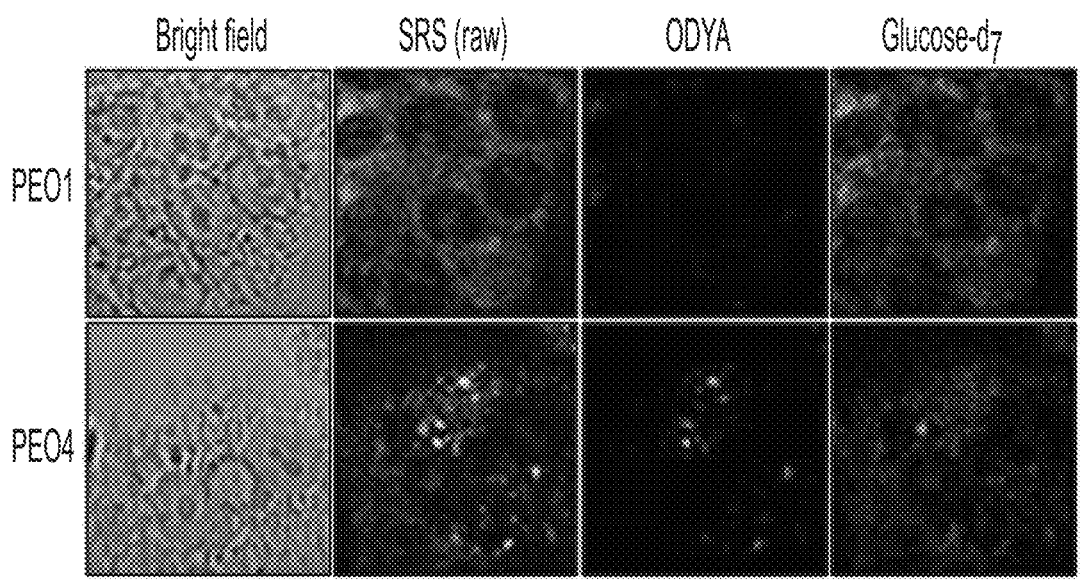
Figure 3I:
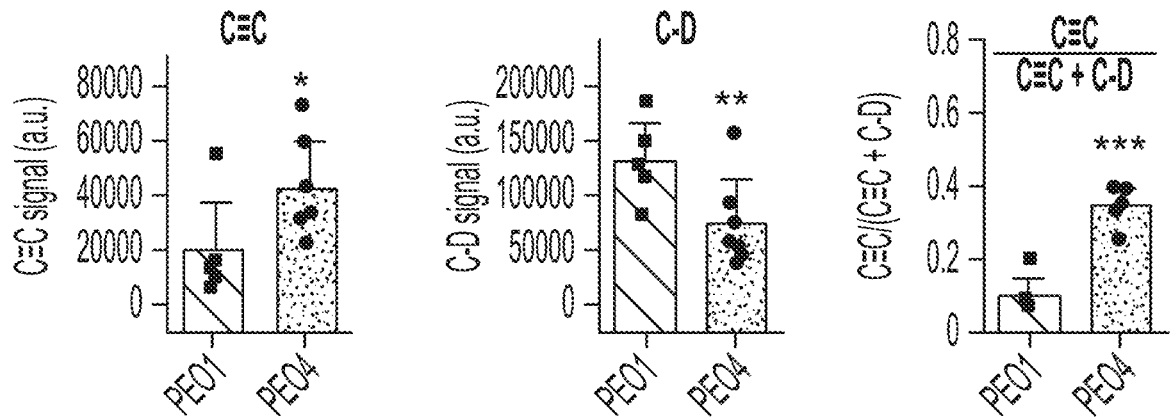
Figure 3J:
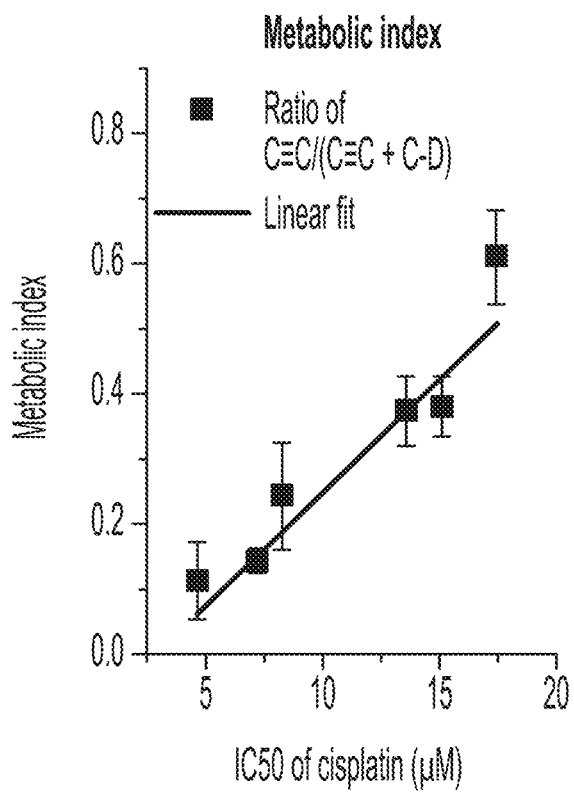
Figure 3K:
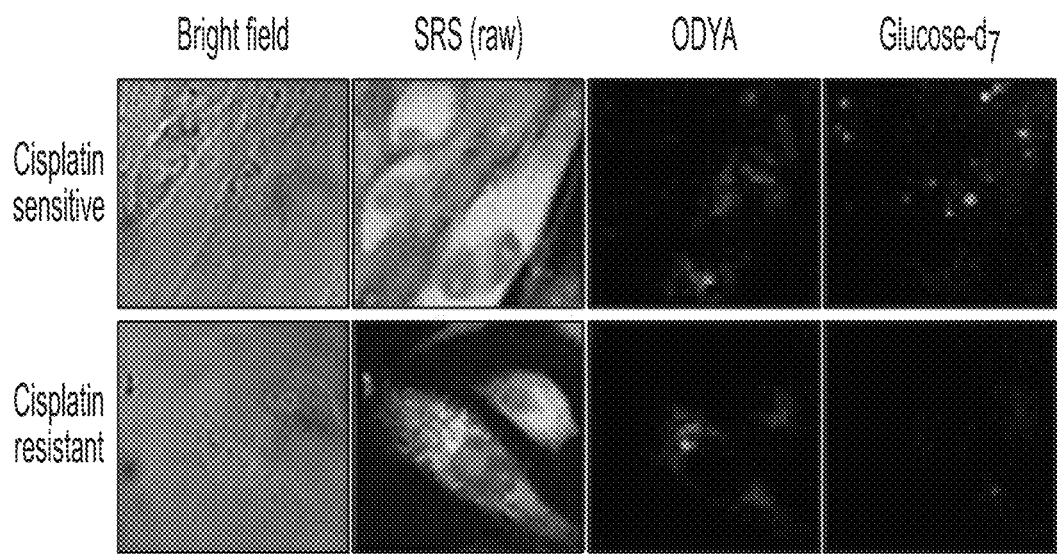
Figure 3L:
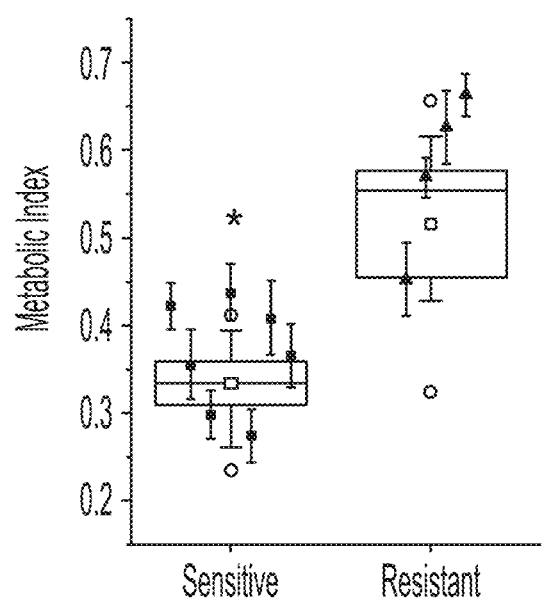
Figure 3M:
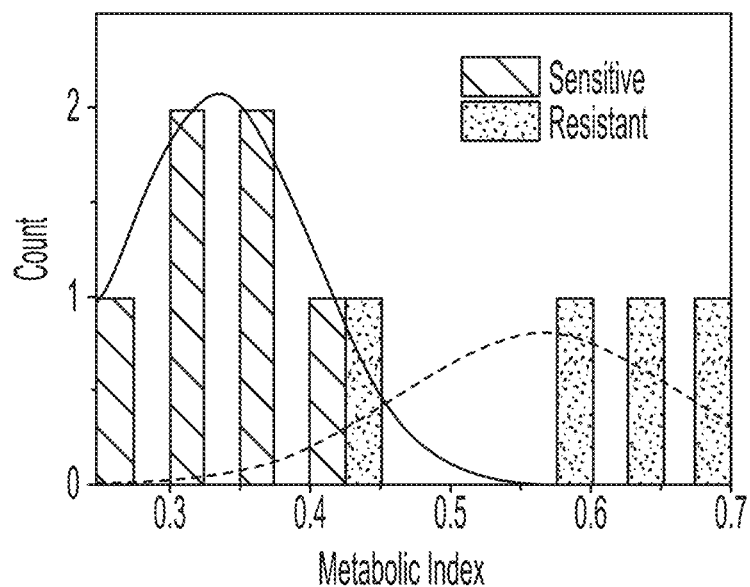
Figure 3N:
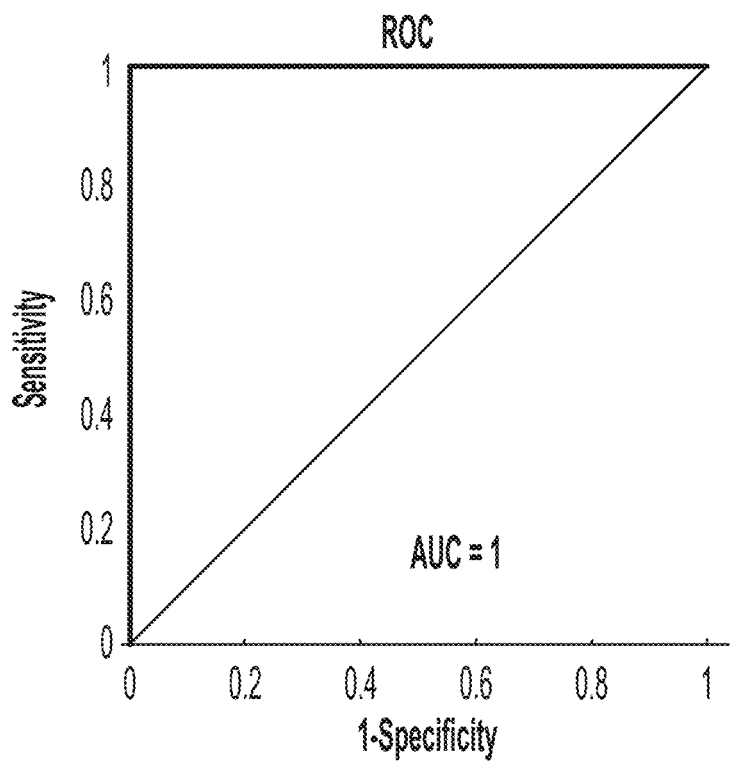

FIGS. 3A-3N show that metabolic index calculated by integrating glucose derived lipogenesis and fatty acid uptake directly correlates with cisplatin resistance. FIGS. 3A-3C present linear regression of glucose-$d_7$ intensity to $IC_{50}$s of cisplatin in various OC cell lines (FIG. 3A), of PA-d31 intensity to $IC_{50s}$ of cisplatin in various OC cell lines (FIG. 3B), and of PA-$d_{31}$/(PA-$d_{31}$+Glucose-$d_7$) to $IC_{50}$S of cisplatin in various OC cell lines (FIG. 3C). FIG. 3D shows normalized SRS spectra of 17-Octadecynoic Acid (ODYA) and glucose-d7 in cells. FIG. 3E presents output SRS spectra from phasor analysis of C≡C bonds from ODYA and C-D bonds from glucose-$d_7$ and metabolites. FIG. 3F presents representative bright field images, raw SRS images, and processed SRS images of ODYA and glucose-d7 in OVCAR5 and OVCAR5-cisR cells. FIG. 3G shows quantitative analysis of ODYA derived C≡C intensity (n=4), glucose-$d_7$ derived C-D intensity (n=6), and the ratio of C≡C/(C≡C+C-D (n=4)) in OVCAR5 and OVCAR5-cisR cells, P=0.0082. FIG. 3H presents representative bright field images, raw SRS images, and processed SRS images of ODYA and glucose-$d_7$ in PEO1 and PEO4 cells; scale bar 20 μm. FIG. 3I shows quantitative analysis of ODYA derived C≡C intensity, glucose-d7 derived C-D intensity, and the ratio of C≡C/(C≡C+C-D) in PEO1 (n=6) and PEO4 cells (n=7). The results in all the bar charts are shown as means+SD. All statistical significance was analyzed using one-sided Student's t test. *P<0.05, P<0.01, and *P<0.001. FIG. 3J shows linear regression of the metabolic index, as defined by the ratio of C≡C/(C≡C+C-D) to $IC_{50S}$ cisplatin in various OC cell lines; $R^2$=0.9235; n=6 for (a-c) and (e). FIG. 3K shows representative bright field images, raw SRS images, and processed SRS images of ODYA and glucose-$d_7$ in primary OC cells from cisplatin treatment resistant patients and from the cisplatin treatment sensitive patient. FIG. 3L shows quantitative analysis of metabolic index (the ratio of C≡C/(C≡C+C-D) for primary OC cells from cisplatin treatment resistant patients and from the cisplatin treatment sensitive patient; each data point represents the average metabolic index of individual cancer cells from a patient and its error bar indicates the SEM; n=30, 31, 19, 25, 27, 33, 12, 11, 24, 20 and 30. The box plot indicates analysis of each group (sensitive (n=7) v.s. resistant (n=4)). The bound of outer box represents SEM; inner box indicates mean; lines represent medium; whiskers indicate 25% to 75% of data; circles indicate maxima and minima of data. The statistical significance was analyzed using two-sided Student's t test; P=0.011. *P<0.05. All scale bar: 20 μm. FIG. 3M shows histograms of metabolic index of primary ovarian cancer cells from platinum resistant patients and platinum sensitive patients; n=4. FIG. 3N is a receiver operating characteristic (ROC) curve for metabolic index of primary ovarian cancer cells from patients with platinum resistant or platinum sensitive tumors. AUC: area under curve.

Figure 4A:
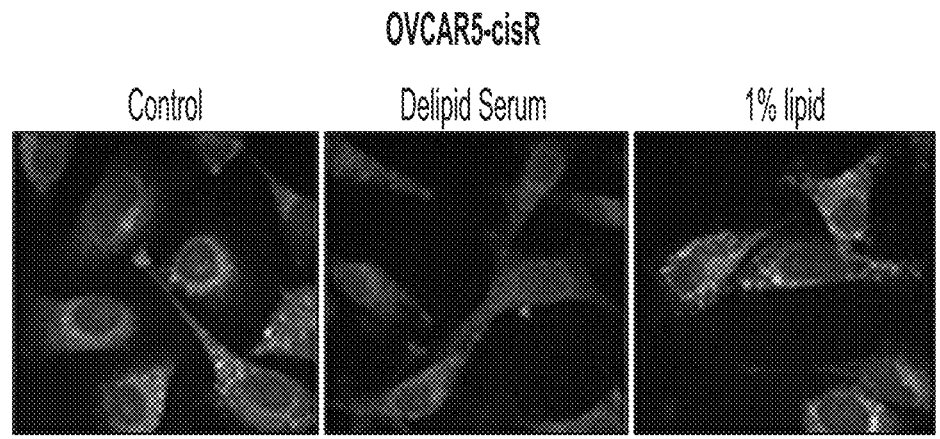
Figure 4B:
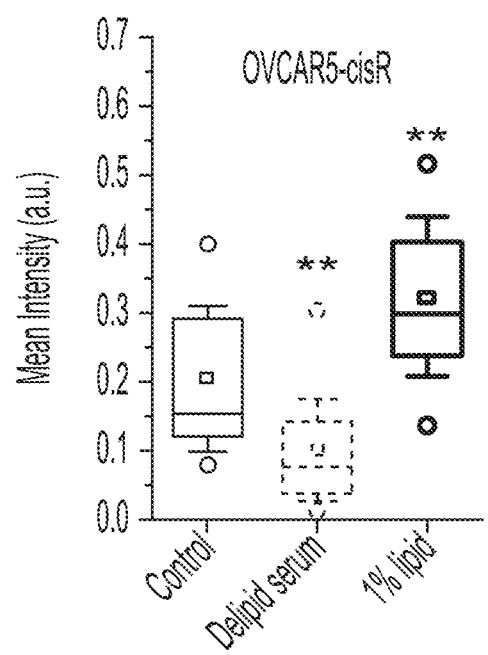
Figure 4C:
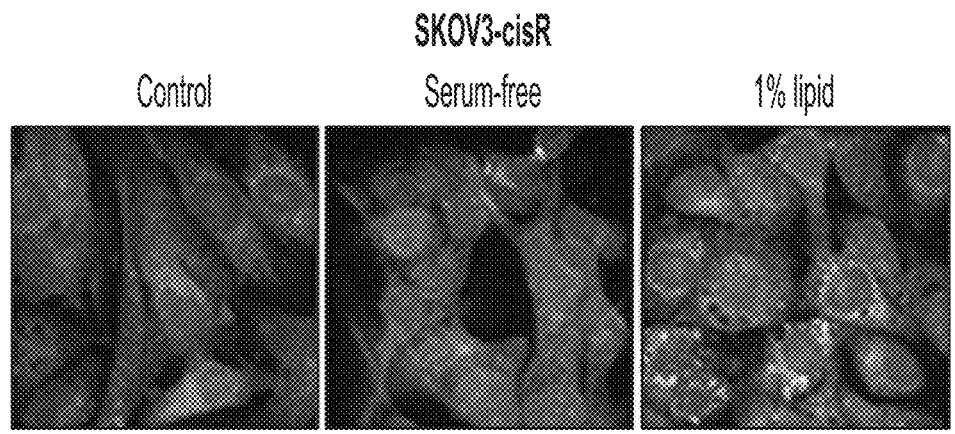
Figure 4D:
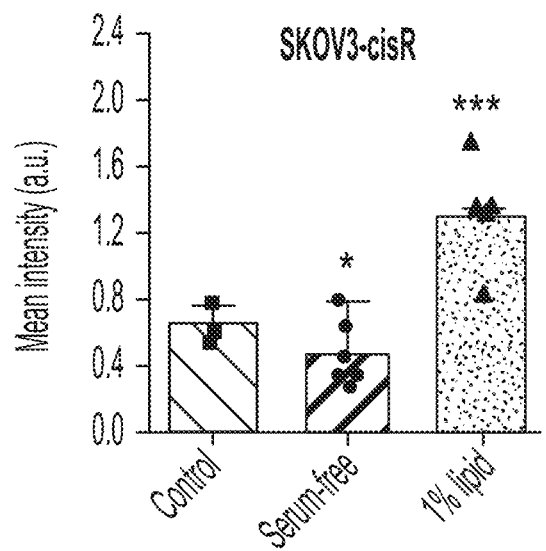
Figure 4E:
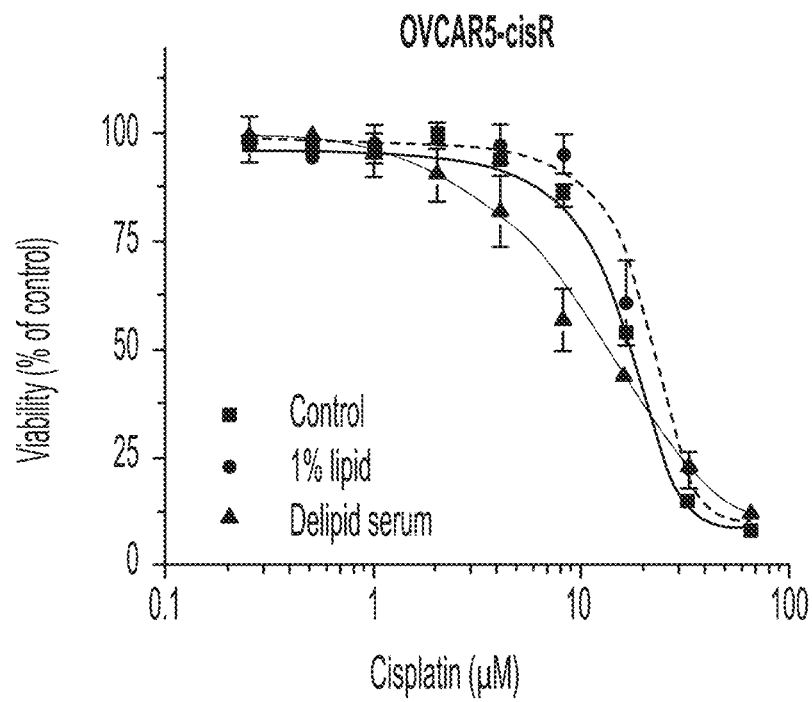
Figure 4F:
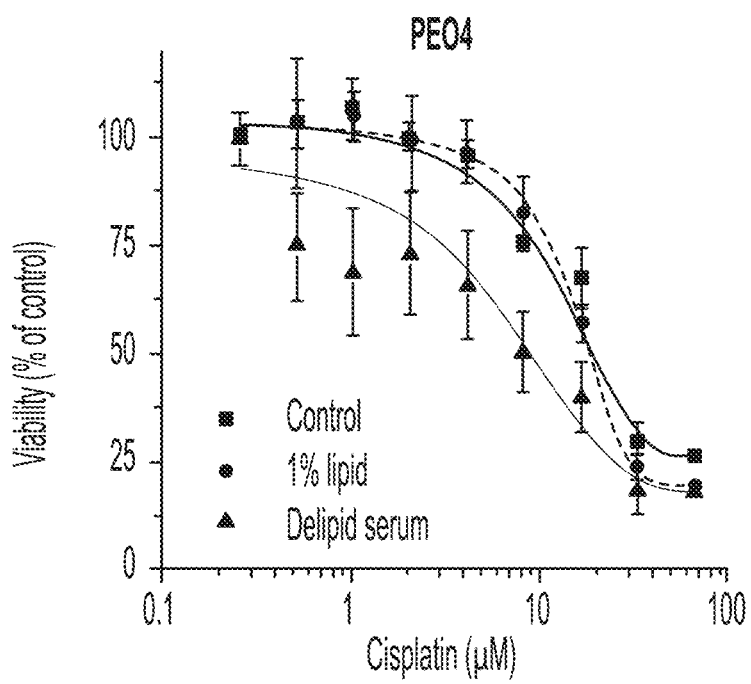
Figure 4G:
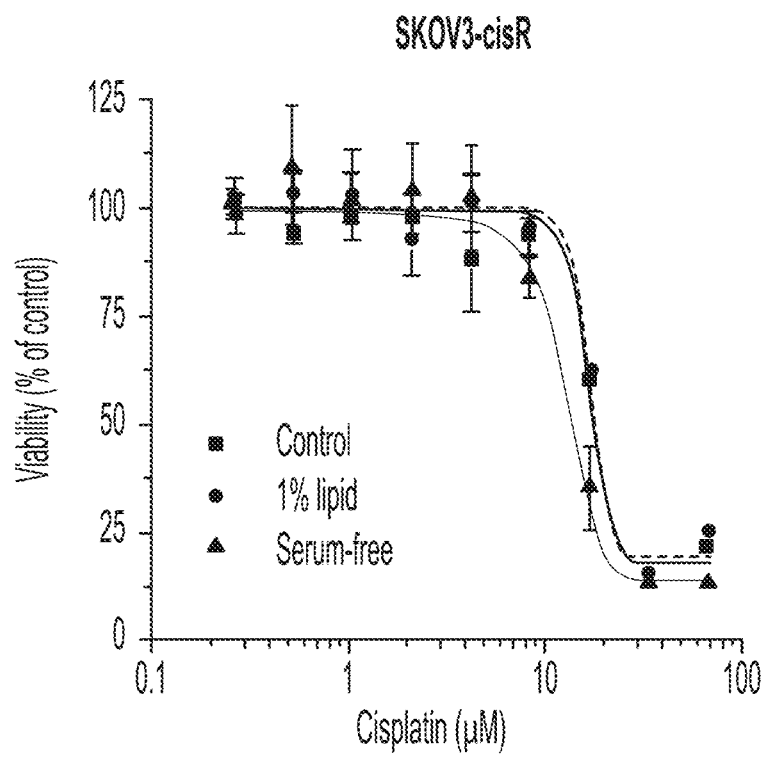
Figure 4H:
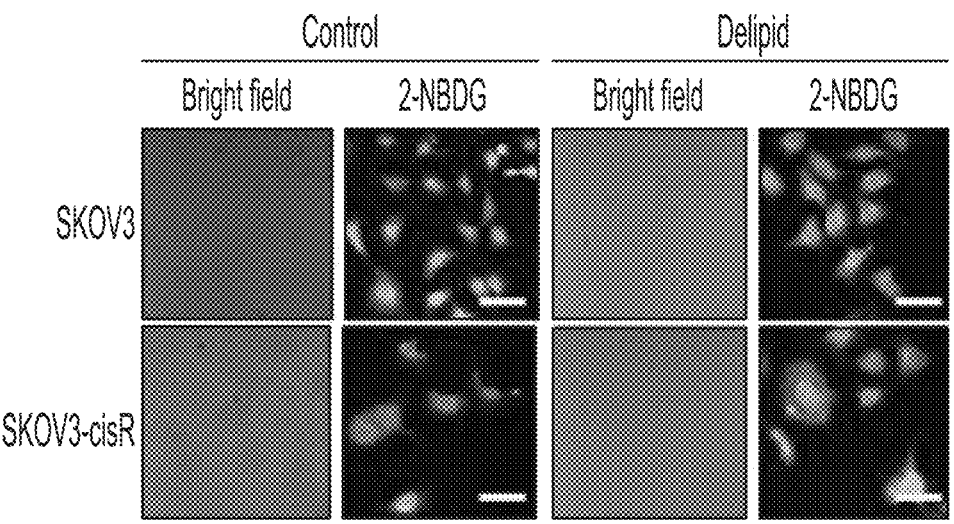
Figure 4I:
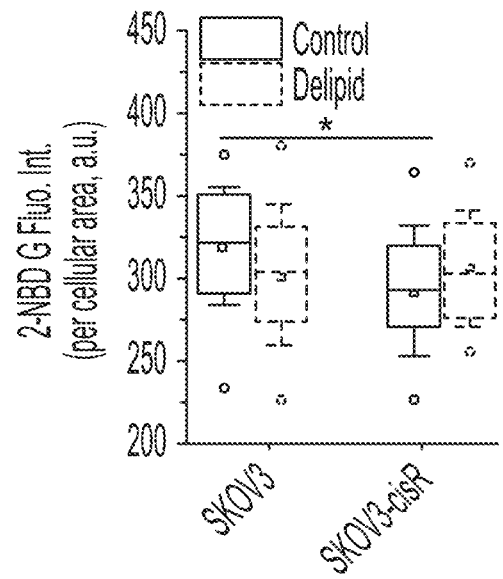
Figure 4J:
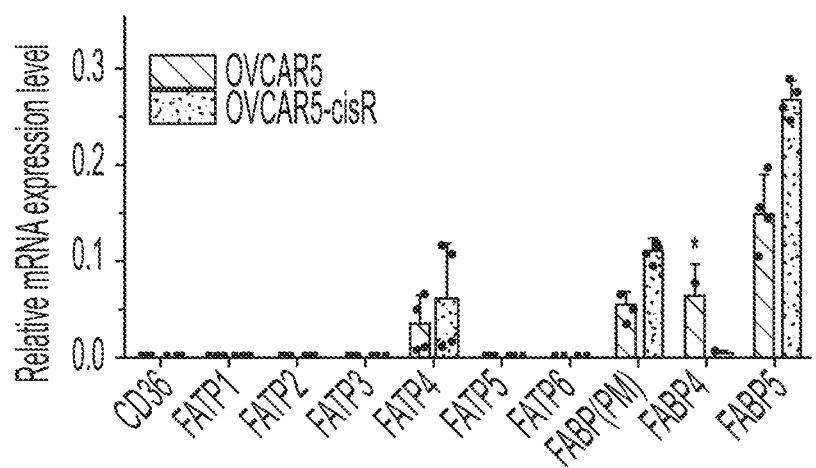
Figure 4K:
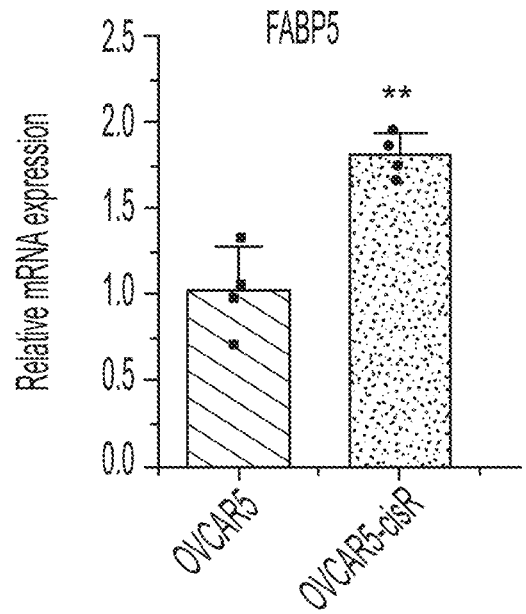
Figure 4L:
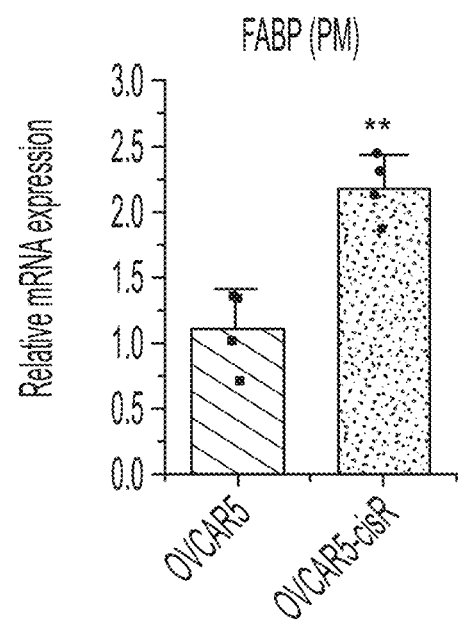
Figure 4M:
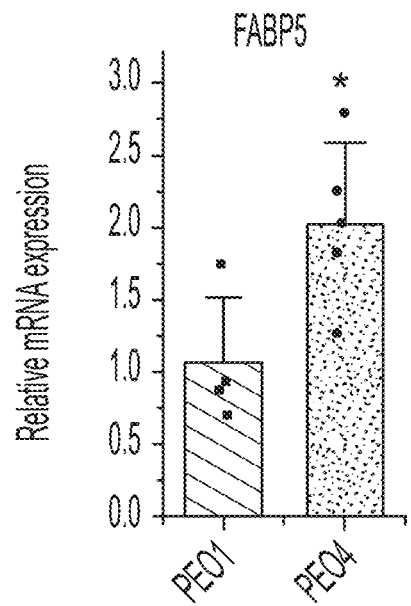
Figure 4N:
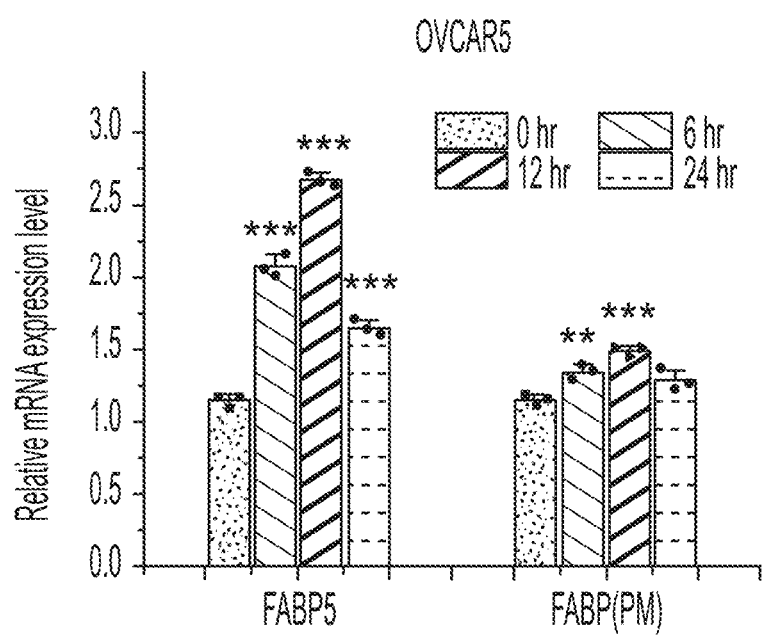
Figure 4O:
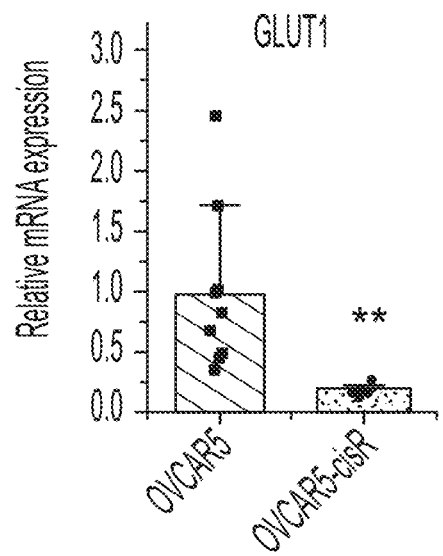
Figure 4P:
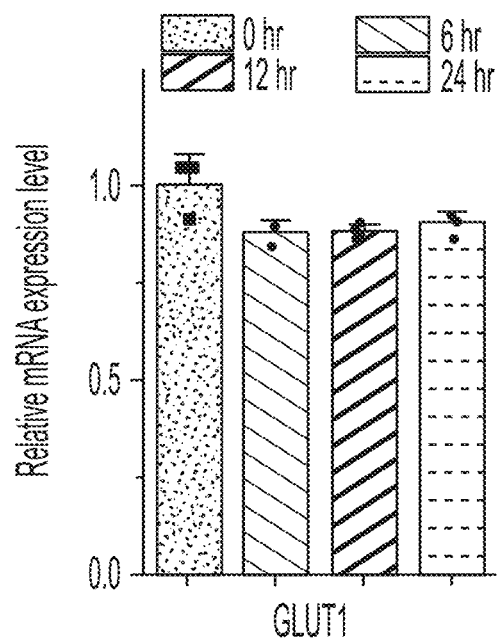
Figure 4Q:
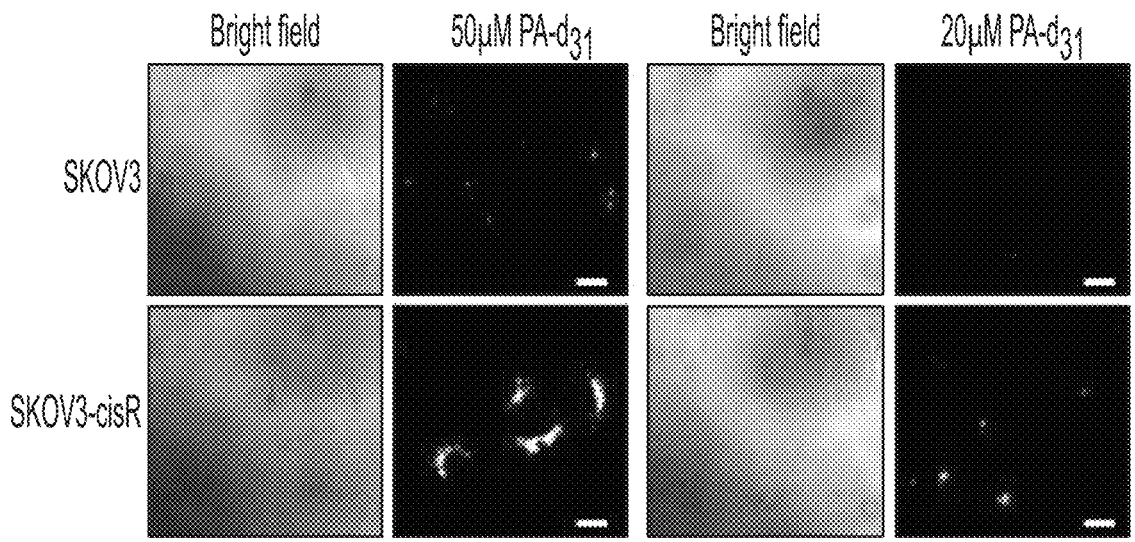
Figure 4R:
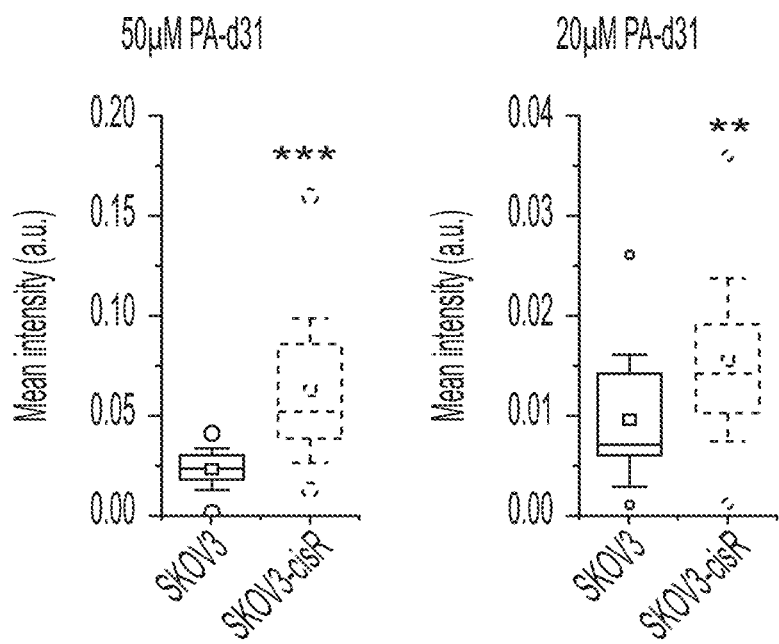
Figure 4S:
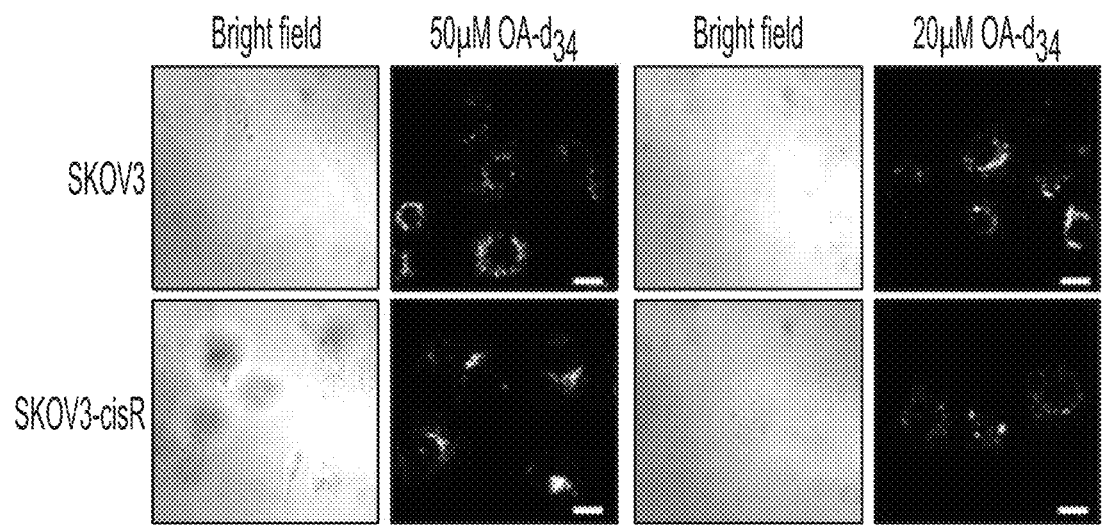
Figure 4T:
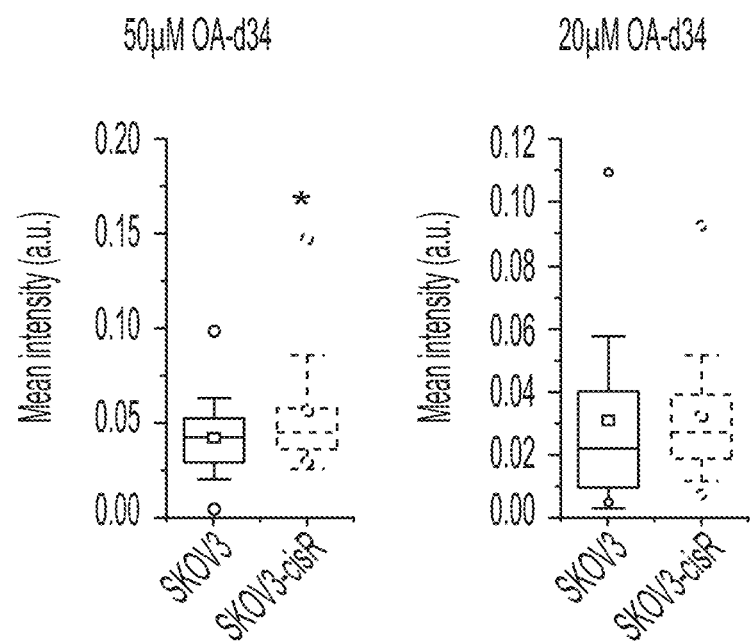
Figure 4U:
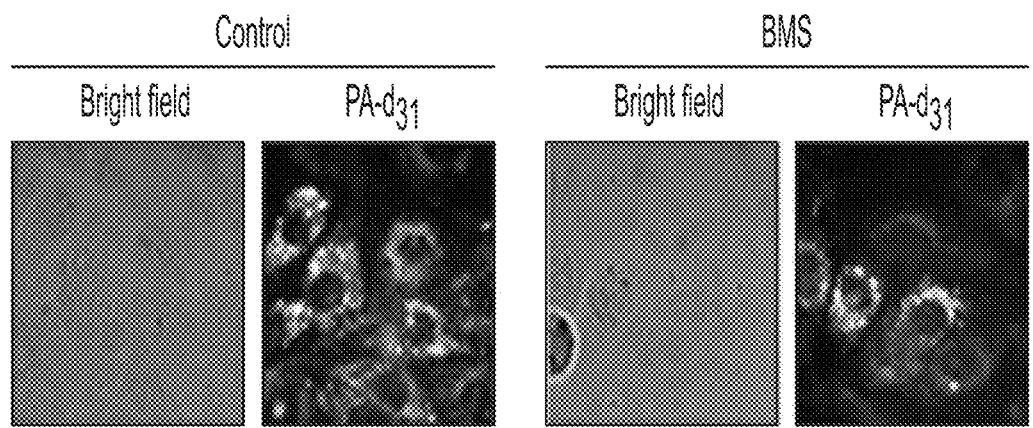
Figure 4V:
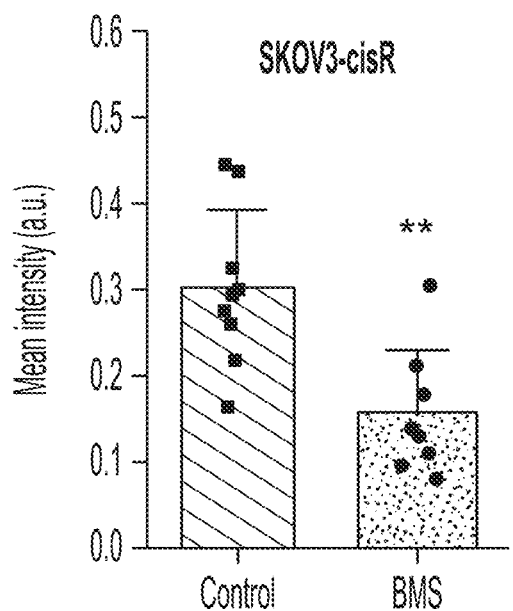
Figure 4W:
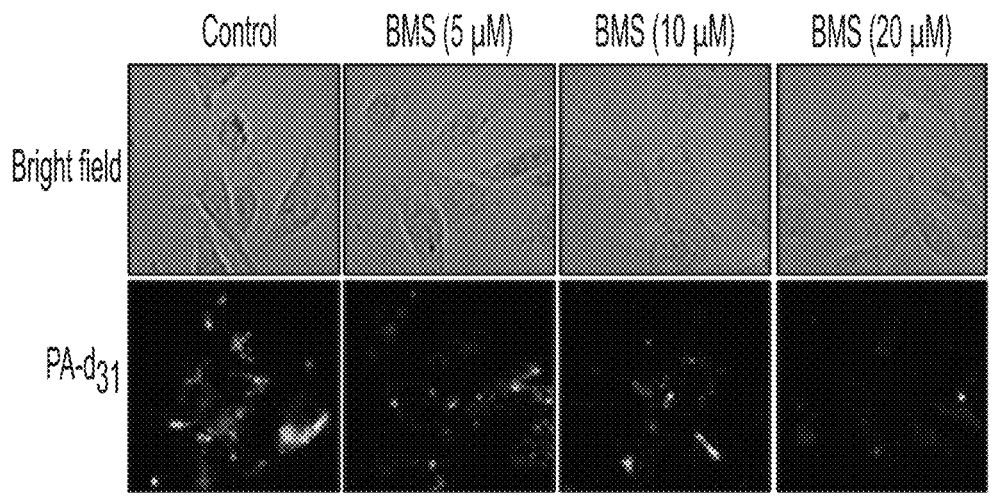
Figure 4X:
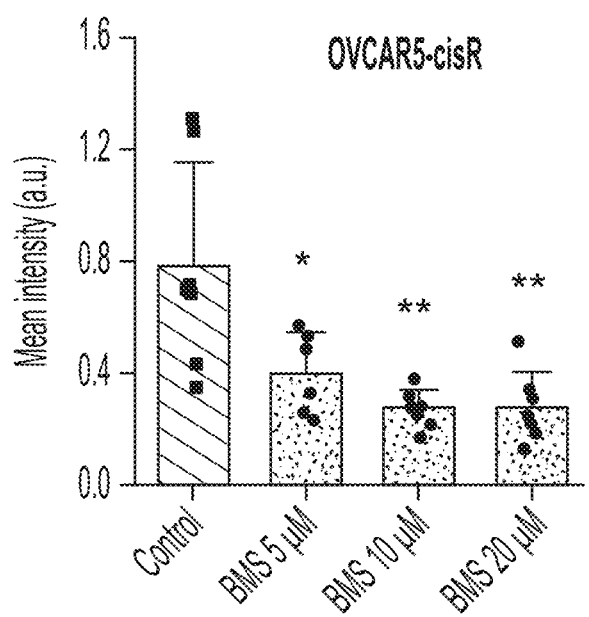
Figure 4Y:
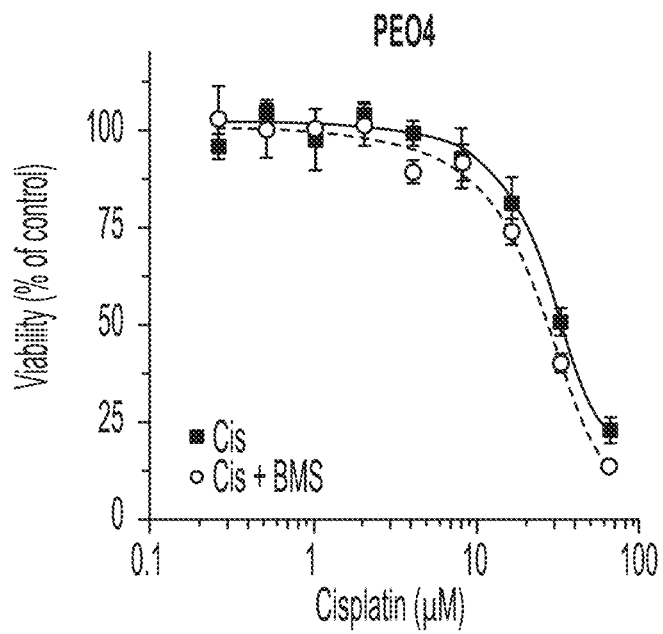
Figure 4Z:
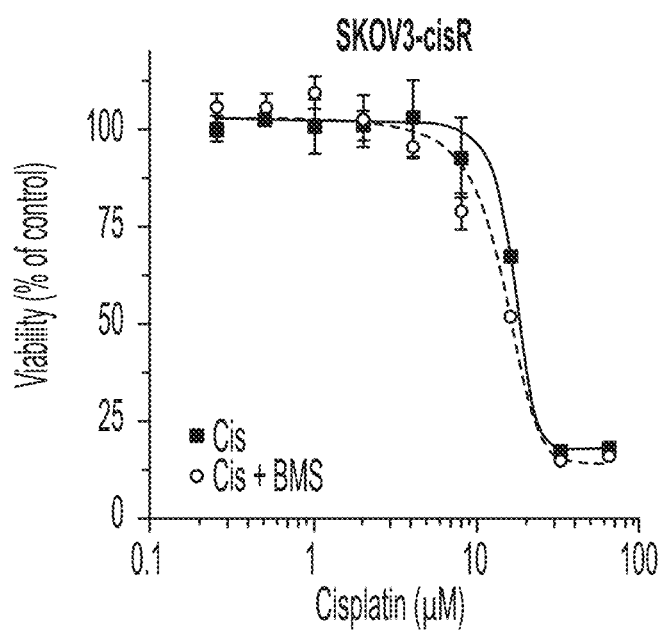
Figure 4A:
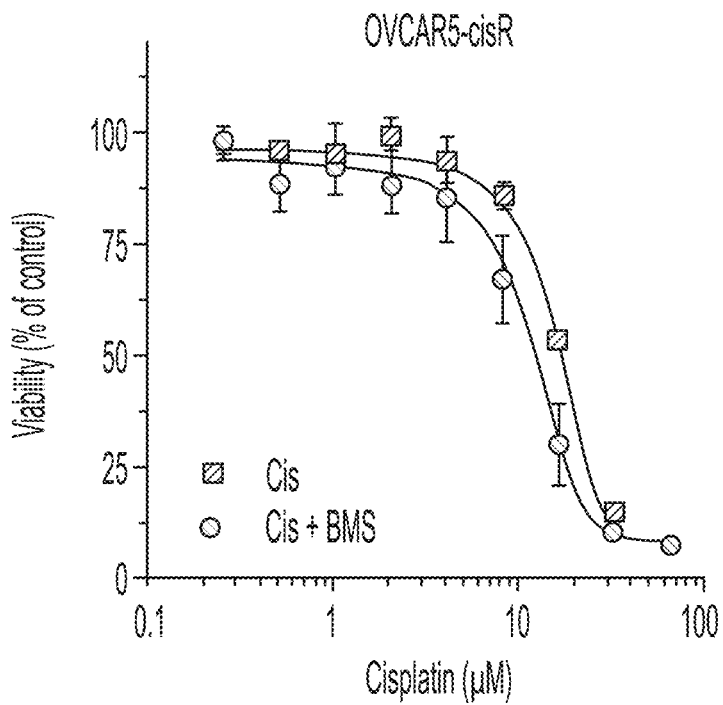
Figure 4B:
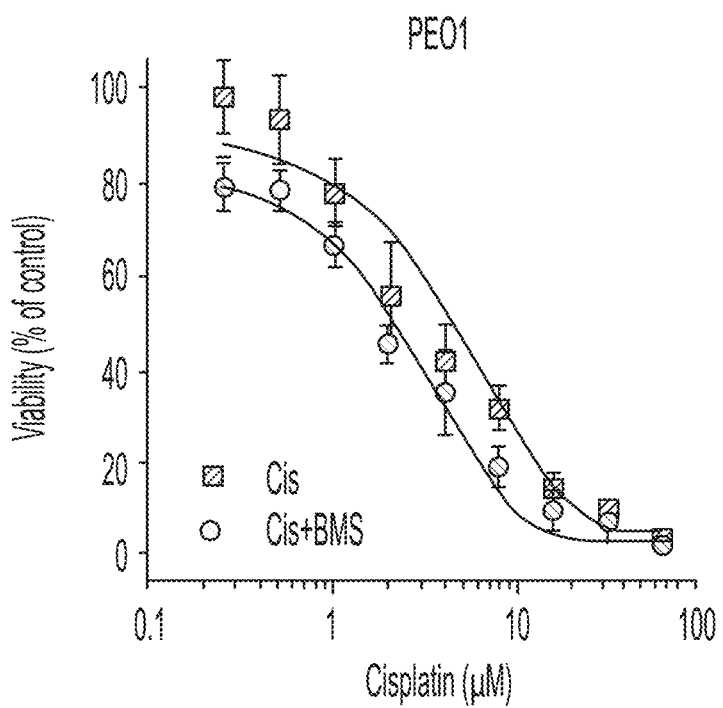
Figure 4C:
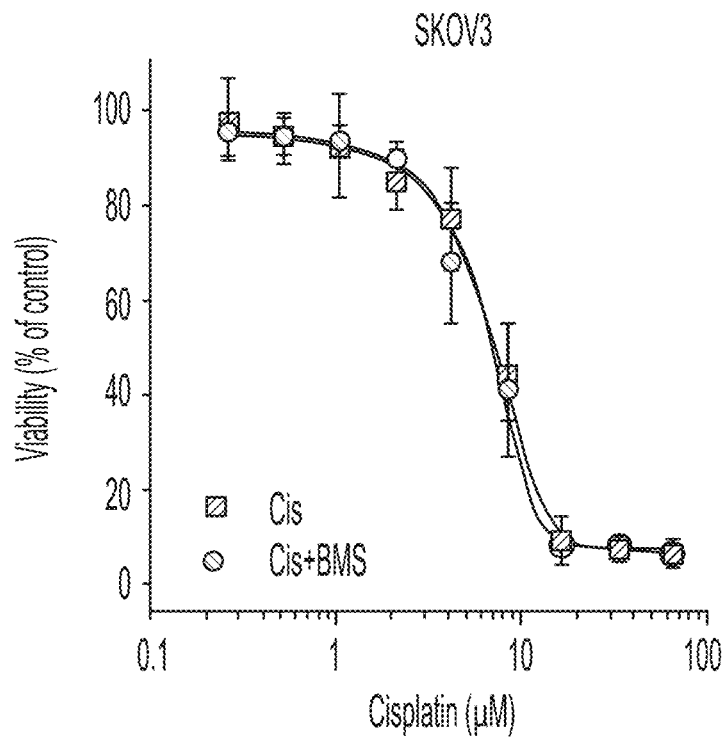
Figure 4D:
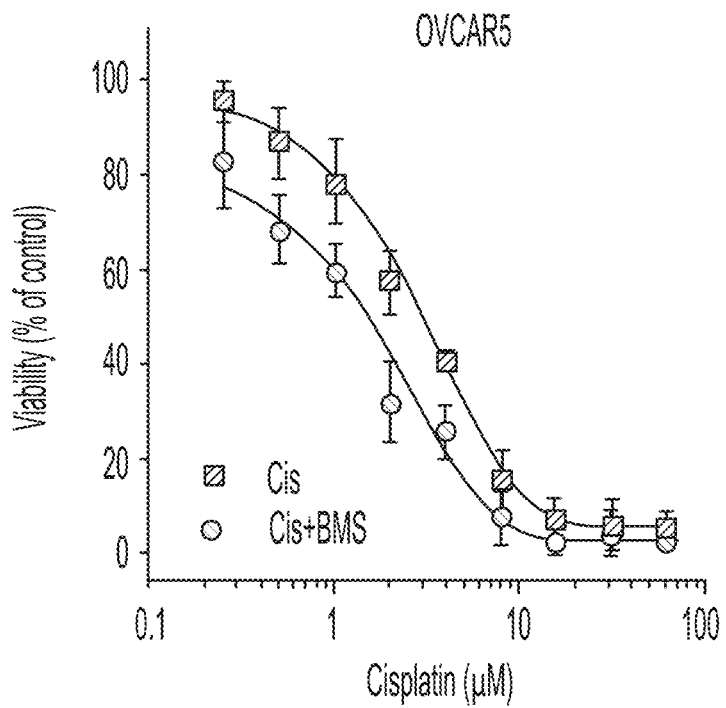

FIGS. 4A-4DD show that fatty acid uptake directly contributes to cisplatin resistance. FIG. 4A is a SRS image of OVCAR5-cisR cell cultured with control serum (FBS), delipid serum or control serum supplemented with 1% lipid mixture for 24 hours. FIG. 4B shows quantitative C-H signal from lipid droplet in FIG. 1A (OVCAR5-cisR cell cultured with control serum (FBS), delipid serum, or control serum supplemented with 1% lipid for 24 hours). FIG. 4C shows representative SRS images of SKOV3-cisR cell cultured with control serum (FBS) (n=5), no serum (n=6) and control serum supplemented with 1% lipid mixture (n=6) for 24 hours. Scale bar: 20 μm. FIG. 4D shows quantitative C-H signal from lipid droplet in FIG. 4C; P=0.044 and 0.00089. FIG. 4E shows a dose-response to cisplatin under culture environment with control, reduced (medium containing delipid serum or no serum) and increased (control serum supplemented with 1% lipid mixture) lipid content for OVCAR5-cisR cells; n=3 biological replicates. FIGS. 4F-4G show dose-response to cisplatin under culture environment with control, reduced (medium containing delipid serum or no serum) and increased (control serum supplemented with 1% lipid mixture) lipid content for PEO1 (FIG. 4F), and for SKOV3 (FIG. 4G); n=3. FIG. 4H shows representative bright field and fluorescent images of SKOV3 (n=19 and 20) and SKOV3-cisR cells (n=16) treated with 100 μM fluorescent glucose analog 2-deoxy-2-[(7-nitro-2,1,3-benzoxadiazol-4-yl) amino]-D-glucose (2-NBDG) for 2 hours after cultured in control or reduced lipid content medium (delipid serum) for 24 hours; scale bar: 50 μm. FIG. 4I shows quantified fluorescent signal intensity for FIG. 4H; P=0.024. FIG. 4J represents relative mRNA expression level of CD36, FATP1-6, FABP4-5, and FABP PM in OVCAR5 and OVCAR5-cisR cells; n=2 for FATP6; n=4 for FABP4 and FATP4; n=3 for other genes; n represents biological replicates. FIGS. 4K-4L show relative mRNA express levels of FABP5 (FIG. 4K) and FABP(PM) (FIG. 4L) in OVCAR5 and OVCAR5-cisR cells; the results are shown as means+SD; n=4 biological replicates. P=0.0037 and 0.0018. FIG. 4M shows relative mRNA express level of FABP5 in PEO1 (n=4) and PEO4 (n=5) cells; P=0.012. FIG. 4N shows relative mRNA express level FABP5 and FABP(PM) in OVCAR5 cells treated with cisplatin for 0, 6, 12 or 24 hours; n=3. P=0.00016, 2.4×$10^{-6}$, 0.00037, 0.0069, 0.00037 and 0.052. FIGS. 4O-4P show relative mRNA expression levels of GLUT1 in SKOV3 and SKOV3-cisR cells (FIG. 4O) (n=8. P=0.0089), and in OVCAR5 cells treated with cisplatin for 0, 6, 12 or 24 hours; n=3 (FIG. 4P). FIGS. 4Q and 4S show representative bright field and SRS images of SKOV3 and SKOV3-cisR cells fed with PA-$d_{31}$ (FIG. 4Q) and OA-$d_{34}$ (FIG. 4S) in various concentrations for 6 h; scale bar: 20 μm. FIGS. 4R and 4T show quantitative analysis of SRS signal of C-D bonds in PA-$d_{31}$ (FIG. 4R) or OA-$d_{34}$ (FIG. 4T) fed SKOV3 and SKOV3-cisR cells by mean intensity; n=38, 33, 21, 37, 35, 35, 42, and 23. P=2.2×$10^{-7}$, 0.0016, and 0.019. Data in bar charts FIGS. 4D, and 4J, 4M, 4O, and 4P are presented as means+SD. Data in dose-response curveS FIGS. 4F and 4G are presented as mean±SD. For box plots FIGS. 4I, 4R, and 4T, the bound of outer box indicates 25% to 75% of data; inner box indicates mean; lines represent medium; whiskers indicate SD; circles indicate maxima and minima of data. All statistical significance was analyzed using one-sided Student's t test. *P<0.05, P<0.01, and *P<0.001. FIG. 4U presents representative bright field and SRS images of OVCAR5-cisR cell after fatty acid (FA) transporter inhibitor BMS309403 (BMS) treatment at 10 μM for 24 hours during concomitant incubation with 100 μM PA-$d_{31}$ for 6 hours (BMS inhibits FA uptake and sensitizes OC cell to cisplatin treatment). FIG. 4V shows quantification of C-D SRS signal intensity for FIG. 4U; n=9 and 8. P=0.0026. FIG. 4W is representative bright field and SRS images of OVCAR5-cisR cell after FA transporter inhibitor BMS treatment at 5 μM, 10 μM or 20 μM for 24 hours with the incubation of 100 μM PA-d31 for 6 hours; scale bar: 20 μm. n=6, 5, 6 and 6 technical replicates. FIG. 4X shows quantification of C-D SRS signal intensity from OVCAR5-cisR after treatment with BMS at 5 μM, 10 μM, or 20 μM for 24 hours during concomitant incubation of 100 μM PA-d31 for 6 hours; data are presented as means+SD; n=6, 5, 6 and 6 technical replicates; one-sided Student's t test; P=0.019, 0.0055 and 0.0056. *P<0.05, P<0.01. FIGS. 4Y-4DD show dose-response to cisplatin with or without supplemental BMS treatment for PEO4 (FIG. 4Y), SKOV3-cisR (FIG. 4Z), and OVCAR5-cisR (FIG. 4AA) cells, as well as PEO1 (FIG. 4BB), SKOV3 (FIG. 4CC) and OVCAR5 (FIG. 4DD) cells. The results in all the dose-response curves are shown as means±SD; n=3 biological replicates. Data in all the bar charts are shown as means+SD. All statistical significance was analyzed using two-sided Student's t test. P<0.01, and ***P<0.001. All scale bar: 20 μm.

Figure 5A:
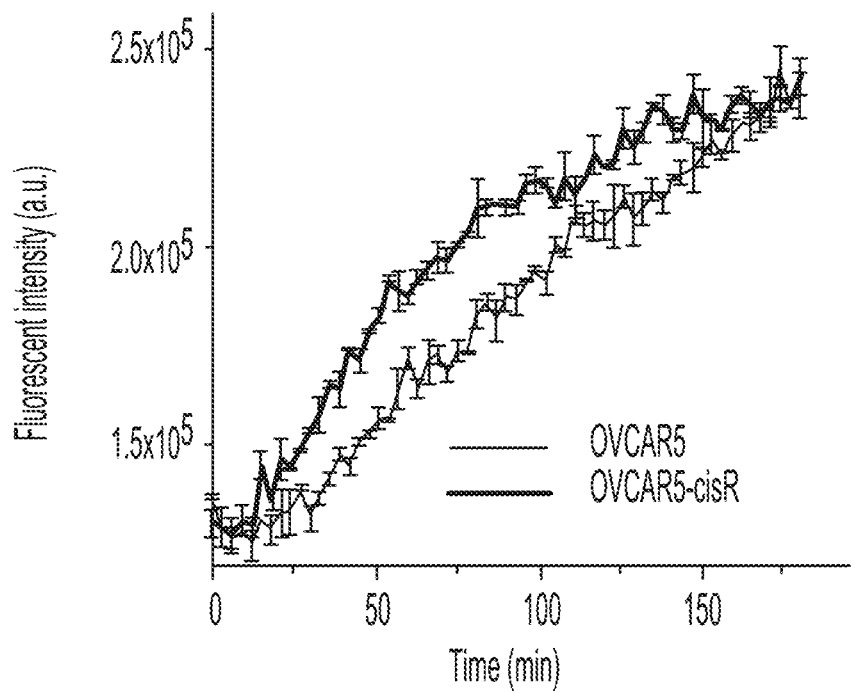
Figure 5B:
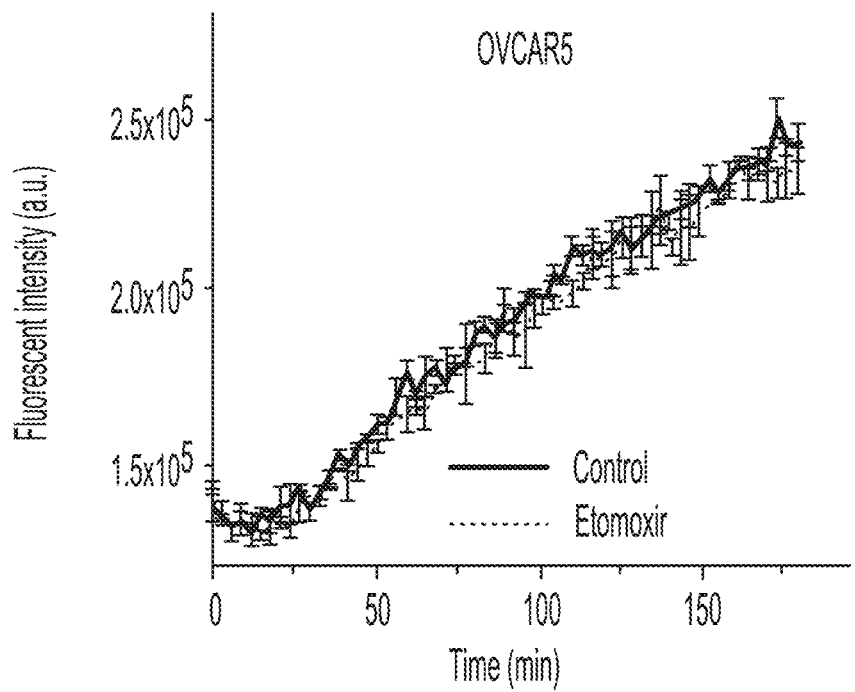
Figure 5C:
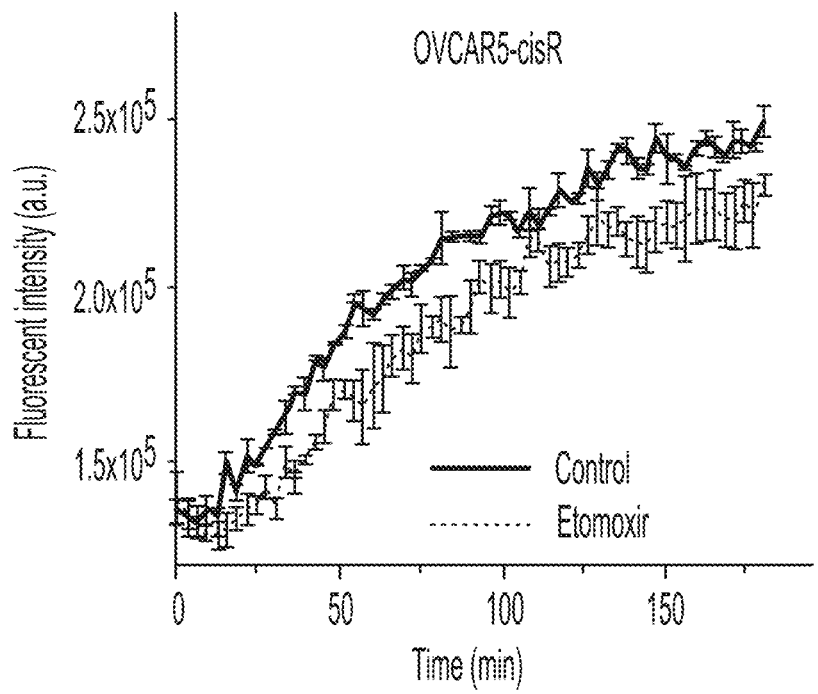
Figure 5D:
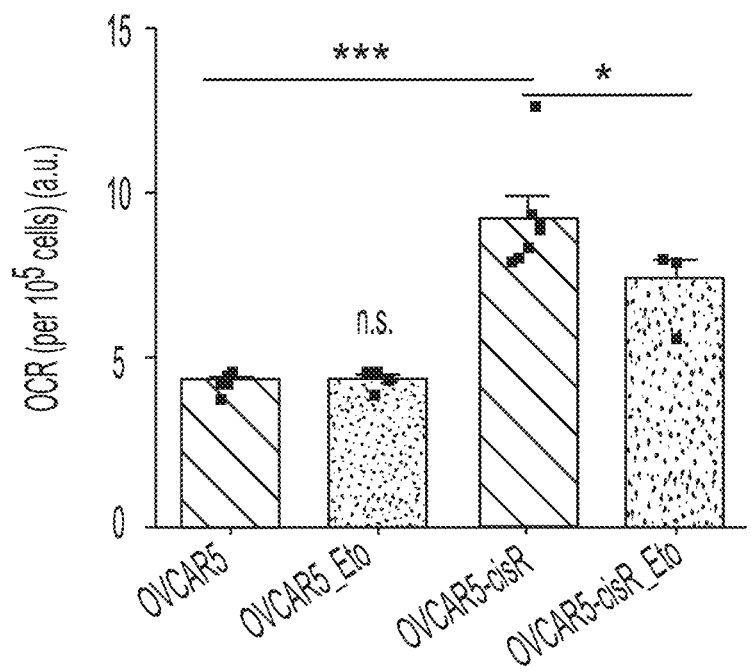
Figure 5E:
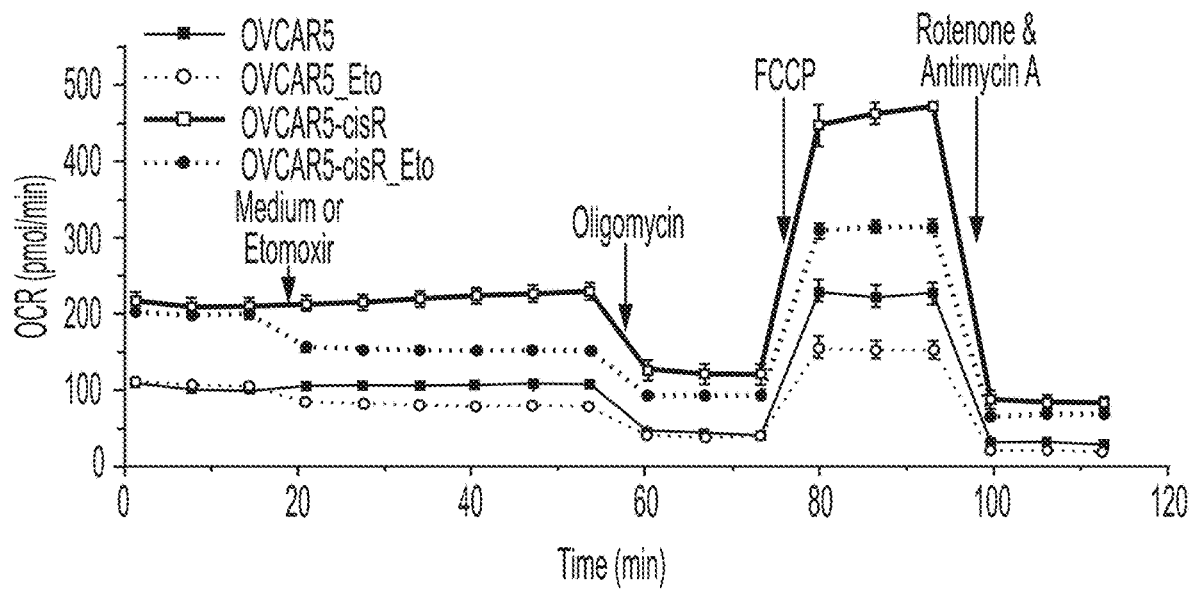
Figure 5F:
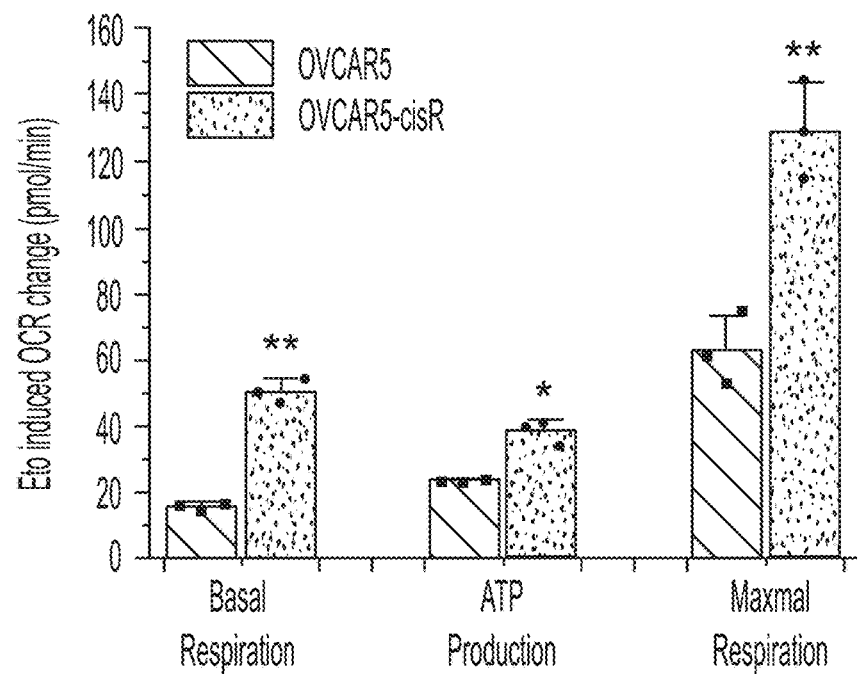
Figure 5G:
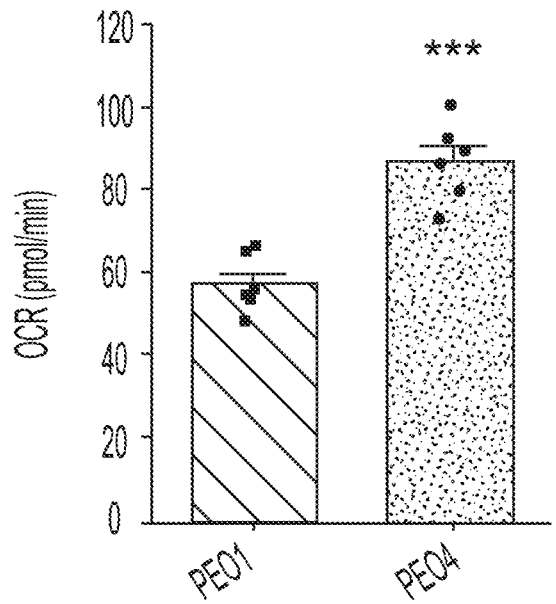
Figure 5H:
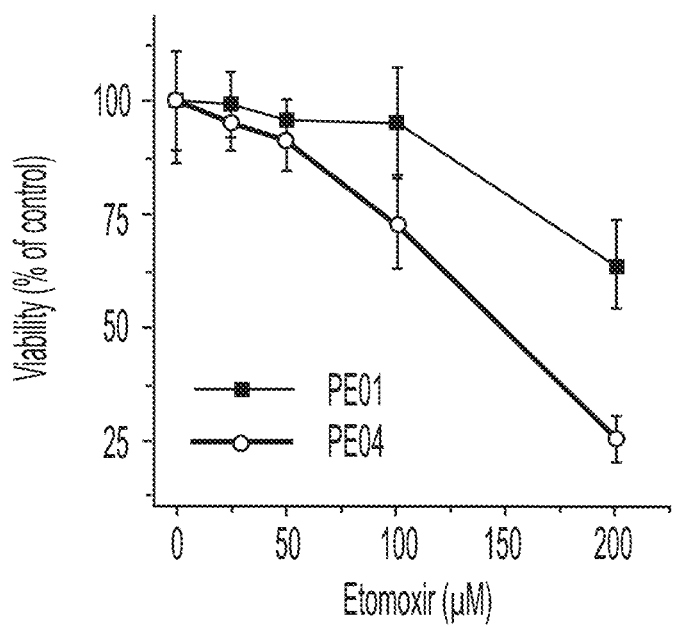
Figure 5I:
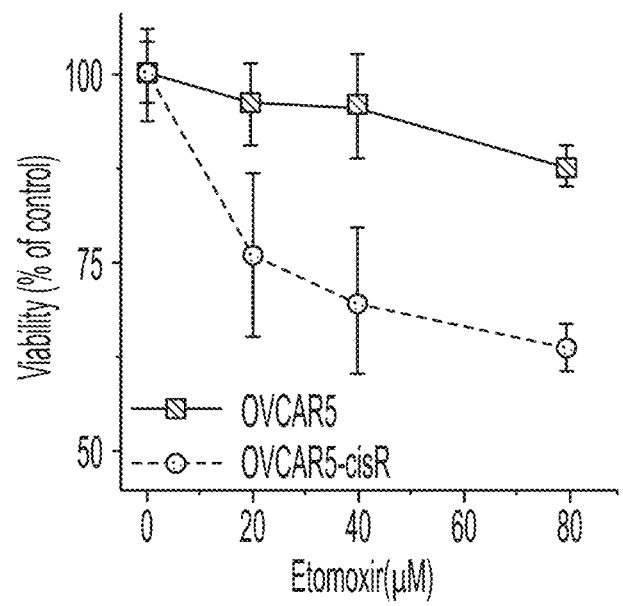
Figure 5J:
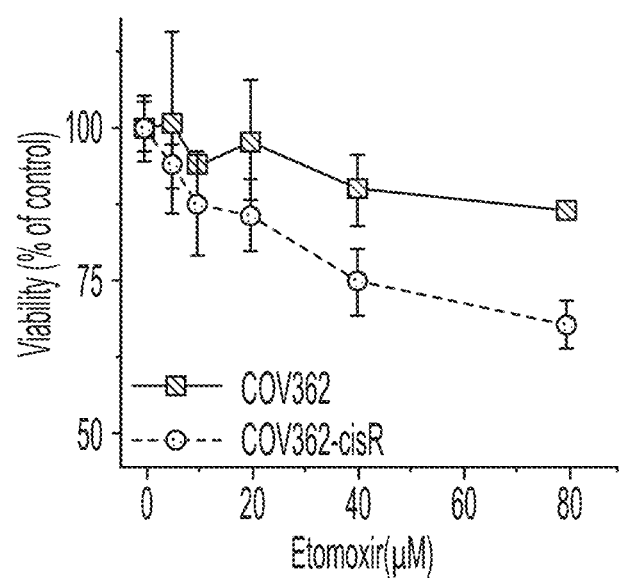
Figure 5K:
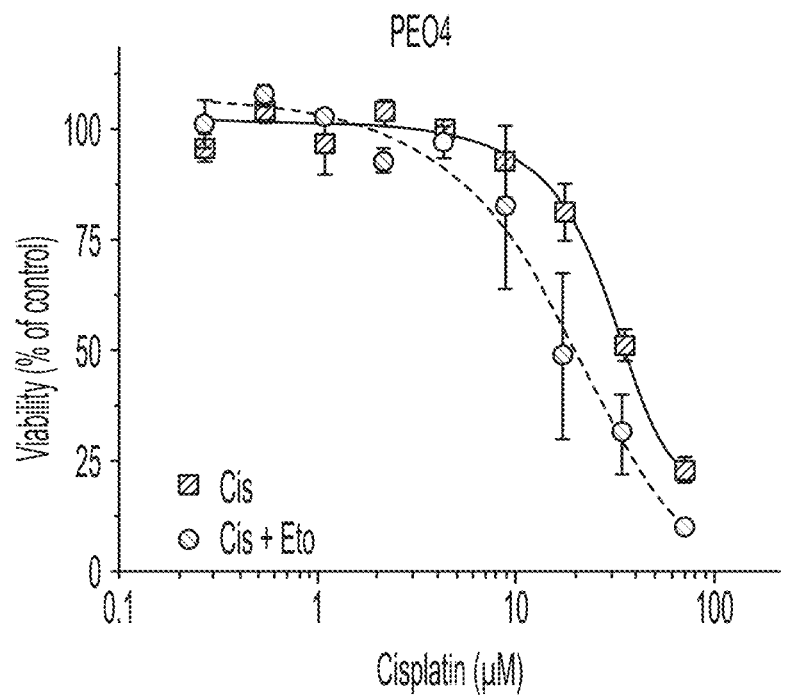
Figure 5L:
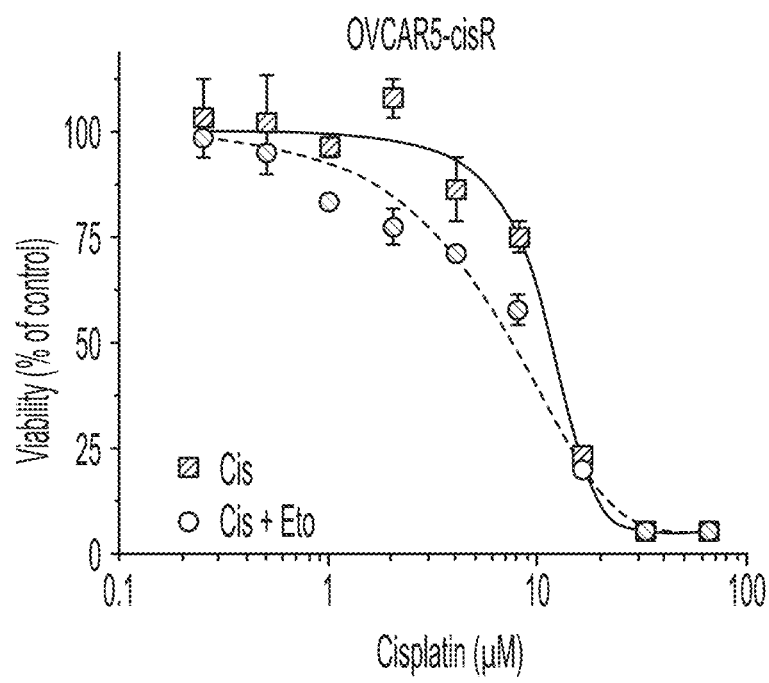
Figure 5M:
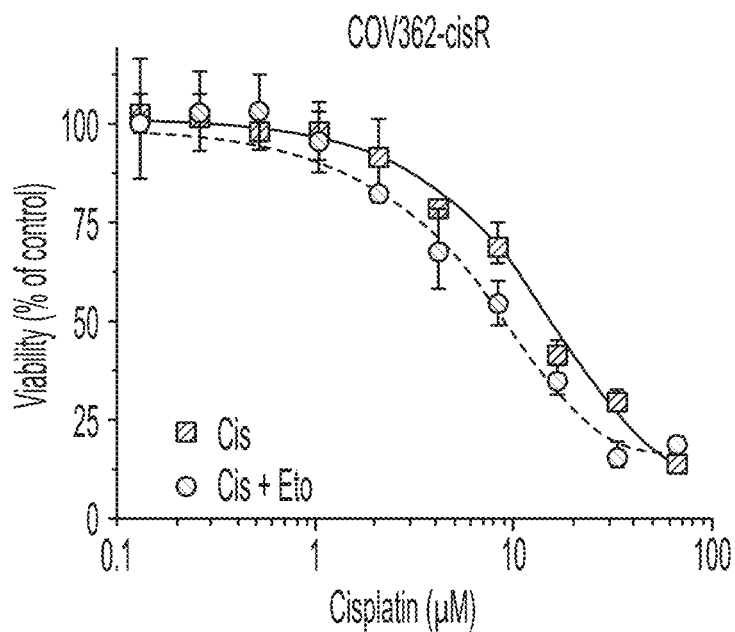
Figure 5N:
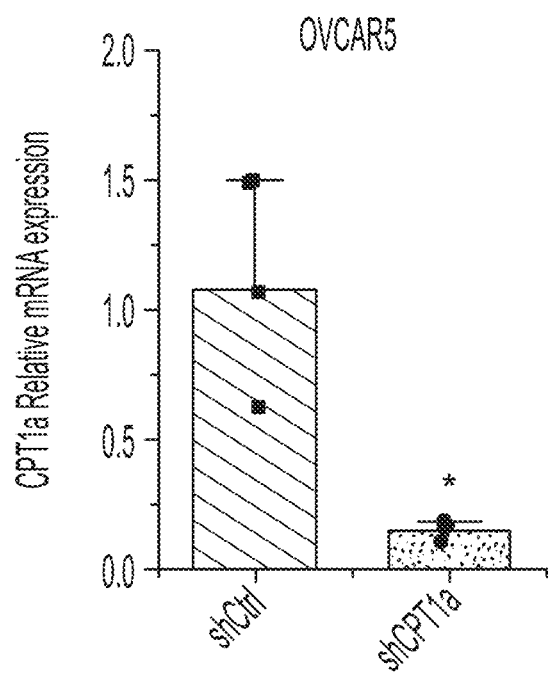
Figure 5O:
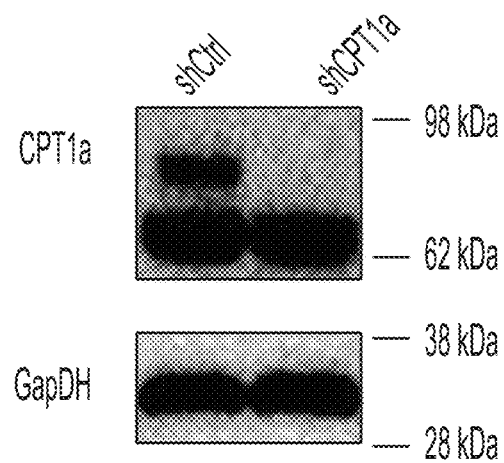
Figure 5P:
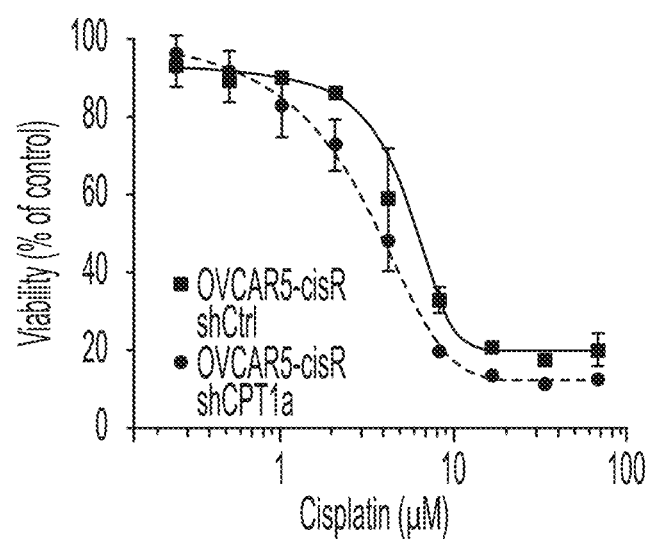
Figure 5Q:
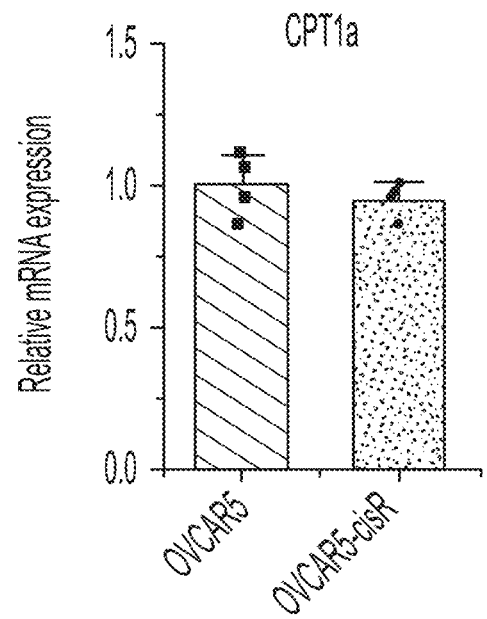
Figure 5R:
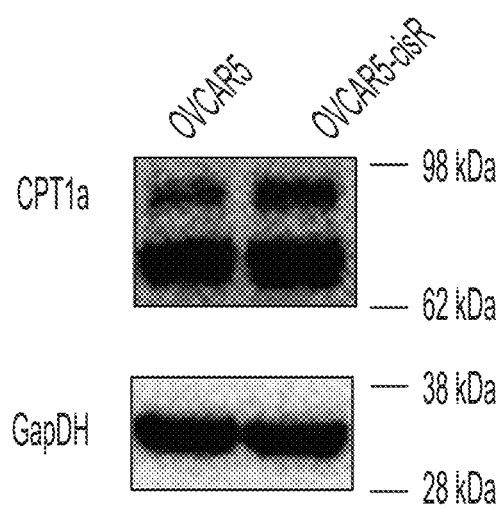
Figure 5S:
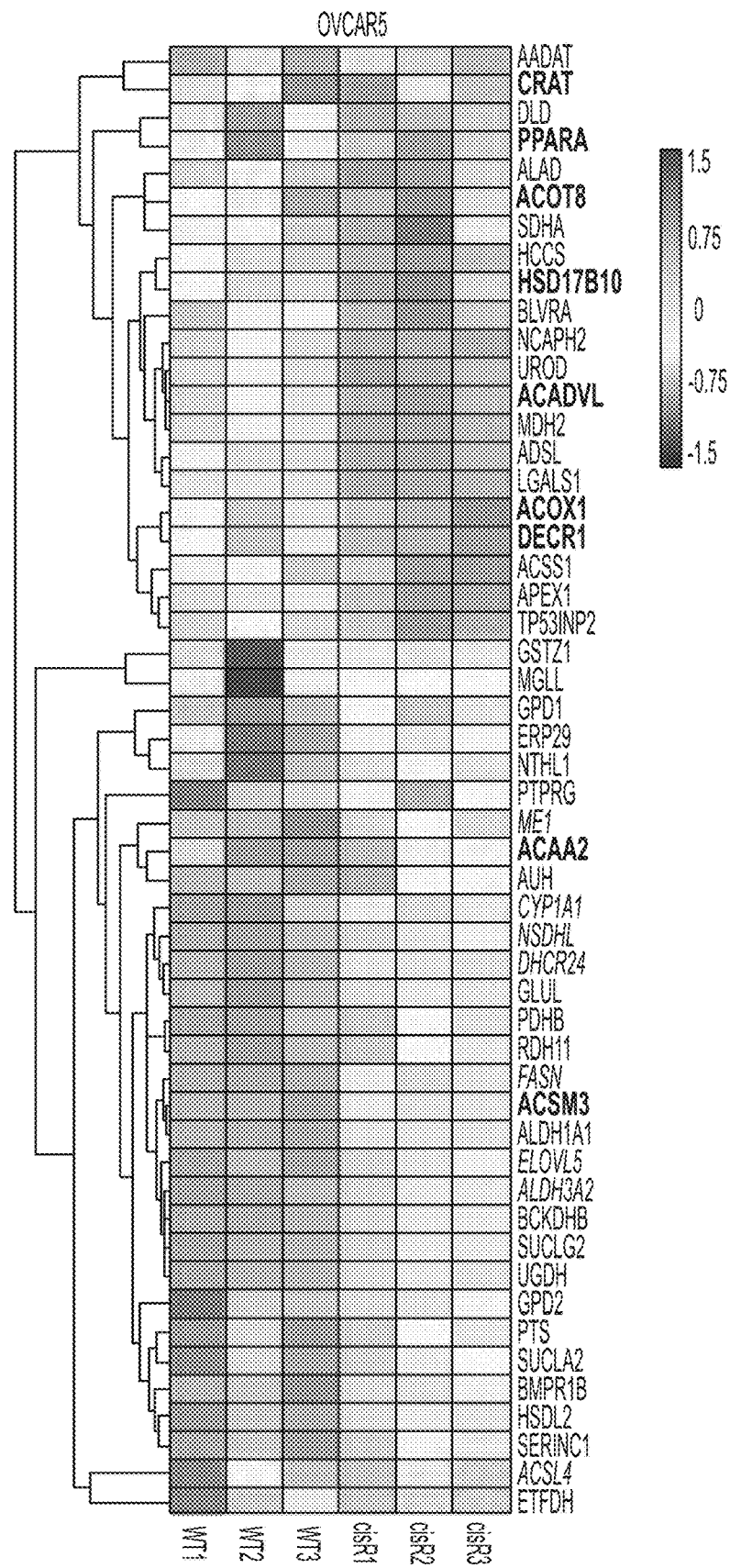
Figure 5T:
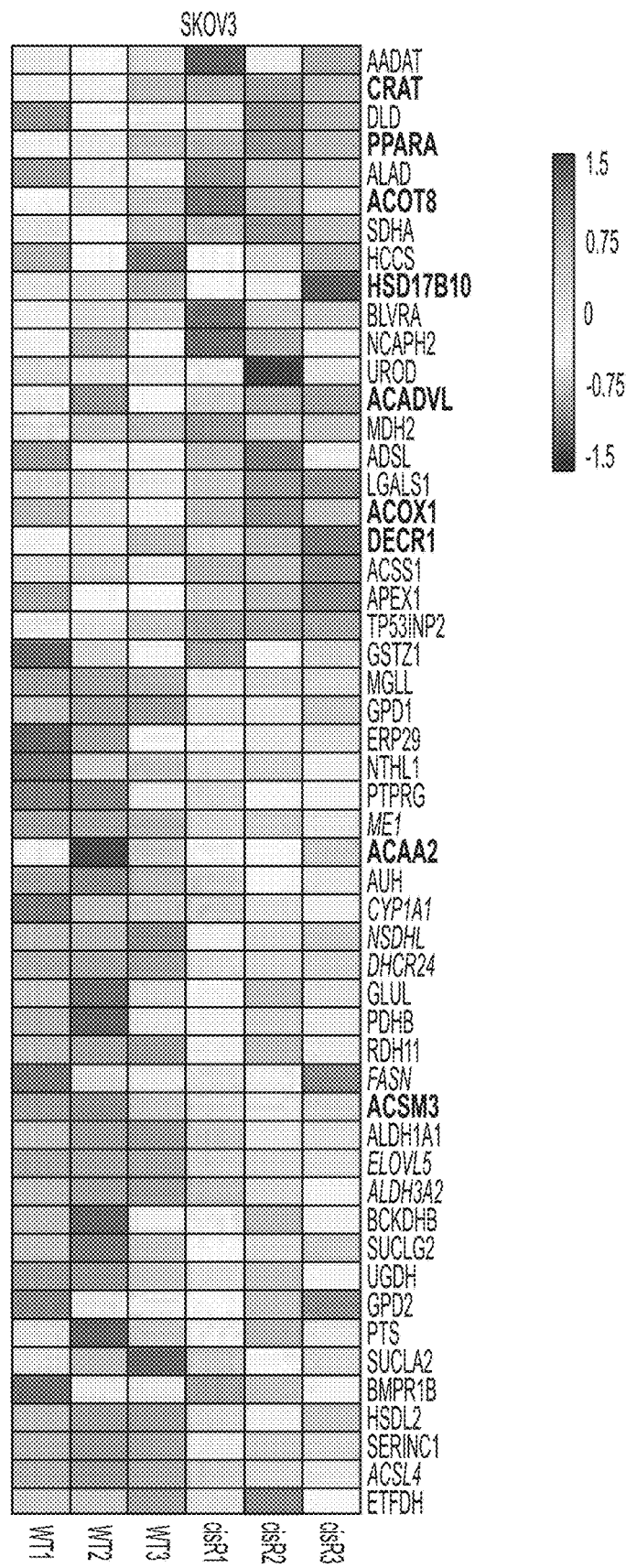
Figure 5U:
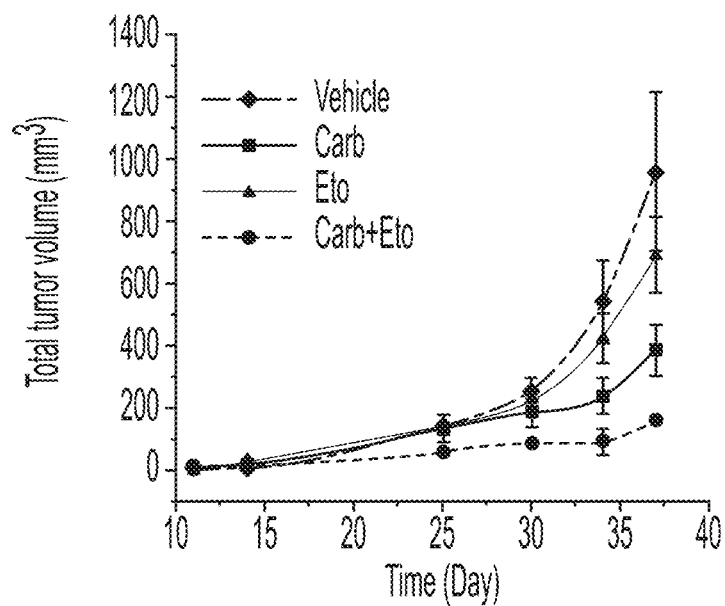
Figure 5V:
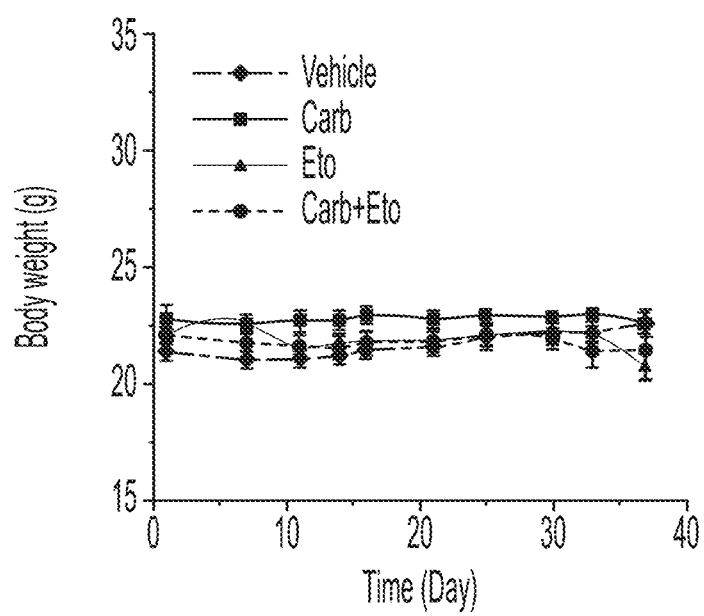

FIGS. 5A-5V show fatty acid uptake contributes to cisplatin resistance by increasing fatty acid oxidation. FIGS. 5A-5C are oxygen consumption curves for OVCAR5-cisR and OVCAR5 over 3 hours (FIG. 5A), and OVCAR5-cisR (FIG. 5B) and OVCAR5 (FIG. 5C) with 40 μM etomoxir treatment over 3 hours; n=4 biological replicates. FIG. 5D shows quantification of oxygen consumption rate (OCR) for OVCAR5 and OVCAR5-cisR cells treated with (n=4) or without (n=6) etomoxir (40 μM) measured by using the extracellular oxygen consumption kit (Abcam); P=0.00044 and 0.041. FIG. 5E is an OCR profile measured with an Seahorse® XF Analyzer (Seahorse Bioscience/Agilent) (Seahorse®) of OVCAR5 and OVCAR5-cisR cells with or without etomoxir treatment, followed by injections of mitochondrial respiration inhibitors oligomycin, carbonylcyanide-p-trifluoromethoxyphenylhydrazone (FCCP), rotenone, and antimycin A (indicated by arrows); n=3 biological replicates. FIG. 5F shows quantified etomoxir induced basal respiration, ATP production, and maximal respiration reduction in OVCAR5 and OVCAR5-cisR cell; data are presented as mean+SD; n=3 technical replicates; two-sided Student's t test; P=0.0021, 0.018 and 0.0046; *P<0.05 and **P<0.01. FIG. 5G shows quantification of OCR for PEO1 and PEO4 cells measured through Seahorse® XF Analyzers; n=6 technical replicates. P=8.9×10$^{-5}$. FIGS. 5H-5J show dose-response to etomoxir for cisplatin resistant cell lines and their parental cell lines including PEO1 and PEO4 (FIG. 5H), OVCAR5 and OVCAR5-cisR (FIG. 5I), and COV362 and COV362-cisR (FIG. 5J). FIGS. 5K-5M show dose-response to cisplatin with or without supplemental etomoxir treatment at 40 μM for PEO4 (FIG. 5K), OVCAR5-cisR (FIG. 5L), and COV362-cisR (FIG. 5M) cells. FIG. 5N presents relative mRNA expression levels of CPT1a in OVCAR5-cisR shCtrl and shRNA targeting CPT1a (shCPT1a) cell; n=3. P=0.033. FIG. 5O is a western blot of CPT1a and GAPDH for OVCAR5-cisR cells transduced with shCtrl and shCPT1a cell; n=3 biological replicates. FIG. 5P is a dose-response to cisplatin for OVCAR5-cisR shCtrl and shCPT1a cell. The data in all the does-response curves FIGS. 5A-5C, 5E, 5H-5M, and 5P are shown as means±SD; n=3. FIG. 5Q shows relative mRNA expression levels for CPT1a in OVCAR5 and OVCAR5-cisR cells; n=4. FIG. 5R is a western blot for CPT1a and GAPDH in OVCAR5 (n=2) and OVCAR5-cisR cells (n=3). The results in bar charts FIGS. 5D, 5N, 5Q are shown as means+SD. For FIGS. 5D, 5G, 5N-5O, and 5Q-5R, statistical significance was analyzed using one-sided Student's t test; *P<0.05. ***P<0.001. n.s. P>0.05. FIGS. 5S and 5T are heatmap charts of lipid metabolism related genes, as analyzed by RNA-sequencing in OVCAR5 (FIG. 5S) and SKOV3 (FIG. 5T) cell line pair; fatty acid oxidation (FAO) related genes are highlighted in red, and lipogenesis related genes are depicted in green. FIG. 5U is a total tumor volume growth curve from day 14 to 37 after tumor cell inoculation for vehicle (n=3), carboplatin (n=3), etomoxir (n=4) and combinational (n=6) treatment groups. FIG. 5V shows mice body weight record since tumor inoculation for vehicle (n=3), carboplatin (n=3), etomoxir (n=4) and combinational (n=6) treatment groups; data for PDX in vivo experiment in FIGS. 5U-5V are shown as means±SEM.

Figure 6A:
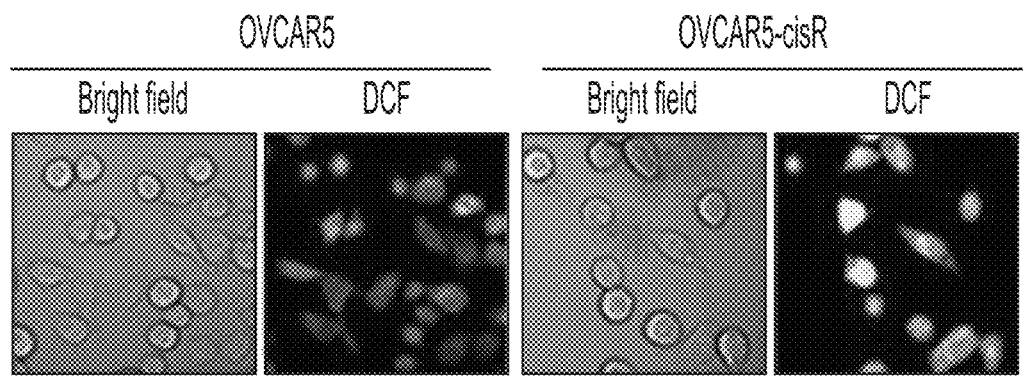
Figure 6B:
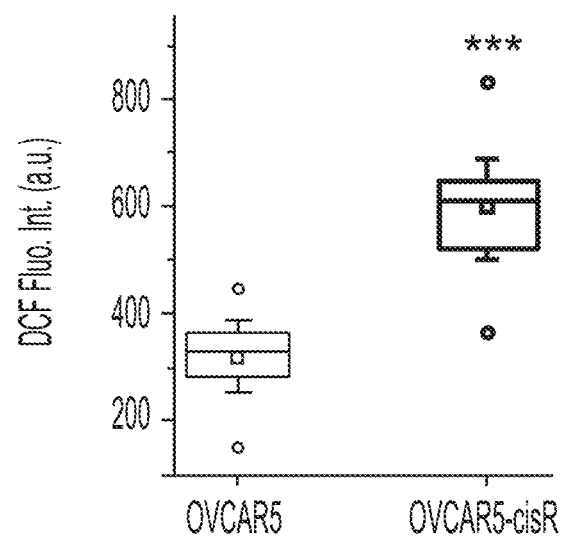
Figure 6C:
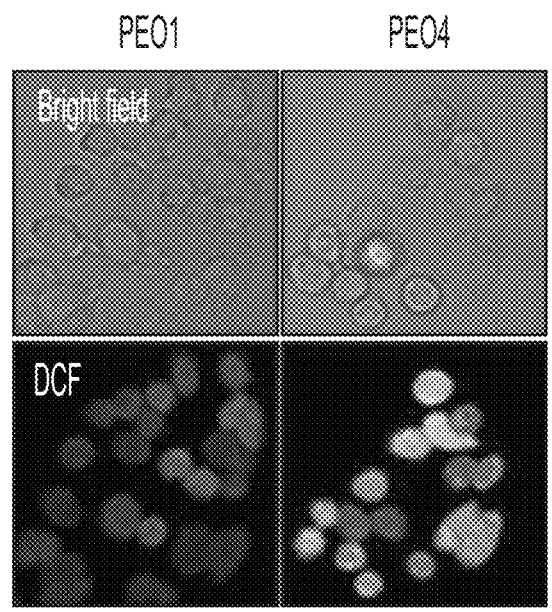
Figure 6D:
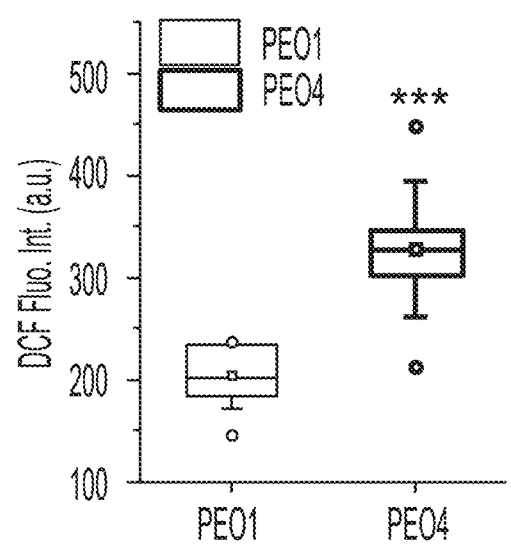
Figure 6E:
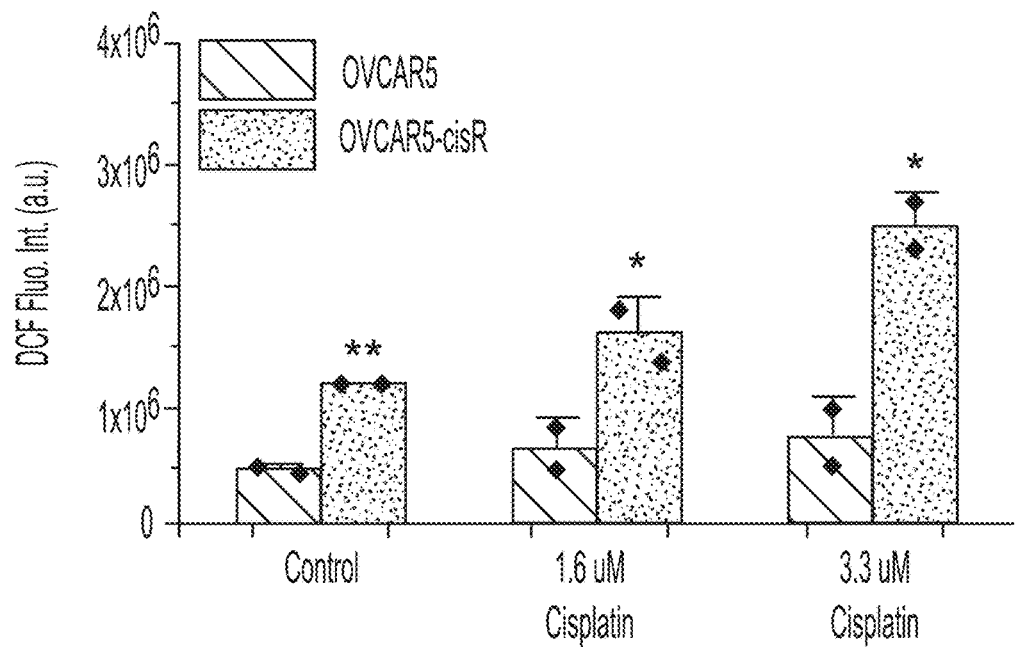
Figure 6F:
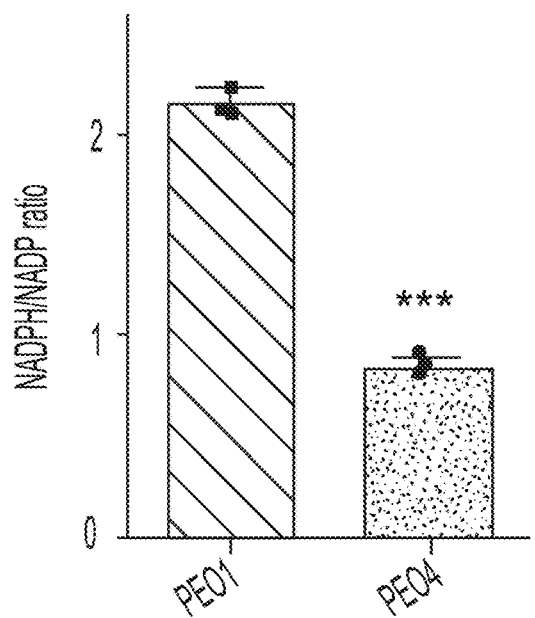
Figure 6G:
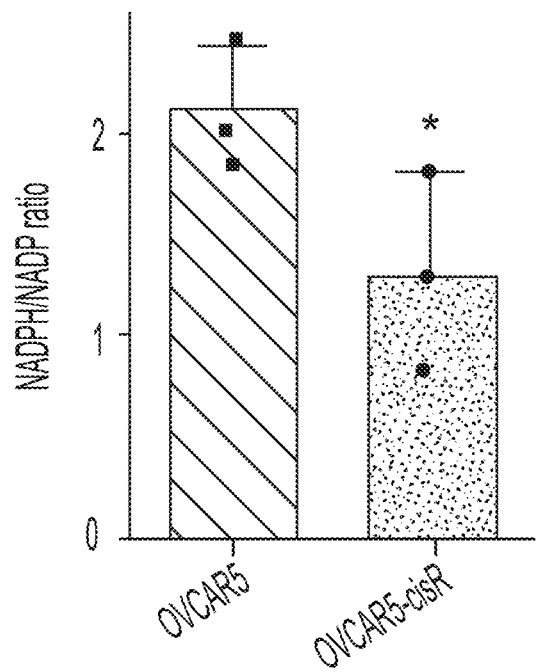
Figure 6H:
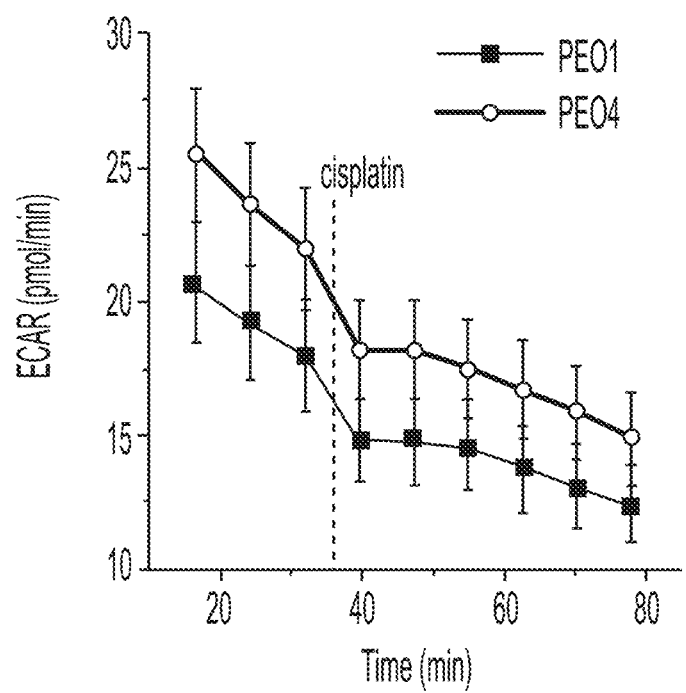
Figure 6I:
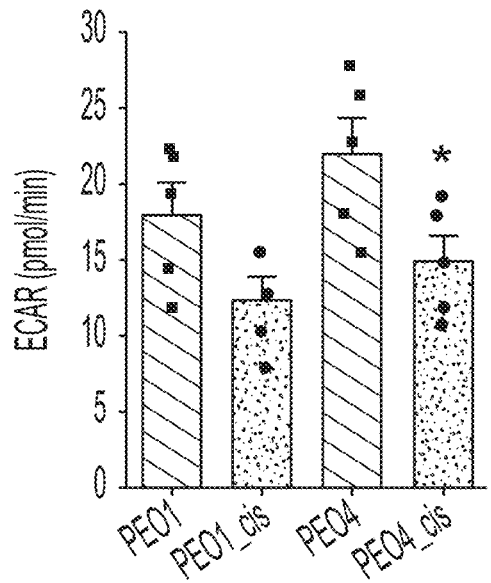
Figure 6J:
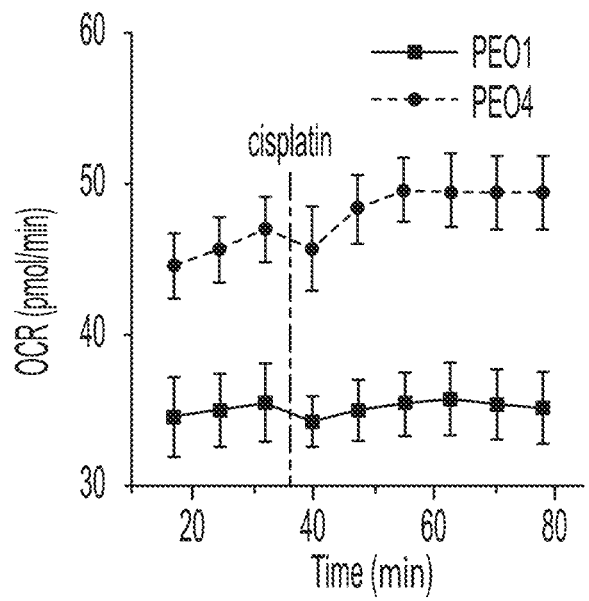
Figure 6K:
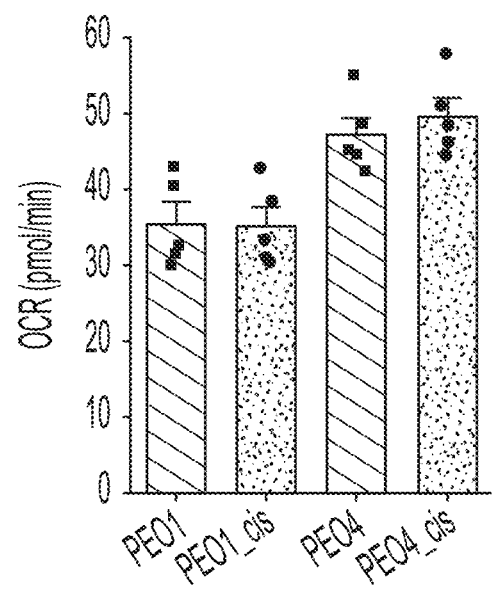
Figure 6L:
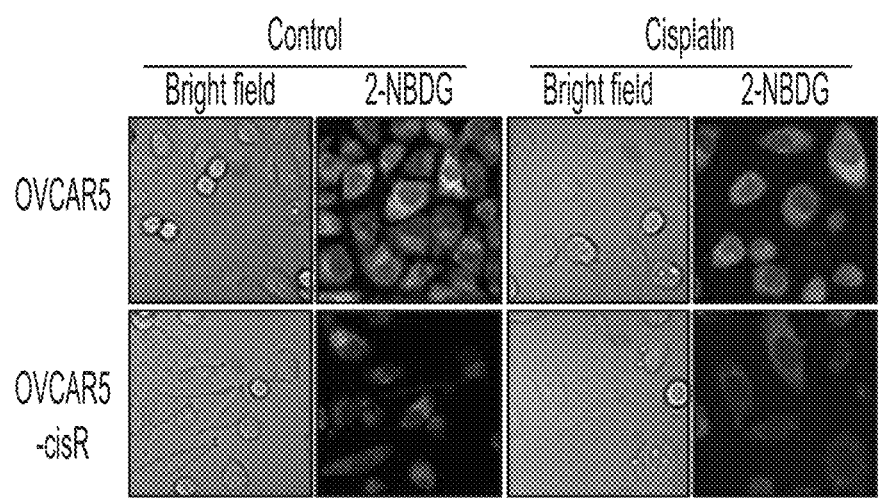
Figure 6M:
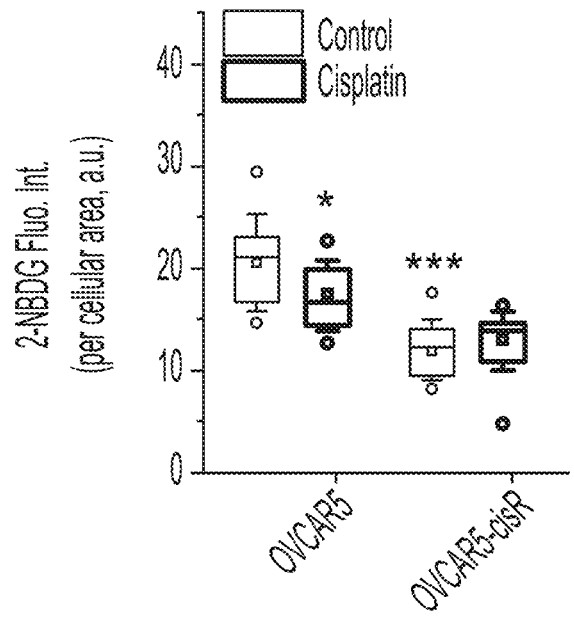
Figure 6N:
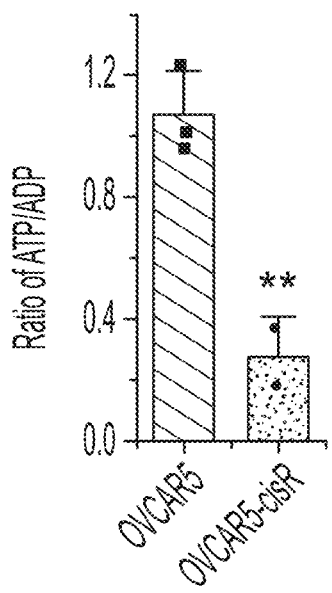
Figure 6O:
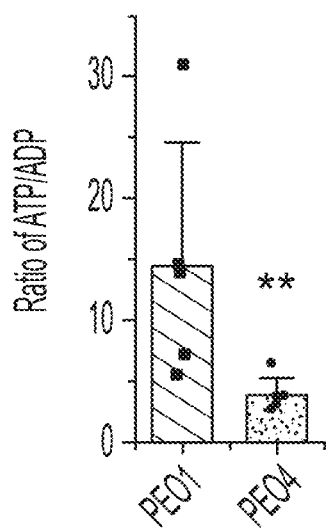
Figure 6P:
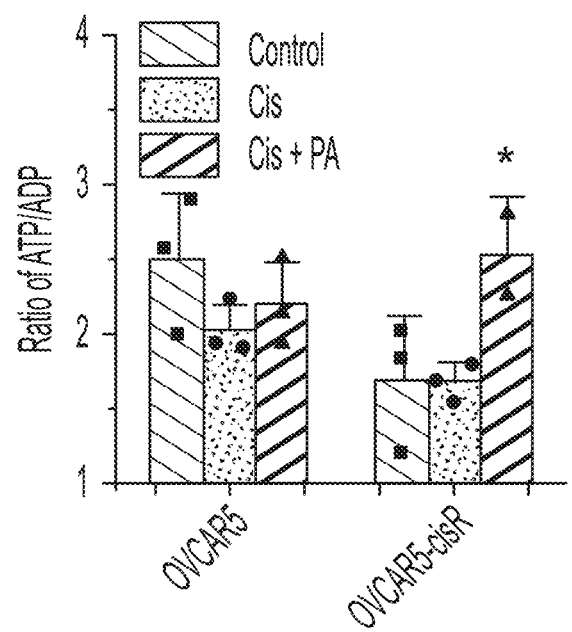
Figure 6Q:
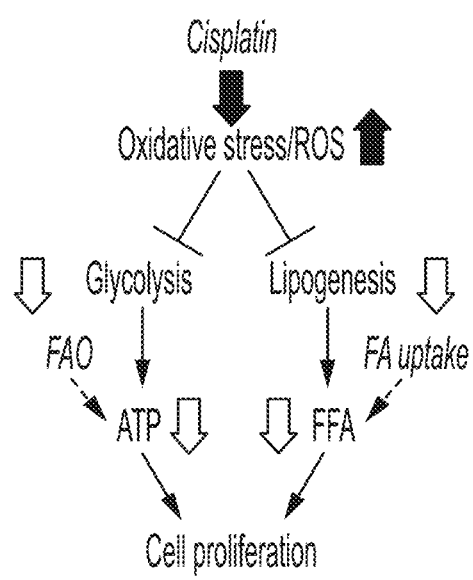

FIGS. 6A-6Q illustrate increased fatty acid uptake and oxidation supports cancer cell survival under cisplatin-induced oxidative stress. FIG. 6A shows representative bright field and fluorescent images of OVCAR5 (n=55) and OVCAR5-cisR (n=49) cells after treated with a fluorescent probe 2',7'-Dichlorofluorescin diacetate (DCFDA) cellular reactive oxidative species (ROS) assay kit. FIG. 6B presents quantification of DCF fluorescent signal intensity for FIG. 6A; P=4.6×10$^{-V}$. FIG. 6C shows representative bright field and fluorescent images of PEO1 and PEO4 cells using the DCFDA cellular ROS assay kit; scale bar: 30 μm. FIG. 6D shows quantification of DCF fluorescent signal intensity for PEO1 and PEO4 cells; bound of outer box indicates 25% to 75% of data; inner box indicates mean; lines represent medium; whiskers indicate SD; circles indicate maxima and minima of data; n=10; P=0.00013. FIG. 6E presents quantification of DCF fluorescent signal intensity of OVCAR5 and OVCAR5-cisR cells with cisplatin treatment at 1.6 μM or 3.3 μM for 24 hours; n=2. P=0.0064, 0.040 and 0.016. FIGS. 6F-6G show quantified NADPH/NADP ratio of PEO1 and PEO4 (FIG. 6F), and OVCAR5 and OVCAR5-cisR (FIG. 6G); n=3. P=2.4×10$^{-5}$ and 0.048. FIG. 6H illustrates extracellular acidification rate (ECAR) profile of PEO1 and PEO4 cells after treatment with 13.2 μM cisplatin measured by Seahorse®; n=5; P=0.041; means±SD. FIG. 6I shows quantification of PEO1 and PEO4 cells' ECAR before and minutes after 13.2 μM cisplatin treatment; n=5. FIG. 6J shows OCR profiles of PEO1 and PEO4 after 13.2 μM cisplatin treatment measured by Seahorse®; means±SD; n=5. FIG. 6K shows quantification of OCR for PEO1 and PEO4 cells before and 30 minutes after treatment with 13.2 μM cisplatin measured by Seahorse®; means+SD; n=5. FIG. 6L shows representative bright field and fluorescent images of OVCAR5 and OVCAR5-cisR cells with 100 μM fluorescent glucose analog 2-NBDG treatment for 2 hours after incubation with 3.3 μM cisplatin for 24 hours. FIG. 6M shows quantified fluorescent signal intensity for FIG. 6L; n=13, 16, 16 and 17. P=0.019 and 8.2×10$^{-7}$. FIGS. 6N-6O show quantified ATP/ADP ratio of cisplatin resistant cell lines and their parental cell lines involving OVCAR5 (n=3) and OVCAR5-cisR (n=2) (FIG. 6N), and PEO1 (n=5) and PEO4 (n=6) (FIG. 6O); n represents biological replicates. P=0.0071 and 0.039. FIG. 6P shows quantified ATP/ADP ratio of OVCAR5 and—OVCAR5-cisR treated with 3.3 μM cisplatin with or without supplement of 100 μM palmitic acid for 6 hours; n=3 biological replicates. P=0.046. FIG. 6Q illustrates the proposed mechanism for cisplatin effect on cellular metabolism and cell proliferation. All Scale bar: 30 μm. For box plots (FIGS. 6B and 6M), the bound of outer box indicates 25% to 75% of data; inner box indicates mean; lines represent medium; whiskers indicate SD; circles indicate maxima and minima of data. Data in bar charts FIGS. 6E-6G and 6N-6P are shown as means+SD. All statistical significance was analyzed using one-sided Student's t test. * P<0.05, P<0.01, and *P<0.001.

Figure 7A:
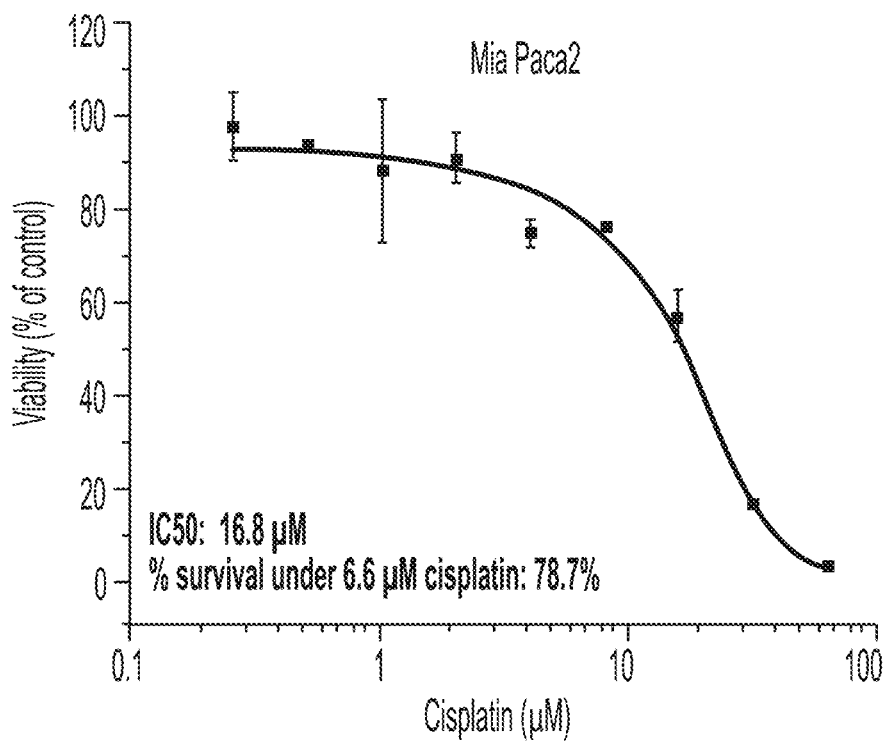
Figure 7B:
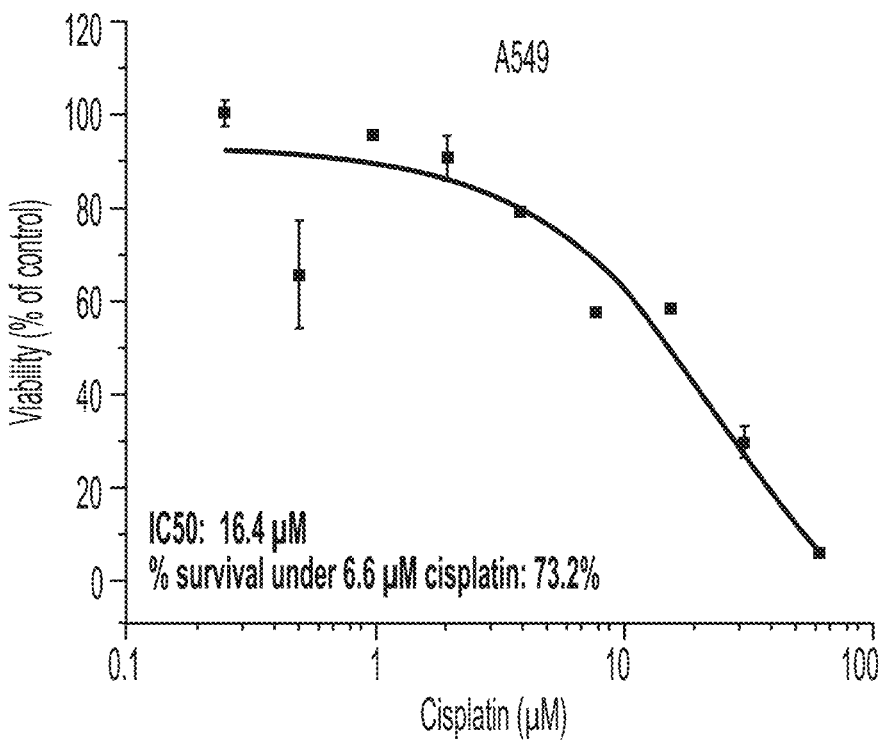
Figure 7C:
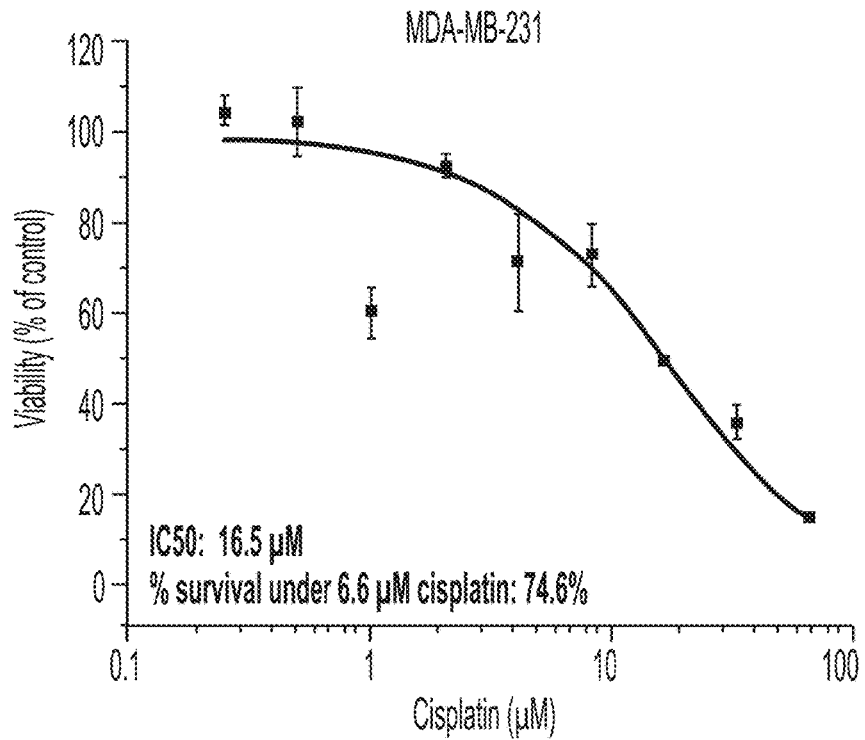
Figure 7D:
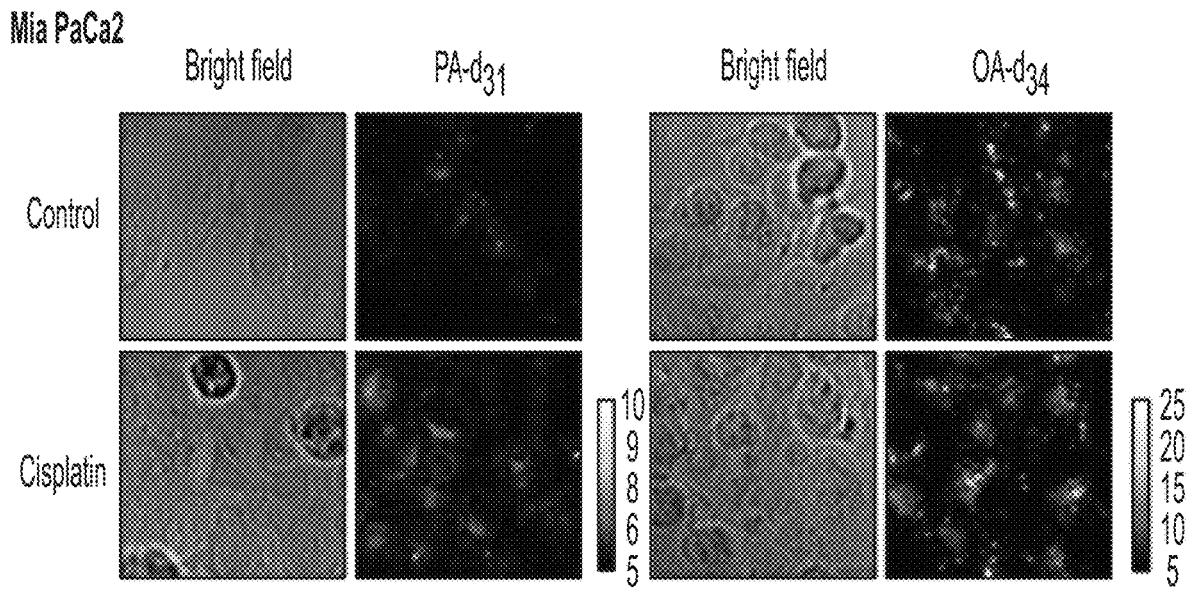

FIGS. 7A-7L show that cisplatin induced fatty acid uptake is a universal metabolic feature in multiple types of cancers. FIGS. 7A-7C show dose-response to cisplatin for Mia Paca2 cells (FIG. 7A), A549 cells (FIG. 7B), and MD-MBA231 cells (FIG. 7C). The data are shown as means±SD; n=3. FIG. 7D presents representative bright field and SRS images of Mia Paca2 cells treated with 6.6 μM cisplatin for 24 hours followed by 100 μM PA-d$_{31}$ or OA-d34 incubation for 6 h.

Figure 7E:
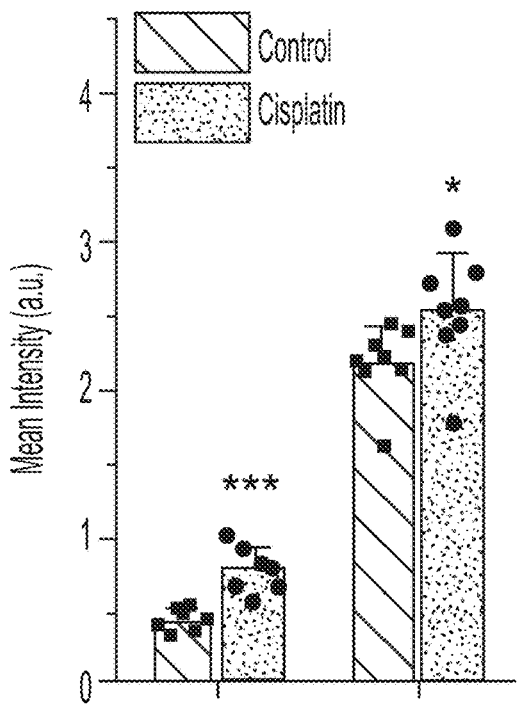
Figure 7F:
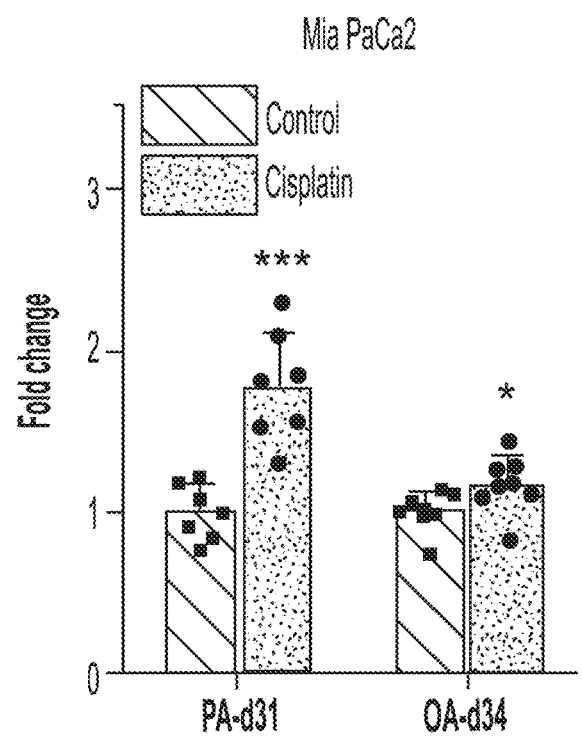
Figure 7G:
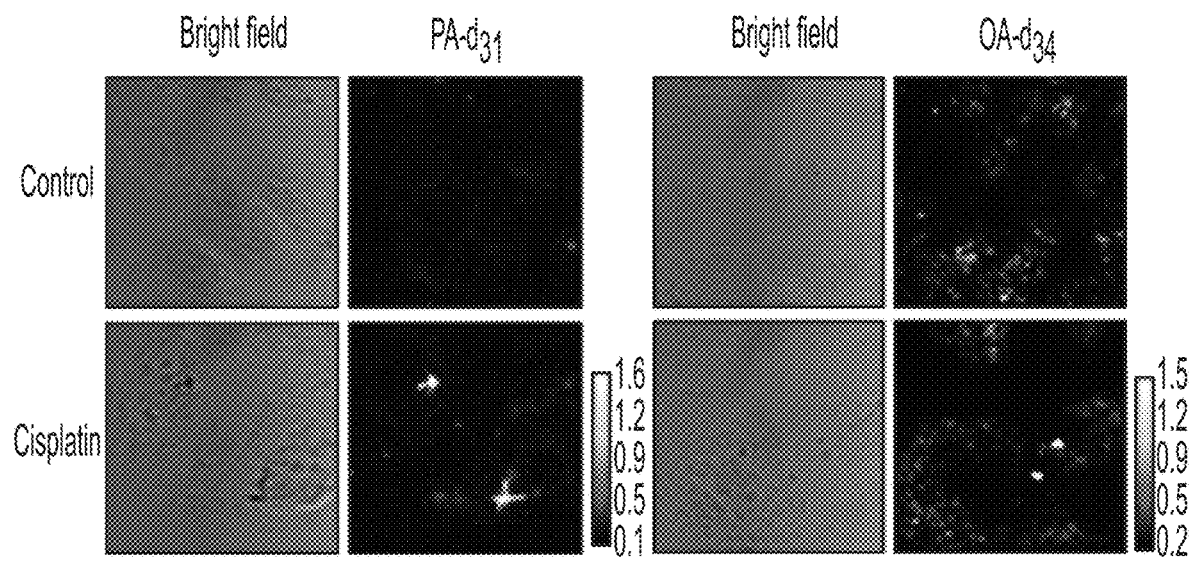
Figure 7H:
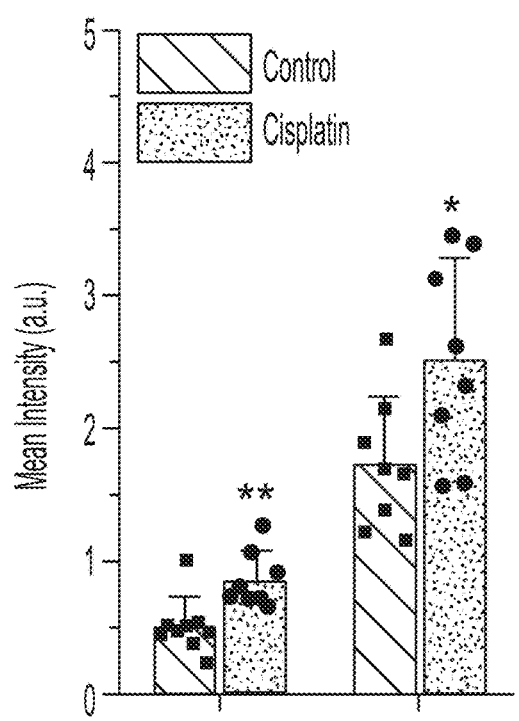
Figure 7I:
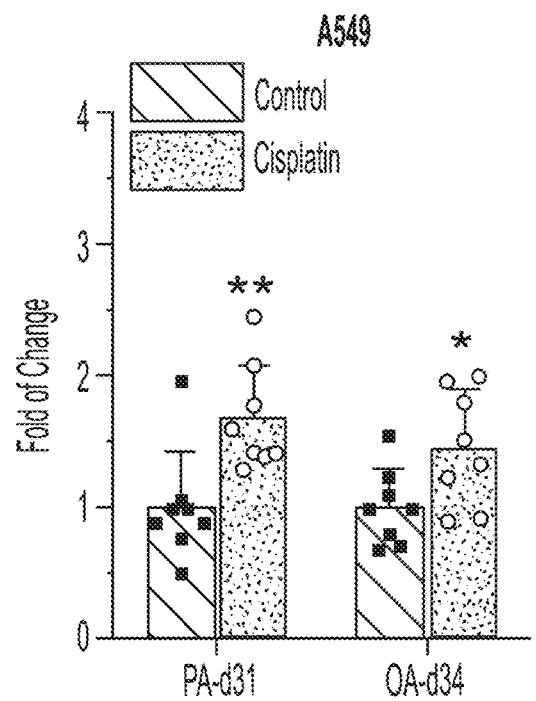
Figure 7J:
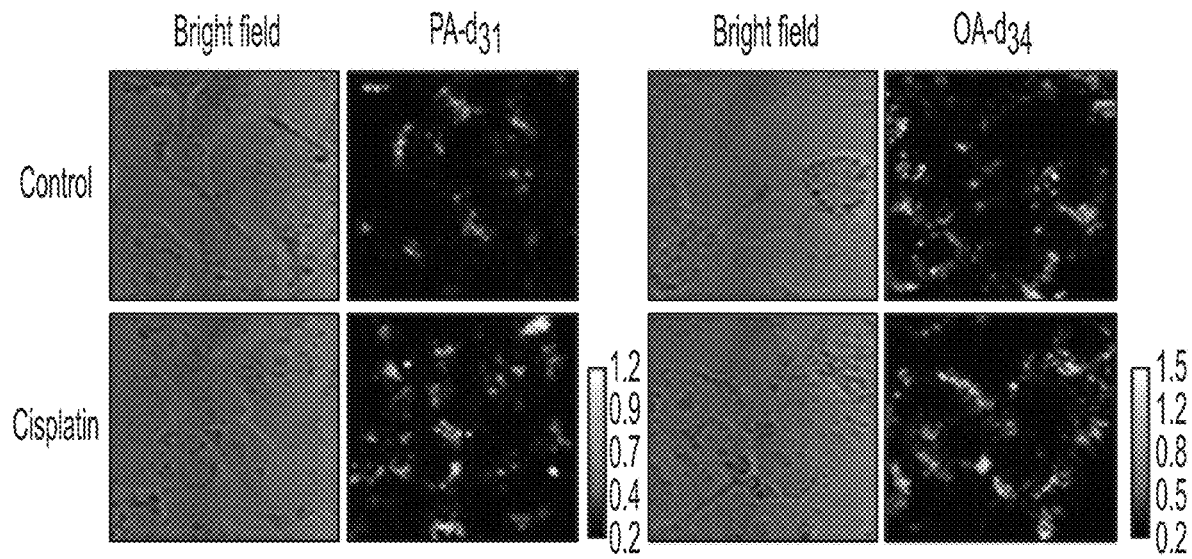
Figure 7K:
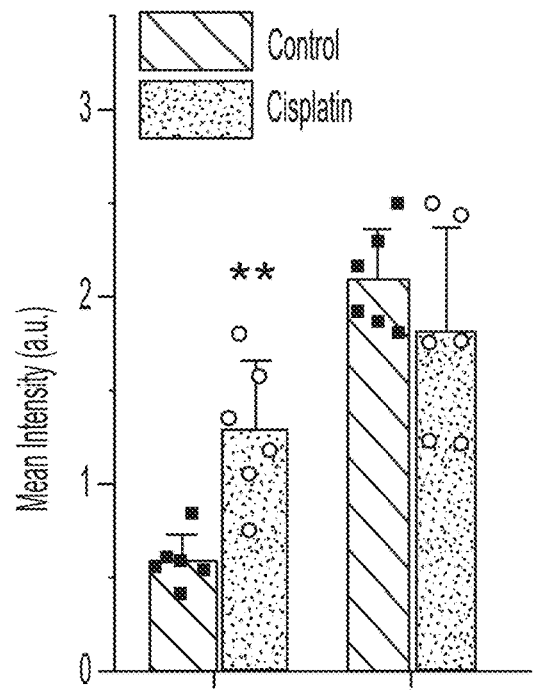
Figure 7L:
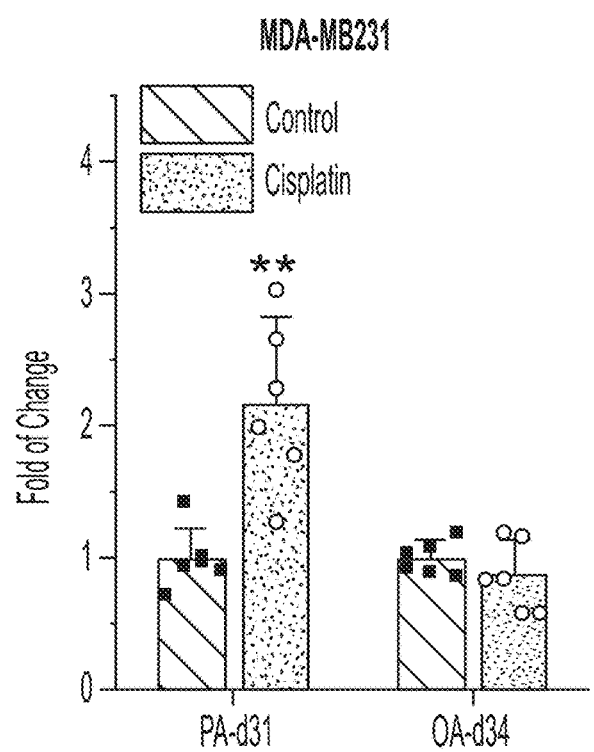

FIG. 7E shows quantitation of C-D signal in Mia Paca-2 cells treated with or without cisplatin by mean intensity; n=7 for PA-d31 and n=8 for OA-d34. P=0.00029 and 0.026. FIG. 7F shows quantitation of C-D signal in Mia Paca-2 cells treated with or without cisplatin by fold of change; (n=7 for PA-d31 and n=8 for OA-d34). FIG. 7G shows representative bright field and SRS images of A549 cells treated with 13.2 µM cisplatin for 48 hours followed by 100 µM PA-d31 or OA-d34 incubation for 6 h. FIG. 7H shows quantitation of C-D signal in A549 cellJ treated with or without cisplatin by mean intensity; n=8. P=0.0031 and 0.016. FIG. 7I shows quantitation of C-D signal in A549 cells treated with or without cisplatin by fold of change; (n=8). FIG. 7J presents representative bright field and SRS images of MDA-MB-231 cells treated with 6.6 µM cisplatin for 24 hours followed by 100 µM PA-$d_{31}$ or OA-$d_{34}$ incubation for 6 h. FIG. 7K shows quantitation of C-D signal in MDA-MB-231 cells treated with or without cisplatin by mean intensity; n=6. P=0.0024. FIG. 7L shows quantitation of C-D signal in MDA-MB-231 cells treated with or without cisplatin by fold of change; (n=6). Data in all bar charts (FIGS. 7E, 7H, 7K) are shown as means+SD. All statistical significance was analyzed using one-sided Student's t test. P=0.00029, 0.026, 0.0031, 0.016 and 0.0024; *P<0.05. P<0.01. *P<0.001. All scale bar: 20 µm.

Figure 8:
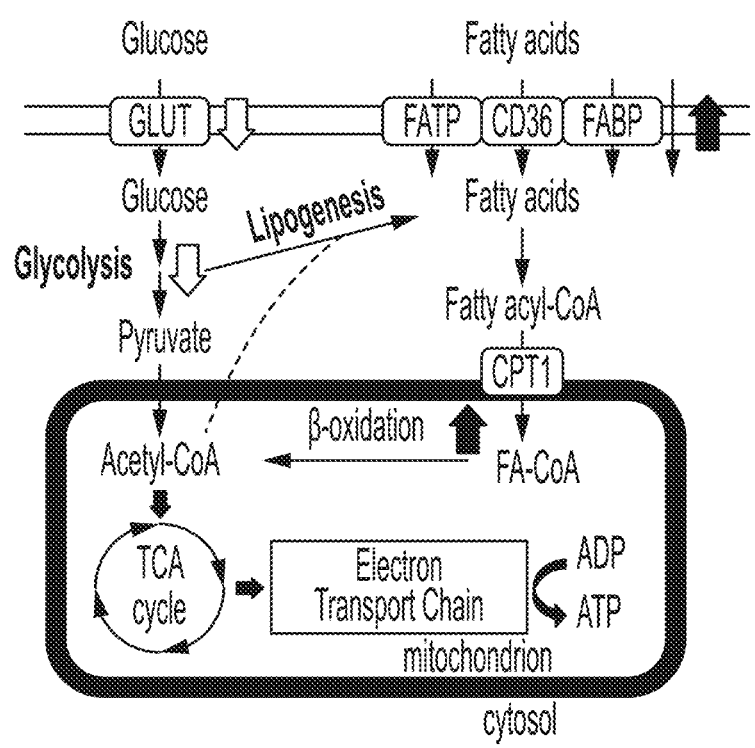

FIG. 8 illustrates cellular metabolism reprogramming from glycolysis to fatty acid oxidation in cisplatin-resistant an ovarian cancer cell.

DETAILED DESCRIPTION

It is to be understood that the descriptive embodiments in this disclosure are not limited to particular methods, reagents, compounds, compositions or biological systems, which can, of course, vary. It is also to be understood that the terminology used herein is for the purpose of describing particular embodiments only, and is not intended to be limiting.

Definitions

Unless defined otherwise, all technical and scientific terms used in this disclosure with the appended claims have the same meaning that is commonly understood by one of ordinary skill in art to which the subject matter pertains. As used in this disclosure and the appended claims, unless specified to the contrary, the following definitions are set forth to provide meaning and scope of the terms and to facilitate the understanding of the disclosure.

The terms "a," "an," "the" and similar references used in the context of the present disclosure include both the singular and the plural, unless indicated or clearly contradicted by context. All methods described herein can be performed in any suitable order unless otherwise indicated or clearly contradicted by context otherwise. The use of any and all examples, or exemplary language (e.g., "such as") is intended merely to illuminate the disclosure and does not pose a limitation on the scope of the invention otherwise claimed.

Furthermore, the term "about," as used herein when referring to a measurable value such as an amount, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the terms "treat", "treatment", and "treating" refer to administering a compound, composition, agent, therapeutic, or a pharmaceutical composition containing the same for therapeutic purposes. As used herein, the terms "compound," "composition," "agent," "therapeutic," or "drug" used or useful for treatment may be used interchangeably.

As used herein, the term "cancer" refers to an abnormal cell that divides without control and can spread or invade into a tissue or spread throughout the body, and a disease or condition with such abnormal cells. The term "cancer" as used herein may be used interchangeably with "tumor," "malignancy," and "malignant neoplasm."

As used herein, the term "benign neoplastic cell" refers to an abnormal cell that divides more than normal, and does not spread or invade into a tissue, and "benign neoplasm" refers to a collection or mass of abnormal cells that divide more than normal. A benign neoplasm is not cancer.

As used herein, the term "immune cell" refers to a cell that is part of the immune system and helps the body fight infection or other disease or condition.

DETAILED DESCRIPTION

This disclosure provides an assay for determining resistance in a target cell or tissue to a therapy associated with cellular stress or perturbation, an assay for determining metabolic reprogramming in a target cell or tissue to a therapy associated with cellular stress or perturbation, and methods of using the assays.

1. Assay for Determining Resistance in a Target Cell or Tissue to Therapy.

Increased aerobic glycolysis is widely considered as a hallmark of cancer. A metabolic reprograming in a cancer cell is known to occur during development of therapeutic resistance. Yet, the mechanism of cellular metabolic reprograming during development of therapeutic resistance to stress and inhibition of aerobic glycolysis is unknown. As disclosed through chemical microscopy or spectroscopy, cells resistant to therapy induced cellular stress are found to exhibit increased uptake of exogenous fatty acids (FAs), accompanied with decreased glucose uptake and de novo lipogenesis. The alteration or change to increased uptake of exogenous fatty acids accompanied with decreased glucose uptake and de novo lipogenesis is an indication of reprogramming from glucose and glycolysis-dependent anabolic and energy metabolism to fatty acid uptake and beta-oxidation dependent anabolic and energy metabolism. Mechanistically, the increased fatty acid uptake facilitates cell survival under therapy induced cellular stress by enhancing energy production through beta-oxidation.

One aspect of the disclosure is an assay for determining resistance in a target cell or tissue to a therapy associated with cellular stress that includes measuring with chemical microscopy or spectroscopy a functional metabolic change in the target cell or tissue, and determining a metabolic index of resistance in the target cell to the therapy. The functional metabolic change is a switch or change from glucose and glycolysis dependent anabolism and energy metabolism to fatty acid uptake and fatty acid oxidation dependent anabolism and energy metabolism. In embodiments, the metabolic index provides a level of resistance in a target cell to a therapy.

A metabolic index incorporates a measurement of glucose derived anabolism and fatty acid uptake and oxidation. The metabolic index is a ratio of an increase in fatty acid uptake and oxidation to a decrease in glucose-dependent anabolism in a target cell, such as a cancer cell. As exemplified, the ratio of fatty acid uptake to glucose derived anabolism is defined as the "metabolic index." The ratio may provide a dimensionless number ranging from 0 to 1, as an index of the general formula fatty acid uptake/(fatty acid uptake+glucose derived anabolism). For example, resistance to cisplatin in cancer cells quantitatively determined by a metabolic index was determined with deuterium labeled palmitic acid-d31 (PA-$d_{31}$) and deuterium labeled glucose-$d_7$ in various cell lines, PA-$d_{31}$/(PA-$d_{31}$+Glucose-$d_7$). The index linearly correlated to the $IC_{50}$ to cisplatin (see, FIG. 3C). Similar metabolic indices were determined from increase of bond signal in various cells (Example 3, FIGS. 3D-3J).

In the embodiments herein, the metabolic index correlates to a level of resistance to the therapy in a target cell or tissue. In embodiments, the metabolic index correlates to resistance to a therapy in the target cell or tissue when a metabolic change is a decrease in glucose and glycolysis dependent anabolism and an increase in fatty acid uptake and fatty acid oxidation dependent anabolism and energy metabolism. In some embodiments, the metabolic index correlates linearly to a level of resistance to the therapy in the target cell or tissue.

In the embodiments herein, the target cell is a cell that may undergo metabolic reprogramming or alteration in response to cellular stress, such as a cancer cell, an immune cell, or a benign neoplastic cell. In the embodiments, the target cell is a cancer cell from any cancer, for example ovarian, prostate, testicular, bladder, pancreatic, lung, breast, esophageal, head, or neck cancer.

Fatty acid oxidation is as an alternative path for energy production, and has been shown to be upregulated in certain conditions, such as under metabolic stress [59]. However, it is less known whether and how fatty acid oxidation is deregulated in drug resistant cells, such as cancer cells. As disclosed herein, cellular stress leads to increased fatty acid uptake and oxidation. For example, oxidative stress depletes intracellular antioxidants, such as NADPH, and thus suppresses de novo lipogenesis that requires such antioxidants. Decreased de novo lipogenesis could result in a lower level of malonyl-CoA, which is an allosteric inhibitor of CPT1, and may trigger higher activity of CPT1 [60, 61]. The decreased de novo lipogenesis is at least partially responsible for the observed increased in fatty acid activity. In the embodiments, the metabolic index further correlates to resistance to the therapy associated with cellular stress in the target cell or tissue when the metabolic change is a decrease in de novo lipogenesis in the target cell or tissue.

In embodiments, measuring with chemical microscopy functional metabolic change comprises measuring glucose and glycolysis derived anabolism in a target cell, measuring fatty acid uptake and oxidation in the target cell, and determining a change from glucose anabolism in the target cell to fatty acid uptake and oxidation energy metabolism. In some embodiments, measuring with chemical microscopy functional metabolic change further comprises measuring de novo lipogenesis in the target cell, and determining a change from glucose and glycolysis dependent anabolism and de novo lipogenesis in the target cell to fatty acid uptake and oxidation energy metabolism.

Another embodiment is an assay for determining resistance in a target cell or tissue resistant to therapy associated with cellular stress or perturbation that includes measuring functional metabolic change in a target cell by measuring with chemical microscopy glucose-derived anabolism in the target cell and fatty acid uptake in the target cell, and determining a ratio of the fatty acid uptake to the glucose anabolism in the target cell to provide a metabolic index of resistance for the target cell. In embodiments, measuring with chemical microscopy functional metabolic change in a target cell comprises measuring with chemical microscopy glucose-derived anabolism in the target cell and measuring with the chemical microscopy fatty acid uptake in the target cell, in which glucose-derived anabolism, and optionally de novo lipogenesis, are decreased and fatty acid uptake is increased. In some embodiments, the metabolic index correlates to a level of resistance to a therapy in the target cell. In some embodiments, the correlation is linear.

In the embodiments herein, the chemical microscopy is any microscopy or spectroscopy that provides for single cell analysis. In the embodiments, the chemical microscopy is Raman scattering microscopy or infrared microscopy. In some embodiments, the Raman scattering microscopy may be spontaneous Raman scattering microscopy, surface enhanced Raman scattering microscopy, or coherent Raman scattering microscopy. Coherent Raman scattering microscopy may be coherent anti-stokes Raman scattering (CARS) or stimulated Raman scattering (SRS) microscopy. SRS microscopy, for example, is a label-free chemical imaging technique that detects the intrinsic chemical bond vibrations. To identify the altered lipid metabolism in resistant cells, a high-throughput single-cell analysis approach was used with large-area hyperspectral SRS scanning (see, [39]). A stack of large-area hyperspectral SRS images was obtained, containing hundreds of individual cells in each field-of-view. (FIG. 1A) An SRS spectrum was extracted at each pixel from the image stack. Then, the hyperspectral SRS images were segmented through a spectral phasor algorithm to generate maps of intracellular compartments corresponding to nuclei and lipids based on the spectrum similarity. The nuclei map was inputted into CellProfiler™ to guide the identification of the edges of each individual cell from the raw whole cell image. After individual cells were outlined, the lipid map was mapped back to the corresponding cells. Finally, quantitative characterization of lipids in terms of integrated intensity, mean intensity, area, and lipid droplet size in each individual cell were performed. Thus, the intrinsic chemical bond vibrations provide indication of altered cell metabolism, for example lipid metabolism, in resistant cells. In some embodiments, the chemical microscopy used in the assay comprises hyperspectral stimulated Raman scattering imaging. In some embodiments, the chemical microscopy comprises hyperspectral stimulated Raman scattering imaging to provide high-throughput vibrational imaging.

In the embodiments herein, infrared microscopy may be mid-infrared photothermal (MIP) microscopy or direct infrared absorption based microscopy, such as fourier-transformed infrared (FTIR) microscopy or quantum cascade laser (QCL) microscopy. In some embodiments, the infrared microscopy is MIP microscopy.

In the embodiments herein, cellular stress or perturbation may originate from a variety of sources that cause a shift in cellular conditions. In some embodiments, cellular stress is oxidative stress, metabolic stress, hypoxic stress, nutrient stress, thermal stress, genotoxic stress, or combinations thereof. In embodiments, the therapy induces cellular stress in the target cell or tissue.

In the embodiments herein, the therapy induces metabolic reprogramming or metabolic alteration or change in a cell. In some embodiments, the therapy is cancer therapy. In the embodiments, cancer therapy is selected from chemotherapy, radiotherapy, immunotherapy, targeted therapy, hormone therapy, light or laser therapy, photodynamic therapy, and combinations thereof. In the embodiments, the cancer therapy is chemotherapy, such as alkylating agent, for example platinum-based agents and nitrosoureas, anti-metabolite, anti-tumor antibiotic, plant alkaloid, for example topoisomerase inhibitors and mitotic inhibitors hormonal agent such as corticosteroids, and biological response modifier. Platinum-based drugs, such as carboplatin and oxaliplatin, are widely used chemotherapy agents for multiple types of cancers, including ovarian, testicular, bladder, head and neck, non-small-cell lung cancer and others. Despite the high response rate following initial treatment, the effects of platinum-based drugs such as cisplatin and carboplatin are limited by severe side effects and high probability of drug resistance development [53, 54]. For example, the major mechanism-of-action of cisplatin is formation of DNA-adducts, which block transcription and DNA synthesis, while at the same time, activate DNA damage response mechanisms and mitochondrial detoxification mechanisms. Apoptosis eventually ensues if DNA lesions are not repaired, and oxidative stress is not buffered. Numerous efforts have been devoted to elucidating the mechanisms of cancer cell resistance to cisplatin. Most of these studies focused on adduct formation and subsequent activation of cell death pathways, for example, reduced formation of DNA-adducts due to altered uptake/efflux, enhanced DNA damage repair, or impaired mitochondrial apoptosis pathway after adduct formation [54]. Other mechanisms of cisplatin resistance have received much less attention. Studies have shown that cisplatin can have another mechanism-of-action by inducing oxidative stress in ovarian [47, 55], prostate [56], and lung cancer [57]. A few studies highlighted an association between metabolic reprogramming and cisplatin resistance. Alterations in glycolysis pathway were associated with cisplatin generated oxidative stress in head and neck squamous cell carcinoma [58]. Lipid droplet production mediated by lysophosphatidylcholine acyltransferase 2 is linked to resistance to oxaliplatin in colorectal cancer [24]. Adipocyte induced FABP4 upregulation was found to mediate carboplatin resistance in ovarian cancer [44]. As disclosed herein, a metabolic alteration or switch is found to occur from glucose dependent anabolic and energy metabolism to fatty acid uptake and fatty acid oxidation in chemotherapy resistant cancer cells, to adapt to chemotherapy-induced oxidative stress.

One embodiment is an assay for determining resistance in a cancer cell resistant to therapy associated with cellular stress that includes measuring with chemical microscopy or spectroscopy a functional metabolic change in the target cell or tissue, and determining a metabolic index of resistance in the target cell to the therapy. In embodiments, measuring with chemical microscopy a functional metabolic change in the target cell or tissue includes measuring with chemical microscopy glucose-derived anabolism in the cancer cell, measuring with the chemical microscopy fatty acid uptake in the cancer cell, and determining a ratio of the fatty acid uptake to the glucose anabolism in the cancer cell to provide a metabolic index of resistance for the cancer cell. In some embodiments, the metabolic index correlates to a level of resistance to a therapy in the cancer cell. In some embodiments, the cancer cell is selected from ovarian, prostate, testicular, bladder, pancreatic, lung, breast, esophageal, head, and neck cancer. In some embodiments, the cellular stress is oxidative stress. In some embodiments, the therapy is cancer therapy. In embodiments, the cancer therapy induces a metabolic alteration in the cell.

In some embodiments herein, the cancer therapy is chemotherapy. In some embodiments, the chemotherapy is a platinum-based agent or therapeutic. In some embodiments, the platinum-based therapy or therapeutic is selected from cisplatin, carboplatin, oxaliplatin, and nedaplatin, and combinations thereof.

Besides fatty acid oxidation, the process of fatty acid uptake represents a target for overcoming drug resistance. The regulation of fatty acid uptake involves multiple and redundant transporters, binding proteins and carrier proteins [42, 43, 45, 62], and fatty acid uptake contributes to several mechanisms significant for tumor survival and growth, including membrane biogenesis, fatty acid pool replenishment, and ER stress prevention [63, 64]. Aside from pointing towards a potential therapeutic strategy for therapy-resistant cancers, ex vivo quantitative metabolic imaging of anaerobic glycolysis, de novo lipogenesis and fatty acid uptake in tumor cells represent a new functional marker for therapy responsiveness in clinical specimens at the single cell level. The conventional methods to determine cell therapy resistance rely on cell viability assays or measurement of various protein markers, which are time-consuming and lack accuracy. The disclosed metabolic imaging approach provides a fast, functional, and quantitative way to determine target cell or tissue resistance based on functional metabolic signatures in resistant cells.

2. Methods of Inhibiting Resistance in a Target Cell to Therapy

Another aspect of the disclosure is use of the disclosed assays in methods of treating or inhibiting resistance in a target cell or tissue to a therapy associated with cellular stress or perturbation. Embodiments include a method of treating or inhibiting resistance in a target cell or tissue to a therapy associated with cellular stress in a subject by performing an assay as disclosed herein to determine a metabolic index of resistance in a target cell or tissue to the therapy, administering at least one inhibitor of fatty acid oxidation to the subject, and administering at least one therapy to the subject. In embodiments, measuring with chemical microscopy a functional change in metabolism comprises measuring glucose and glycolysis dependent anabolism in the target cell, measuring fatty acid uptake oxidation in the target cell, in which glucose and glycolysis dependent anabolism is decreased and fatty acid uptake and oxidation is increased. In embodiments, the metabolic index of resistance in the target cell to the therapy further includes a decrease in de novo lipogenesis.

In embodiments, the metabolic index is a ratio of an increase in fatty acid uptake and oxidation to a decrease in glucose-dependent anabolism in a target cell. An embodiment is a method of treating or inhibiting resistance in a target cell or tissue to a therapy associated with cellular stress comprising measuring with chemical microscopy a functional change in metabolism from glucose and glycolysis dependent anabolism to fatty acid uptake in which glucose and glycolysis dependent anabolism is decreased and fatty acid uptake and oxidation is increased, and determining a metabolic index of resistance in the target cell or tissue to a therapy, administering at least one inhibitor of fatty acid oxidation, and administering at least one therapy. In embodiments, the metabolic index correlates to resistance to the therapy in the target cell or tissue when the functional metabolic change is a decrease in glucose and glycolysis dependent anabolism and an increase in fatty acid uptake and fatty acid oxidation dependent anabolism and energy metabolism. In embodiments, the metabolic index of resistance in the target cell to the therapy further includes a decrease in de novo lipogenesis.

Another embodiment is a method of treating or inhibiting resistance in a target cell or tissue to a therapy associated with cellular stress in a subject comprising measuring with chemical microscopy functional change in metabolism in a target cell or tissue from glucose and glycolysis dependent anabolism to fatty acid uptake in which glucose and glycolysis dependent anabolism is decreased and fatty acid uptake and oxidation is increased, and determining a metabolic index or ratio of a decrease in glucose and glycolysis dependent anabolism and an increase in fatty acid uptake and oxidation indicating resistance in the target cell or tissue to a therapy, administering at least one inhibitor of fatty acid oxidation to the subject, and administering at least one therapy to the subject.

In embodiments, measuring with chemical microscopy functional metabolic change comprises measuring with the chemical microscopy glucose and glycolysis derived anabolism in the target cell, measuring with the chemical microscopy fatty acid uptake and oxidation in the target cell, and determining a change from glucose and glycolysis derived anabolism in the target cell to fatty acid uptake and oxidation energy metabolism.

A further embodiment is a method of treating or inhibiting resistance in a cancer cell to therapy associated with cellular stress in a subject comprising measuring with chemical microscopy glucose-derived anabolism in the cancer cell, measuring with the chemical microscopy fatty acid uptake in the cancer cell, and determining a ratio of the fatty acid uptake to the glucose anabolism in the cancer cell to obtain a metabolic index, administering an inhibitor of fatty acid oxidation to the subject, and administering a therapy to the subject. In the embodiments, the administering may be in any form effective for the treatment.

In some embodiments, the metabolic index correlates to a level of resistance in the cancer cell to a therapy. In some embodiments, the correlation is linear.

In the embodiments, the method further comprises obtaining a cancer cell from the subject to perform the assay. The subject may be any mammal, for example human. The cancer cell can be from any cancer. In the embodiments, the cancer is selected from ovarian, prostate, testicular, bladder, pancreatic, lung, breast, esophageal, head, and neck cancer.

In the embodiments herein, the therapy induces metabolic alteration or change in a cell. In some embodiments, the therapy is cancer therapy. In the embodiments, cancer therapy is selected from chemotherapy, radiotherapy, immunotherapy, targeted therapy, hormone therapy, light or laser therapy, photodynamic therapy, and combinations thereof. In some embodiments, the cancer therapy is chemotherapy selected from an alkylating agent, for example platintim-based agents and nitrosoureas, an anti-metabolite, an anti-tumor antibiotic, a plant alkaloid, for example topoisomerase inhibitors and mitotic inhibitors, a hormonal agent such as corticosteroids, a biological response modifier, and combinations thereof. In some embodiments, the chemotherapy is a platinum-based agent or therapeutic, selected from cisplatin, carboplatin, oxaliplatin, nedaplatin, and combinations thereof. In the embodiments, the administering may be in any form effective for the treatment.

In embodiments, fatty acid oxidation is inhibited in the cancer cell and the therapy induces cellular stress in the cancer cell, thereby inhibiting resistance to the therapy. In embodiments, the at least one inhibitor of fatty acid oxidation is a small molecule inhibitor or a genetic perturbation (e.g., gene deletion, gene overexpression, insertion mutation), or a combination thereof. In embodiments, the inhibitor of fatty acid oxidation is selected from etomoxir, oxfenicine, perhexiline, mildronate, trimetazidine, and combinations thereof.

Collectively, a new means for rapid detection of resistance to therapy at a single cell level, and a new strategy for treating tumors resistant to therapy are disclosed. Through large-area chemical microscopy imaging and subsequent single-cell analysis, a stable, metabolic change or switch is shown from glucose and glycolysis dependent anabolic and energy metabolism to fatty acid uptake and fatty acid beta-oxidation dependent anabolic and energy metabolism. By coupling metabolic flux through isotope labeling and microscopic molecular imaging, resistant cells display increased uptake of exogenous fatty acid, accompanied with decreased glucose uptake and de novo lipogenesis. By incorporating microscopic imaging-based measurements of glucose derived anabolism and fatty acid uptake, a "metabolic index" may be determined, defined as the ratio of fatty acid uptake versus glucose incorporation. The metabolic index correlates to the level of resistance to therapy in target cells, such cancer cells, and in primary human cells. This correlation demonstrates the potential of using microscopy or spectroscopy imaging for rapid detection of resistance to therapy in cancer cells ex vivo.

Mechanistically, resistant cells display higher fatty acid oxidation rate, which supplies additional energy and promotes cell survival under cellular stress. Blocking fatty acid oxidation by a small molecule inhibitor or genetic perturbation in combination therapy, for example platinum-based treatment, synergistically suppresses cell proliferation in vitro and growth of a patient-derived xenograft model in vivo. This further provides new treatment options for patients with tumors resistant to therapy such as platinum-based therapy, for example cisplatin-resistant cells, by targeting the fatty acid oxidation pathway.

The described technology is further illustrated by the following examples which in no way should be construed as being further limiting.

EXAMPLES

Materials and Methods

The described research complied with all relevant ethical regulations. Animal studies were approved by the Institutional Animal Care and Use Committee (IACUC) at Northwestern University and were performed in the Developmental Therapeutics Core (DTC) of the Lurie Cancer Center.

Glucose-$d_7$, palmitic acid-$d_{31}$ (PA-$d_{31}$), and oleic acid-$d_{34}$ (OA-$d_{34}$) were purchased from Cambridge Isotope Laboratory. 17-Octadecynoic Acid (ODYA), BMS309403, cisplatin, and etomoxir were purchased from Cayman Chemicals.

For treatment with cisplatin, 3.3 μM was used as the final concentration, unless otherwise specified.

Cell Lines

Ovarian cancer cell lines used in the methods include SKOV3, PEO1, OVCAR5, and COV362, and their cisplatin-resistant counterparts include SKOV3-cisR, PEO4, OVCAR5-cisR, and COV362-cisR. SKOV3 (Cat #: HTB-77), Mia Paca2 (Cat #: CRL-1420), MDA-MB-231 (Cat #: CRM-HTB-26) and A549 (Cat #: CCL-185) cells were purchased from the American Type Culture Collection (ATCC, Manassas, VA). PEO1 (Cat #: 10032308) and PEO4 (Cat #: 10032309) were purchased from Sigma Aldrich. OVCAR5 cells were a generous gift from Dr. Marcus Peter, Northwestern University, and COV362 cells were from Dr. Kenneth Nephew, Indiana University. All cell lines were authenticated and tested to be mycoplasma negative. Mia Paca2 and A549 are in the list of known misidentified cell lines maintained by the International Cell Line Authentication Committee, while their authentication was performed by ATCC through STR profiling. The resistant cell lines SKOV3-cisR, COV362-cisR, and OVCAR5-cisR were generated by treatment with 3 or 4 repeated or increasing doses of cisplatin for 24 hours. Surviving cells were allowed to recover for 3 to 4 weeks before receiving the next treatment. Changes in resistance to platinum were estimated by calculating half maximal inhibitory concentration ($IC_{50}$) values [40]. PEO1, PEO4, OVCAR5, and OVCAR5-cisR cells were cultured in RPMI 1640 medium supplemented with 2 mM L-glutamine, 10% FBS and 100 units/mL penicillin/streptomycin. SKOV3, SKOV3-cisR, COV362, and COV362-cisR and Mia Paca2 cells were cultured in high-glucose DMEM medium supplemented with 10% FBS and 100 units/mL penicillin/streptomycin. MDA-MB-231 and A549 cells were cultured in Leibovitz's L-15 medium and Kaighn's Modification of Ham's F-12 Medium respectively supplemented with 10% FBS and 100 units/mL penicillin/streptomycin. For CPT1a knockdown cell lines development, cells were transfected with CPT1a or control shRNA lentiviral particles (Sigma Aldrich) Sigma Aldrich, TRCN0000036282) for 48 hours and selected by 1 μg/ml puromycin for one week. All cells were cultured at 37° C. in a humidified incubator with 5% $CO_2$ supply.

Primary Human Cells

De-identified high grade serous ovarian tumors (HGSOC) and malignant ascites fluid specimens from ovarian cancer (OC) patients were obtained at the time of cytoreductive surgery either upfront or after neoadjuvant chemotherapy (interval debulking surgery) at the Northwestern University School of Medicine under an IRB approved protocol (STU00202468). All patients were followed prospectively and received platinum and taxane standard of care chemotherapy. Platinum resistance was defined as disease recurring within 6 months from completing carboplatin-based chemotherapy, as assessed clinically, by CA125 criteria or CT scans. Tumor tissues were enzymatically disassociated into single cell suspensions and cultured as previously described [65, 66]. After centrifugation at 200 g for 5 min, 25,000 ascites derived tumor cells were cultured as monolayers in DMEM medium supplemented with 10% FBS and antibiotics prior to stimulated Raman scattering (SRS) imaging.

In Vivo Experiments

The platinum resistant PDX model was developed as previously described [67]. After passage through a donor animal, fresh tumor (equal size) was implanted subcutaneously (SC) in 20 female 7-8-week-old NSG mice (Jackson Labs, Cat #: JAX:00555). Tumor sizes were measured using calipers twice per week and tumor volumes were calculated according to the formula length×width$^2$/2. When the tumor volume reached 100 mm$^3$, the animals were randomized into four groups: vehicle, carboplatin alone (10 mg/kg weekly intraperitoneal (i.p.) injection), etomoxir alone (40 mg/kg daily i.p. injection), and combination of carboplatin (10 mg/kg weekly i.p. injection) and etomoxir (40 mg/kg daily i.p. injection). Body weights and habitus were monitored twice per week and mice were sacrificed when the largest tumor exceeded 1500 mm$^3$ or if human endpoints were reached earlier.

Xenografts were obtained through intraperitoneally implantation of 2 million OVCAR5 cells in female (6-8 weeks old) athymic nude mice (Foxn1$^{nu}$, Envigo). Two weeks after inoculation, tumor harboring mice were treated with PBS (sensitive group, n=3) or 25 mg/kg carboplatin (resistant group, n=3) via weekly i.p. injection for three cycles. Tumors were collected and weighted one week after the last cycle and frozen. For SRS imaging, tumors were sectioned at 5-10 nm thickness slices by cryostat. To isolate tumor cells from tissue, PBS and carboplatin treated xenografts were mechanically and enzymatically dissociated in Dulbecco's modified Eagle's medium/F12 (Thermo Fisher Scientific) containing collagenase (300 IU/ml, Sigma-Aldrich) and hyaluronidase (300 IU/ml, Sigma-Aldrich) for 2-4 hours at 37° C. Red blood cell lysis used RBC lysis buffer (BioLegend), followed by DNase (Qiagen) treatment and filtering through a 40 μm cell strainer (Fisher Scientific) to yield single cells suspension, which were examined for responsiveness to cisplatin ex vivo.

For all animal experiments, mice were housed at 21° C.-23° C. with a 12/12 dark/light cycle. The humidity of housing environment is 35%. Mice were sacrificed when the largest tumor exceeded 1500 mm$^3$ or if human endpoints were reached earlier. The mouse diet was Cat # is 7912 from Teklad/Envigo.

Large-area Hyperspectral Stimulated Raman Scattering Imaging

Hyperspectral SRS imaging was performed on a lab-built system following previously published method [8]. The laser source was a femtosecond laser (InSight™ DeepSee™, Spectra-Physics™, Santa Clara, CA, USA) operating at 80 MHz with two synchronized output beams, a tunable pump beam ranging from 680 nm to 1300 nm, and a Stokes beam fixed at 1040 nm. For imaging at the C-H vibration region (2800~3050 cm$^{-1}$), pump beam was tuned to 798 nm. The Stokes beam was modulated at 2.3 MHz by an acousto-optic modulator (1205-C, Isomet®). After combination, both beams were chirped by two 12.7 cm long SF57 glass rods and then sent to a laser-scanning microscope. The power of pump and Stokes beam before microscope was controlled to be 20 mW and 200 mW, respectively. A 60× water immersion objective (NA=1.2, UPlanApo/IR™, Olympus) was used to focus the light on the sample, and an oil condenser (NA=1.4, U-AAC, Olympus) was used to collect the signal. For hyperspectral SRS imaging, a 50-image stack was acquired at different pump-Stokes temporal delay, which was controlled by tuning the optical path difference between pump and Stokes beam through a translation delay stage. Raman shift was calibrated using standard samples, including DMSO, oleic acid, and linolenic acid.

To achieve large-area mapping, samples were fixed on a motorized stage (PH117, Prior Scientific). A lab built LabView based program was used to control moving of the stage and stitching of images. The stage moved to adjacent location with partial overlap after a hyperspectral SRS image was acquired at a current location. A montage image composed of 5×5 individual 400×400-pixel images was acquired at each area of interest. The size of the montage image is approximately 500×500 µm. The pixel dwell time was set as 10 µs. For each sample, at least 3 montage images were acquired at different area of interest.

Spectral Phasor and CellProfiler™ Based Single Cell Analysis

The acquired large-area hyperspectral SRS images were segmented through Spectral phasor analysis modified from previously published method [39]. Spectral phasor was installed as a plugin in ImageJ. The images were transformed into a two-dimension phasor plot based on Fourier Transform. Each dot on the phasor plot represents an SRS spectrum at a particular pixel. Pixels with similar spectra or chemical content were clustered on the phasor plot. "Nuclei" and "lipid" images were generated by mapping the corresponding clusters on the phasor plot back to two separate images.

Lipid analysis in single cells were performed through the software CellProfiler™ [68]. The map of nuclei and cell images were input into CellProfiler™ to outline each individual cells. The lipid map was input into CellProfiler™ to pick up the lipid droplet (LD) particles. Then, the lipid map was masked onto the outlined cell map to label the lipids. Morphological information of each cell and lipid analysis, including LD number and intensity in single cells were measured and reported in the output results. The total lipid intensity in each cell was plotted as histogram graphs. For each sample, a few hundreds to a thousand of cells were analyzed.

Isotope Labeling and SRS Imaging

For labeling with glucose-d7, media was replaced with glucose-free DMEM medium (Thermo Fisher Scientific, #11966025)+10% FBS+P/S supplemented with 25 mM glucose-$d_7$ after seeding the cells in 35 mm glass-bottom dishes overnight. For labeling with FA or analogs, including PA-$d_{31}$, OA-$d_{34}$, and ODYA, FA or analogs were added to the culture media at final concentration of 100 µM and cells were treated for 6 h. For quantitative SRS imaging, cells on glass-bottom dishes were fixed with 10% neutral buffered formalin for 30 min and washed with PBS for 3 times. Hyperspectral SRS imaging was performed to the cells at Raman spectral region from 2100 to 2300 $cm^{-1}$.

Reactive Oxidative Species Measurement

Cellular reactive oxidative species (ROS) was measured using a fluorescent probe, 2',7'-Dichlorofluorescin diacetate (DCFDA) (Sigma Aldrich). Cells seeded in glass-bottom dishes were treated with or without 3.3 µM cisplatin for 3 h. DCFDA was added to the medium at final concentration of 10 µM and incubated for 15 min. After washing with PBS for 3 times, cells were immediately imaged under confocal microscope (Zeiss LSM 700 microscope) with 488 nm as the exciting source. Laser power was controlled at low setting to avoid fluorescence extinction. Images at ~10 field of view were acquired for each sample.

Fatty Acid Oxidation Assay

Fatty acid oxidation (FAO) was measured using a commercial kit (Abcam, #ab217602) following the provided protocol. Briefly, cells were seeded in 96-well plate with 150 k cells/well. After incubation overnight, medium was replaced. 10 µL of Extracellular $O_2$ consumption reagent, and 2 drops of high-sensitivity mineral oil (pre-heated at 37° C.) were added to each well. Fluorescence was measured in plate reader at 2 min intervals for 180 min at excitation/emission=380/650 nm. Etomoxir was added at final concentration of 40 µM to block FAO. Oxygen consumption rate (OCR) is presented as ΔFluorescence intensity/Min/cell and FAO rate is calculated as $OCR_{FAO}=OCR_{total}-OCR_{Etomoxir}$. At least three replicates were included for each measurement.

NADPH and ATP Assay

NADP/NADPH and ADP/ATP were measured by using commercial kits (Abcam, #ab65349 and #ab65313). For NADPH measurement, cells (~1×10$^6$ cells) were pelleted and extracted using NADPH/NADP extraction buffer. Total NADP/NADPH was directly measured using the assay kit and NADPH alone was measured after decomposing NADP by heating at 60° C. for 30 min. Absorption at 450 nm was measured by plate reader (Molecular Devices, SpectraMax i3x). For ATP measurement, cells were seeded in 96-well plates. ATP was measured directly and total ATP+ADP was measured by converting ADP to ATP. The luminescent signal was measured by plate reader. At least three replicates were included for each measurement.

Cell Viability Assay

Cell viability was measured by MTS assay (Abcam, #ab197010) or by CellTiter-Glo™ assay (Promega, #G7570). Cells were seeded at 96-well plates at densities of 2000~5000 cells per well overnight. Treatment was added to the cells at indicated concentrations for 72 h. Cell viability was measured by incubating with MTS reagent for 4 h and reading absorbance at 490 nm or incubating with CellTier-Glo™ reagent for 10 min and reading luminescence by a plate reader. Six replicates were used for each group.

Glucose Uptake Assay

Glucose uptake was measured using a fluorescent glucose analog 2-deoxy-2-[(7-nitro-2,1,3-benzoxadiazol-4-yl)amino]-D-glucose (2-NBDG) (Cayman Chemicals). Cells seeded in glass-bottom dishes were incubated with 100 µM 2-NBDG for 2 h. Fluorescent images were taken by confocal microscope (Zeiss® LSM 700 microscope) with 488 nm laser as excitation source. Images at ~10 field of view were acquired for each sample.

Measurement of OCR and ECAR by Seahorse® Analysis

Cell lines were seeded in a Seahorse® XF96 Cell Culture Microplate (Agilent) at density of 6×10$^4$ (OVCAR5 pair) or 4×10$^4$ (PEO pair) per well. After incubation at 37° C. overnight for cell attachment, OCR, and extracellular acidification rate (ECAR) were measured through Seahorse® XFe96 Analyzer (Agilent). Measurement time was 30 seconds following 3 minutes mixture and 30 seconds waiting time. First three cycles were used for basal respiration measurement. Effects of mitochondrial respiration inhibitors 4 µM oligomycin, 4 µM FCCP, 25 µM rotenone, 50 µM antimycin A, 26.4 µM cisplatin, or 40 µM etomoxir on OC cells OCR and ECAR were measured. Basal respiration, ATP production and maximal respiration reduction were calculated following the manufacturer's instructions.

Reverse Transcription-PCR (RT-PCR)

Total RNA from ovarian cell lines were extracted via RNeasy® Mini Kit (Qiagen Inc.) and reverse transcribed by iScript® cDNA Synthesis Kit (Bio-Rad). RT-PCR was performed through StepOne Plus RT-PCR (Applied Biosystems) using Power SYBR Green Master Mix (Thermo Fisher Scientific). Primer sequences, SEQ ID NOs: 1-24, are listed in Table 1. All procedures were following manufactures' instructions.

TABLE 1

Primer sequences used for RT-PCR measurement.

| Gene name | Forward sequence | Backward sequence |
|---|---|---|
| CPT1a | TCCAGTTGGCTTA TCGTGGTG SEQ ID NO: 1 | TCCAGAGTCCGAT TGATTTTTGC SEQ ID NO: 2 |
| FABP5 | TGAAGGAGCTAGG AGTGGGAA SEQ ID NO: 3 | TGCACCATCTGTA AAGTTGCAG SEQ ID NO: 4 |
| FABP (PM) | GGAAGGAAATAGC AACAGTGG SEQ ID NO: 5 | TCCTACACGCTCA CCATATAAGC SEQ ID NO: 6 |
| FATP1 | CTTCGATGGCTAT GTCAGCGA SEQ ID NO: 7 | AGCACGTCACCTG AGAGGTAG SEQ ID NO: 8 |
| FATP2 | ATGCGAGAAAGT TGGTGCT SEQ ID NO: 9 | TTTCATCACGGAC AGGTTCA SEQ ID NO: 10 |
| FATP3 | ATACCTGGGAGCG TTTTGTG SEQ ID NO: 11 | CCGCTGTCCTGTG TAGTTGA SEQ ID NO: 12 |
| FATP4 | CTTTTCCAGCCGC TTCCACA SEQ ID NO: 13 | TGGCTGGCAGGGA ATGCA SEQ ID NO: 14 |
| FATP5 | AGCTCCTGCGGTA CTTGTGT SEQ ID NO: 15 | AAGGTCTCCCACA CATCAGC SEQ ID NO: 16 |
| FATP6 | GCTGGGCCTTATA AGCACACA SEQ ID NO: 17 | CAACCTCAGTGGT TGCGACA SEQ ID NO: 18 |
| CD36 | GGCTGTGACCGGA ACTGTG SEQ ID NO: 19 | AGGTCTCCAACTG GCATTAGAA SEQ ID NO: 20 |
| FABP4 | ACTGGGCCAGGAA TTTGACG SEQ ID NO: 21 | CTCGTGGAAGTGA CGCCTT SEQ ID NO: 22 |
| PPIA | CCCACCGTGTTCT TCGACATT SEQ ID NO: 23 | GGACCCGTATGCT TTAGGATGA SEQ ID NO: 24 |

RT-PCR reaction generated a melting curve, and cycle threshold (Ct) was recorded for the gene of interest and house-keeping control gene (PPIA). The relative RNA expression level was calculated as ΔCt and normalized by subtracting the Ct value of target gene from that of control gene. Results are presented as means+SD. Measurements were performed in biological triplicate and each biological replicate includes three technical replicates.

Western Blot

Proteins were extracted from cell culture by RIPA lysis buffer (Sigma Aldrich) with protease and phosphatase inhibitor cocktail and sample reducing agent (Thermo Fisher Scientific). Proteins were separated in Bolt™ Bis-Tris Plus gels (Thermo Fisher Scientific) through gel electrophoresis and transferred to PVDF membrane (Bio-Rad). After blocking in 5% non-fat milk (Bio-Rad) for 1 hour at room temperature, membranes were incubated with primary antibodies (CPT1a (1:1000) (Proteintech Cat #: 15184-1-AP; RRID: AB_2084676) and GapDH (1:2000) (Proteintech; Cat #: 60004-1-Ig; RRID: AB_2107436; Clone #: 1E6D9) overnight at 4° C. followed by secondary anti-mouse antibodies (1:10000) (Proteintech; Cat #: SA00001-1; RRID: AB_2722565) for 1 hour at room temperature. Protein bands were developed by ECL reagent (Thermo Fisher Scientific) and detected through ChemiDoc MP imaging system (Bio-Rad). The band intensity was determined using ImageJ. Full scan blots are in the Source Data file (not shown).

RNA Sequencing Analysis

RNA-seq data from OVCAR-5 and SKOV-3 cisplatin-resistant versus parental cells were downloaded from the Gene Expression Omnibus with accession ID: GSE148003 [40]. Raw data were normalized with the R package edgeR [69]. Overlapping genes in the Hallmark Fatty Acid Metabolism gene set between OVCAR5-cisR versus parental cells and SKOV3-cisR versus parental cells were used for generating heatmaps using the R package heatmap. Specifically, the heatmap of hierarchical clustering was generated for OVCAR5-cisR versus parental cells by using normalized counts. The same gene order after hierarchical clustering was applied to produce a heatmap for SKOV3-cisR versus parental cells.

Quantification and Statistical Analysis

All the data are presented as means±SD unless otherwise specified. The statistical significance was analyzed using two-tailed Student's t test. All experiments were repeated at least 3 times. N is indicated sample size for each experiment. $P<0.05$ was considered statistically different. Statistical parameters can be found in figure legends. Data was analyzed and qualified by ImageJ, MATLAB, and Microsoft Excel. Origin was used for figure generation.

Data Availability

The RNA-seq data used in this paper are available in the Gene Expression Omnibus with accession ID: GSE148003 [https://www.ncbi.nlm.nih.govigeo/query/acc.cgi?acc=GSE148003].

Example 1

Figure 1A:
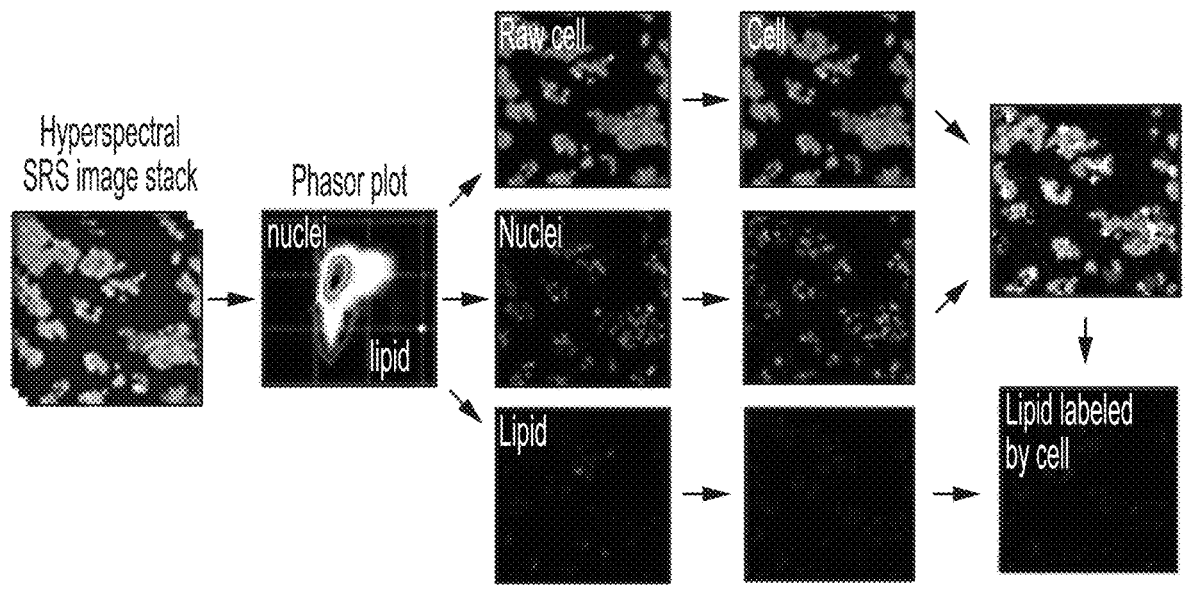
FIGS. 1A-1Q illustrate high-throughput profiling of lipid metabolism in ovarian cancer cell lines.
Figure 1B:
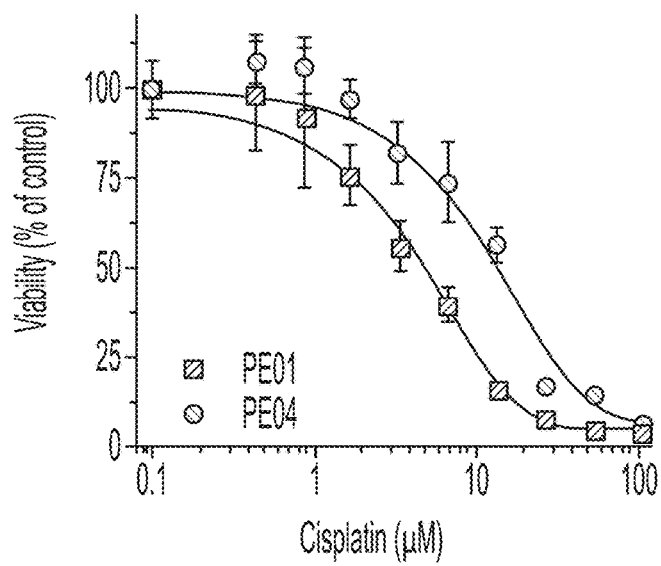
FIGS. 1B-1E show dose-response to cisplatin in PEO1 and PEO4 (FIG. 1B), SKOV3 and SKOV3-cisR (FIG. 1C), OVCAR5 and OVCAR5-cisR (FIG. 1D), COV362 and COV362-cisR cells (FIG. 1E); n=6 biological replicates.
Figure 1C:
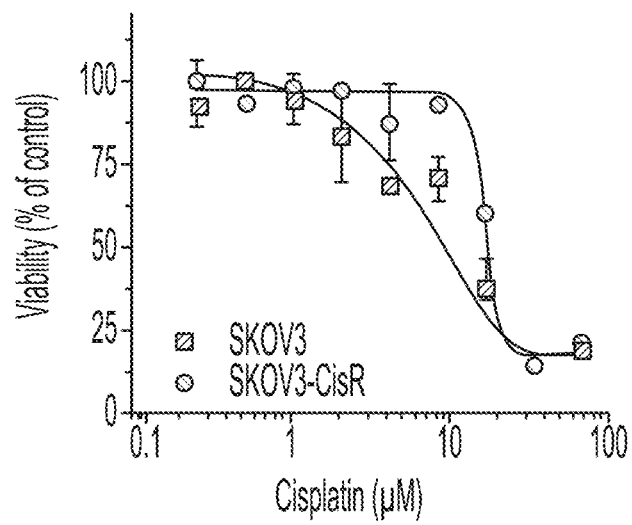
Figure 1D:
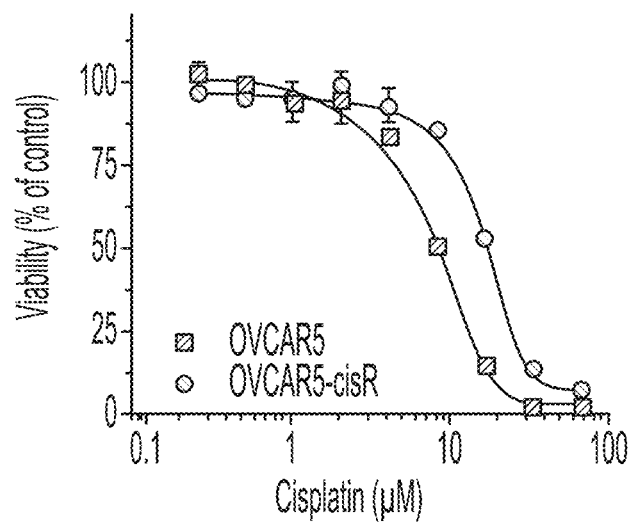
Figure 1E:
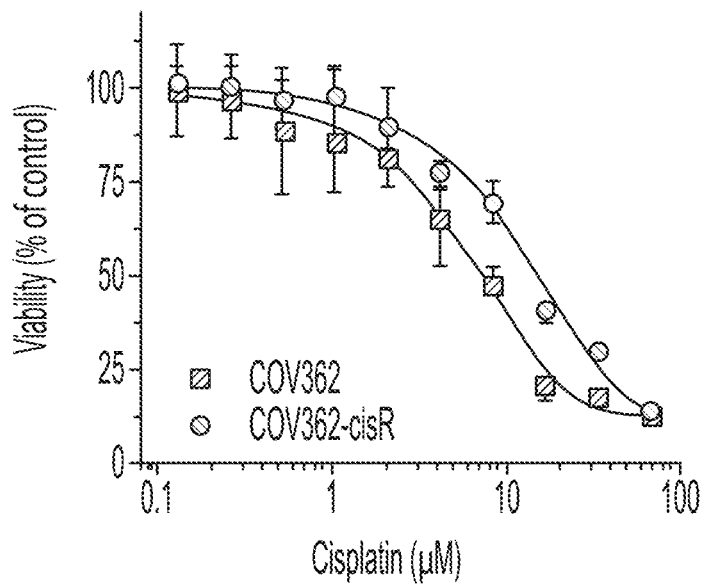

High-throughput SRS Imaging Unveils Lipid Accumulation in Ovarian Cancer Cells with Platinum Resistance To identify the altered lipid metabolism in cisplatin-resistant cells, a high-throughput single-cell analysis approach was established that couples large-area hyperspectral SRS scanning of 200-500 cells per group with spectral phasor segmentation and CellProfiler™ analysis. As shown in FIG. 1A, a stack of large-area hyperspectral SRS images were acquired containing hundreds of individual cells in each field-of-view. An SRS spectrum was extracted at each pixel from the image stack. Then, the hyperspectral SRS images were segmented through a spectral phasor algorithm to generate maps of intracellular compartments corresponding to nuclei and lipids (mostly in lipid droplets) based on the spectrum similarity [39]. Next, the nuclei map was inputted into CellProfiler™ to guide the identification of the edges of each individual cell from the raw whole cell image. After individual cells were outlined, the lipid map was mapped back to the corresponding cells. Lipids were color-coded based on the colors of their parental cells. Finally, quantitative characterization of lipids in terms of integrated intensity, mean intensity, area, and lipid droplet size in each individual cell was performed. The image area is 500 μm by 500 μm.

To explore the lipid metabolic signature of cisplatin-resistant OC cells, isogenic pairs of cisplatin-resistant cells from three OC cell lines were generated, including SKOV3, OVCAR5, and COV362, through repeated long-time exposures and recoveries after cisplatin treatment at $IC_{50}$ concentration [40]. Resistance to cisplatin in these cell lines was validated by repeat assays measuring cisplatin dose response. All the resistant cell lines exhibited 2-3-fold increase of $IC_{50}$ when compared to their parental counterpart cell lines (FIGS. 1B-1E). In addition, isogenic PEO1/PEO4 cell lines derived from the same patient were studied, at the time of a platinum sensitive (PEO1) and platinum resistant-recurrence (PEO4) [41].

Figure 1F:
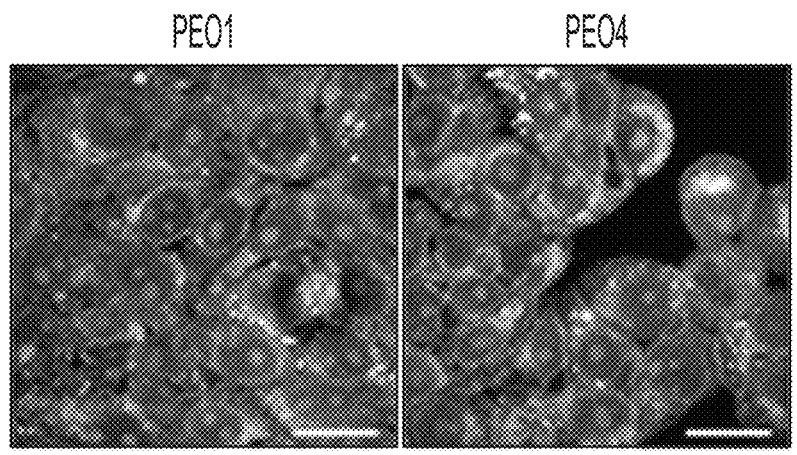
FIG. 1F shows representative large-area SRS images of parental PEO1 and cisplatin-resistant PEO4 cells (isogenic pairs of cisplatin-sensitive and cisplatin-resistant ovarian cancer (OC) cells).
Figure 1G:
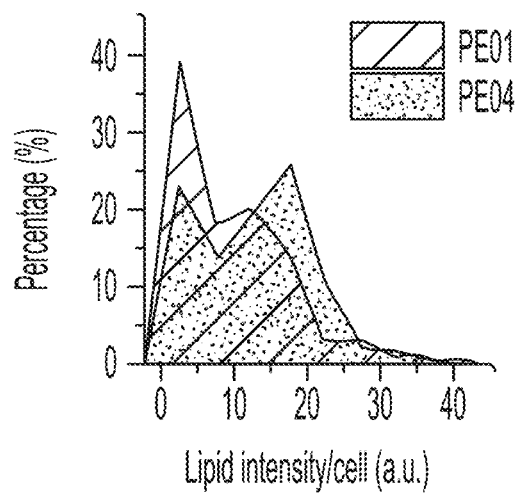
FIG. 1G shows histograms of integrated cellular lipid intensity in PEO1 and PEO4 cells generated through high-throughput single-cell analysis.
Figure 1H:
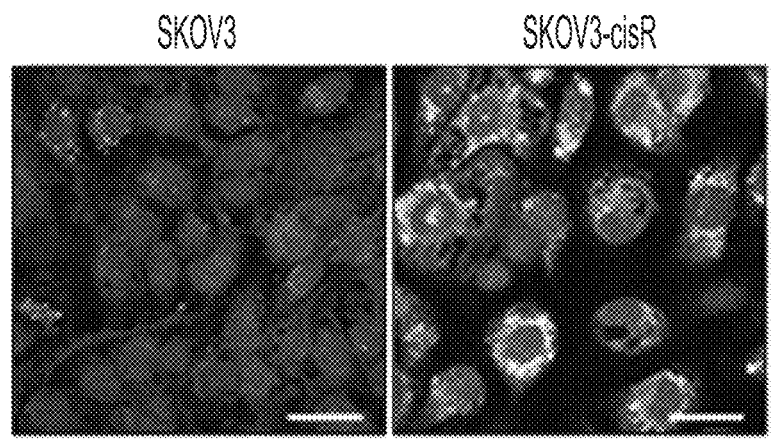
FIG. 1H shows representative large-area SRS images of parental SKOV3 and cisplatin-resistant SKOV3-cisR cells.
Figure 1I:
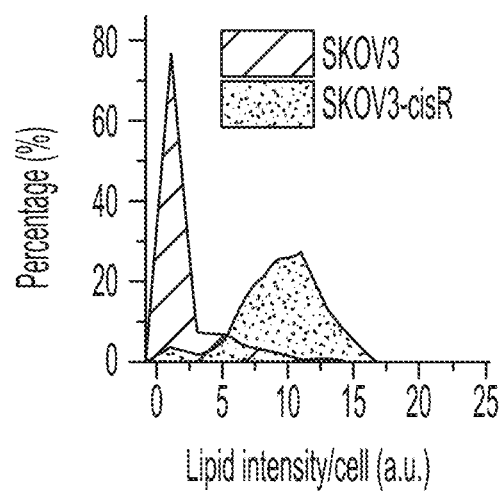
FIG. 1I shows a histogram of integrated cellular lipid intensity in SKOV3 and SKOV3-cisR cells. Data for FIGS. 1F-1I are presented as mean+SD; n=3 animals; two-sided Student's t test; P=0.043; * P<0.05. All scale bar: 20 µm.
Figure 1J:
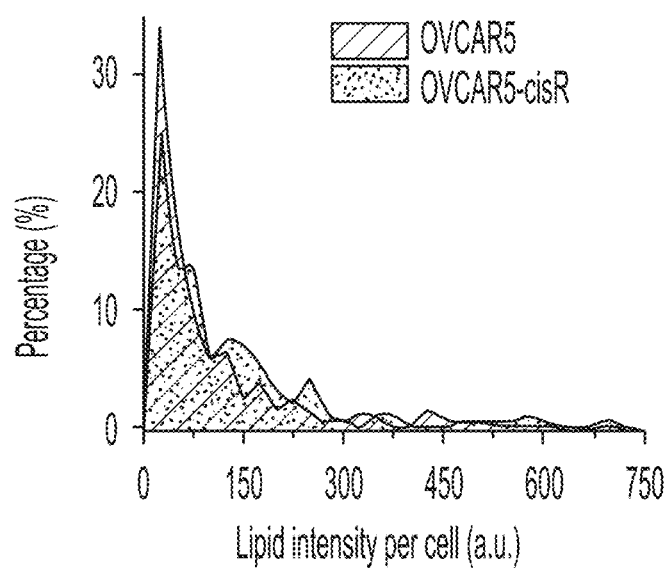
FIGS. 1J-1K show histograms of integrated cellular lipid intensity in OVCAR5 and OVCAR5-cisR (FIG. 1J), and in COV362 and COV362-cisR cells (FIG. 1K).
Figure 1K:
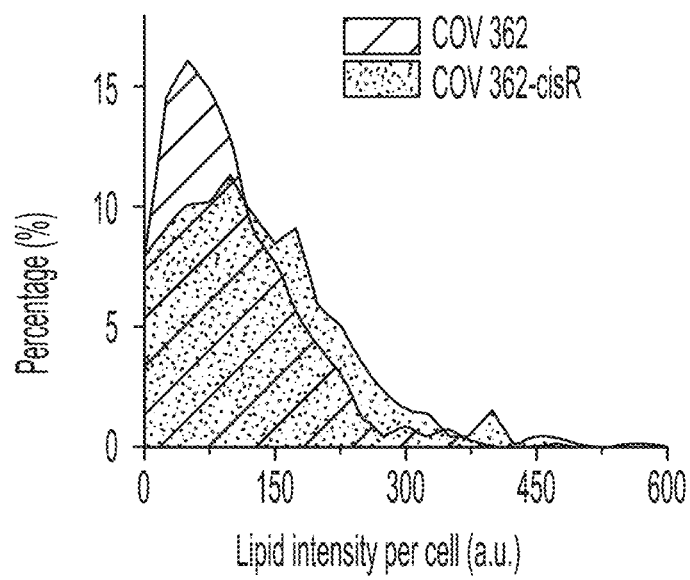
Figure 1L:
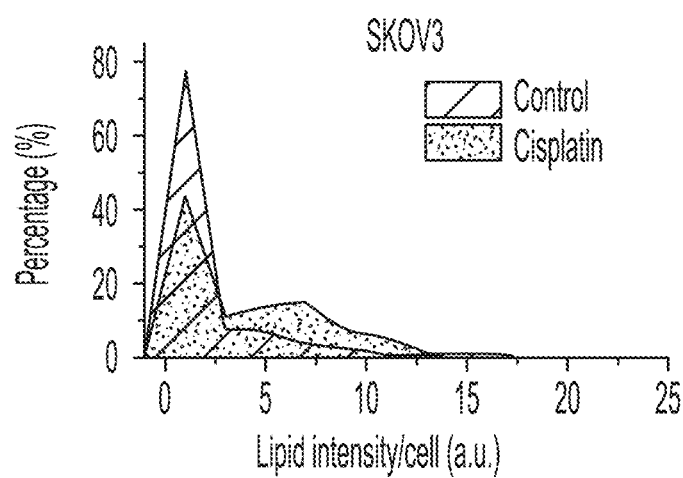
FIGS. 1L-1M show histograms of integrated cellular lipid intensity in SKOV3 cells (FIG. 1L) and in SKOV3-cisR cells (FIG. 1M) treated with or without cisplatin. Data are presented as mean+SD; n=3 animals; two-sided Student's t test; P=0.043; * P<0.05. All scale bar: 20 µm.
Figure 1M:
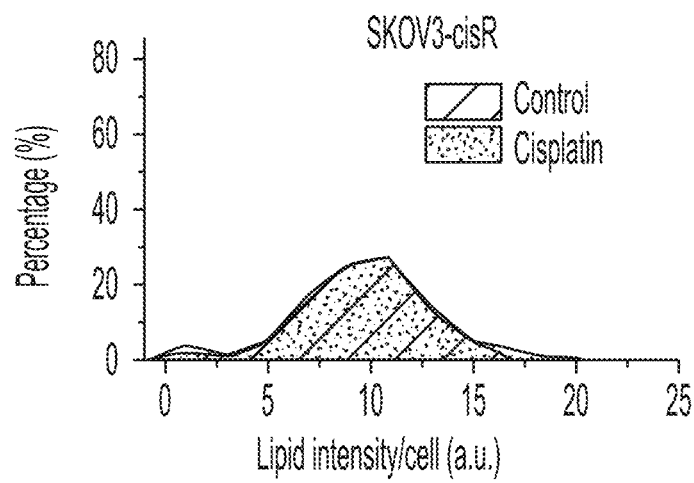

Using the high-throughput imaging analysis platform, the lipid metabolism in these four pairs of cisplatin-resistant and parental ovarian cancer cell lines were analyzed. Comparison of SRS images of sensitive PEO1 and cisplatin-resistant PEO4 cells showed an increase of lipid intensity in PEO4 cells, but with large cell-to-cell variations (FIG. 1F). The integrated lipid intensity in individual cells was quantitatively analyzed and plotted in histograms. The histograms displayed two distinct subpopulations, lipid-poor and lipid-rich, in each cell line, indicating metabolic heterogeneity within the same group. While lipid-poor cells dominated in PEO1 cell line, PEO4 cells showed a dramatic increase in lipid-rich subpopulation and a decrease in lipid-poor subpopulation (FIG. 1G). Single-cell analysis revealed an even more obvious increase in lipid-rich subpopulation and decrease in lipid-poor subpopulations in SKOV3-cisR cells, compared to SKOV3 (FIGS. 1H and 1I). Additionally, similar lipid content changes were observed in the other two pairs of cell lines, OVCAR5 versus OVCAR5-cisR (FIG. 1J), and COV362 versus COV362-cisR (FIG. 1K), supporting that cisplatin-resistant cells harbor higher levels of lipid accumulation. Furthermore, after acute treatment with cisplatin, a significant increase in lipid-rich subpopulation, and decrease of lipid-poor subpopulation was found in SKOV3 cells (FIG. 1L), but no obvious change of lipid distribution pattern in SKOV3-cisR cells were detected (FIG. 1M), supporting that lipid-rich cells are more resistant to cisplatin treatment.

Figure 1N:
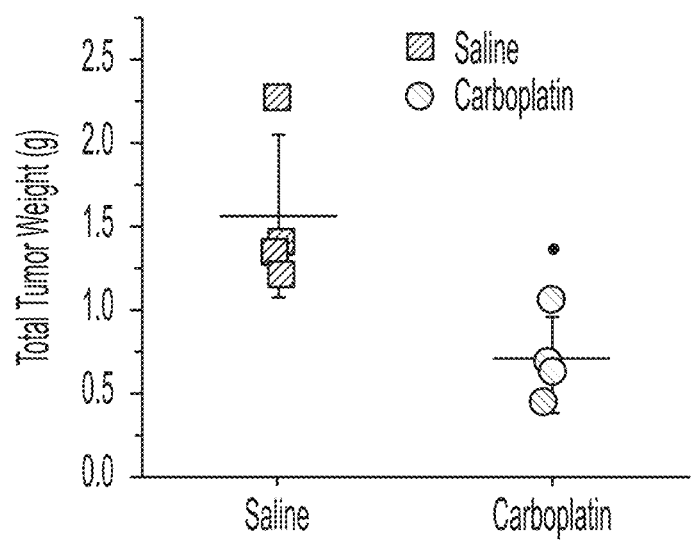
FIG. 1N illustrate weights of xenografts from mice treated with saline or carboplatin for 3 weeks; (n=4, two-sided Student's t test; P=0.030; * P<0.05).
Figure 1O:
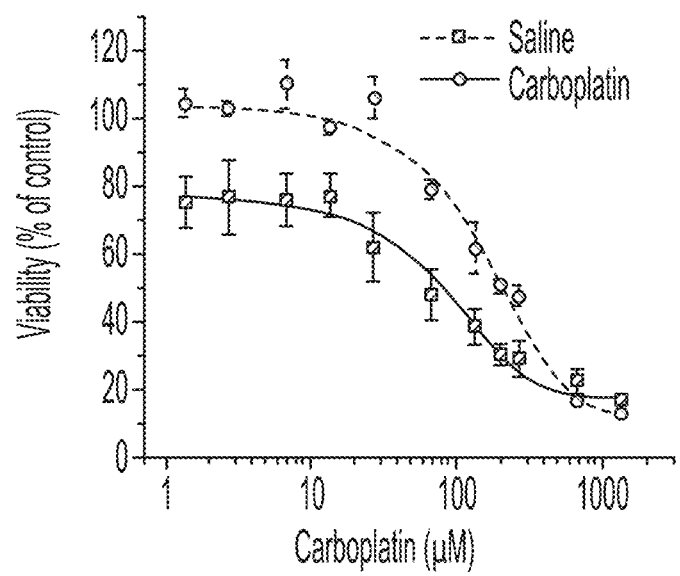
FIG. 1O shows a dose-response to carboplatin in OC cells derived from xenografts developed in mice treated with carboplatin or saline; the dose-response curves and scatter plot are shown as means±SD, n=4 technical replicates.
Figure 1P:
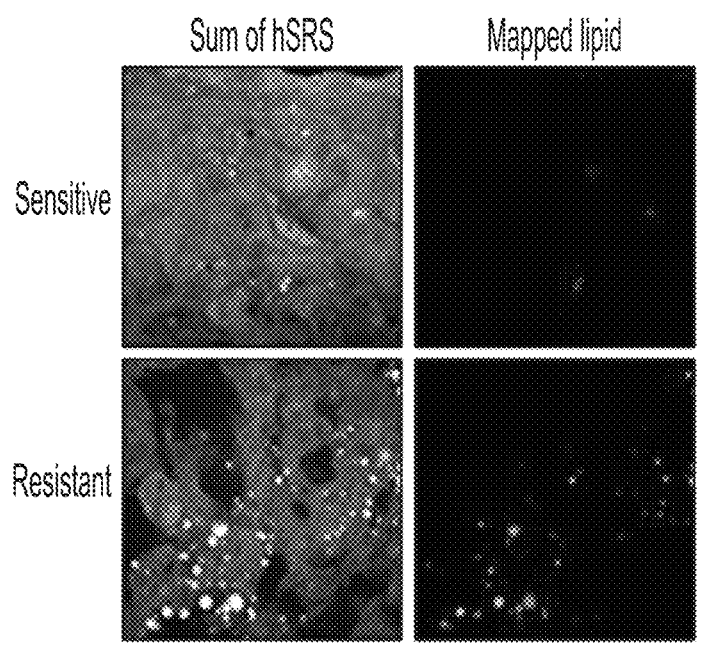
FIG. 1P presents a representative hyperspectral SRS image (sum of all channels) and Phasor mapped lipid image of sliced OVCAR5 xenograft tumor tissue from mouse treated with vehicle (sensitive) or carboplatin (resistant).
Figure 1Q:
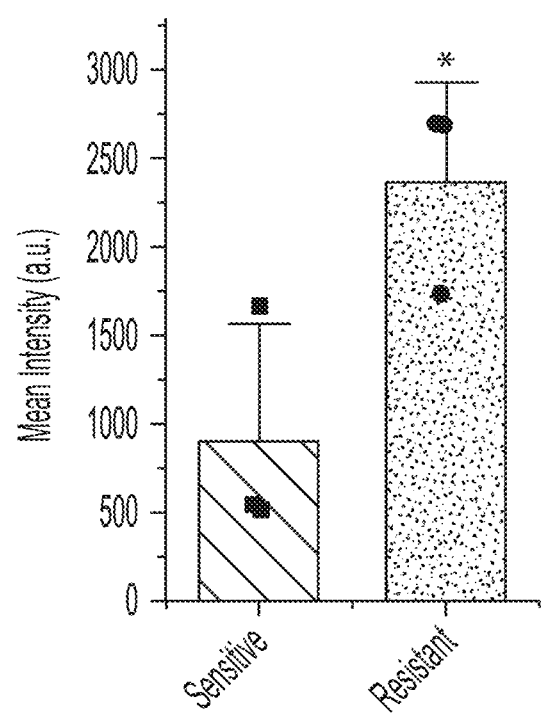

To determine whether lipid accumulation also occurs in vivo in platinum-treated tumors, SRS imaging of lipids was performed in OVCAR5 xenografts collected from mice treated weekly with saline or carboplatin for three weeks. Tumor growth was suppressed by carboplatin treatment (FIG. 1N). However, cells isolated from xenografts residual after carboplatin treatment showed increased resistance to carboplatin in in vitro treatment, compared to cells isolated from the saline treated tumors. (FIG. 1O). The results shown in FIGS. 1P-1Q indicate heterogeneous lipid accumulation and higher lipid amount in the carboplatin-treated tumors compared with the platinum-sensitive tumors. Collectively, higher level of lipid content was a metabolic feature of cisplatin-resistant ovarian cancer cells.

Example 2

Figure 2A:
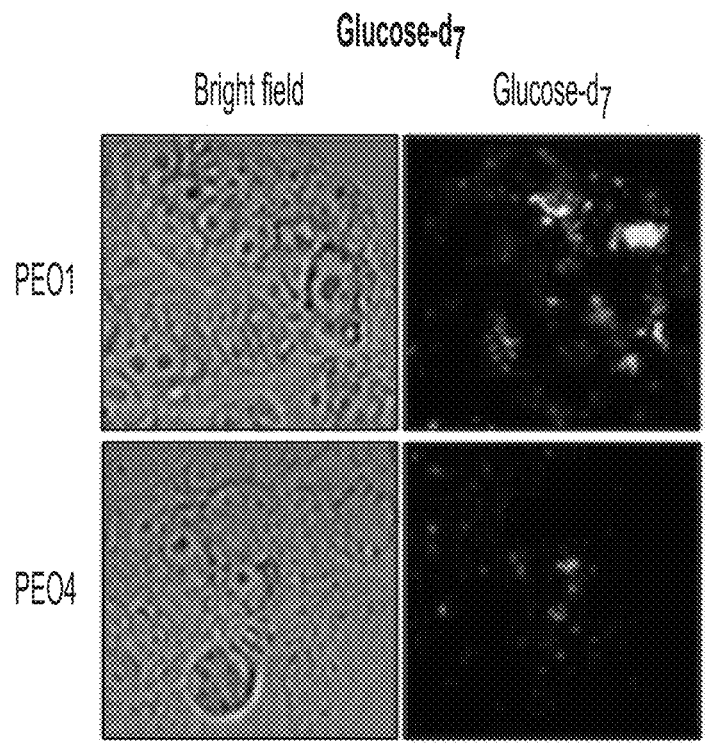
FIGS. 2A-2M illustrate increased fatty acid uptake, not de novo lipogenesis, is the major contributor to lipid accumulation in cisplatin-resistant OC cells.
Figure 2B:
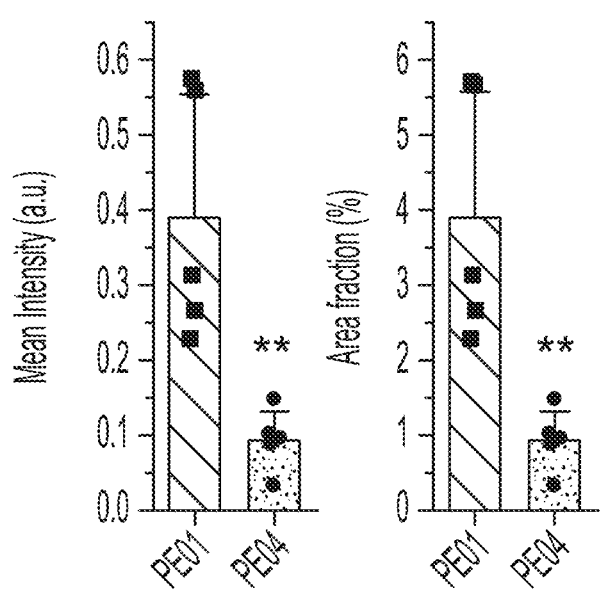
Figure 2C:
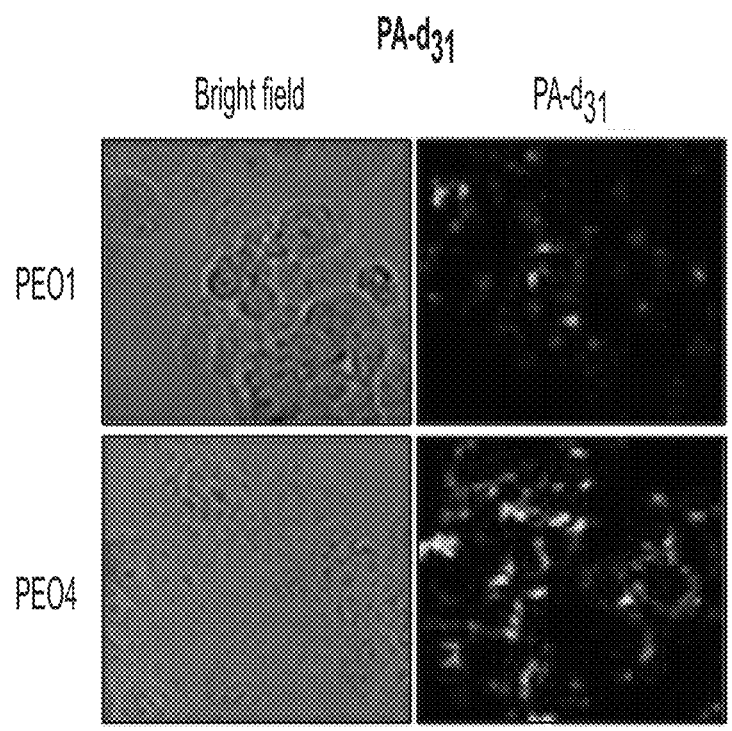
Figure 2D:
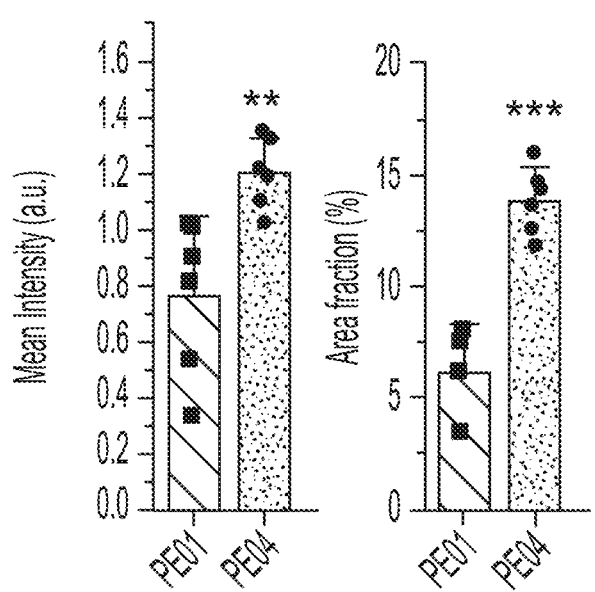
Figure 2E:
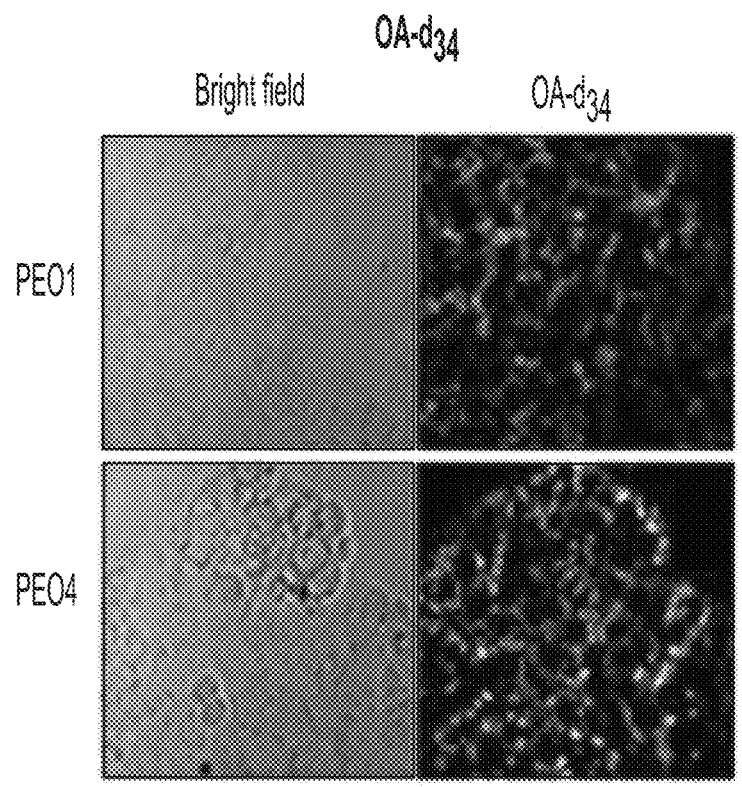
Figure 2F:
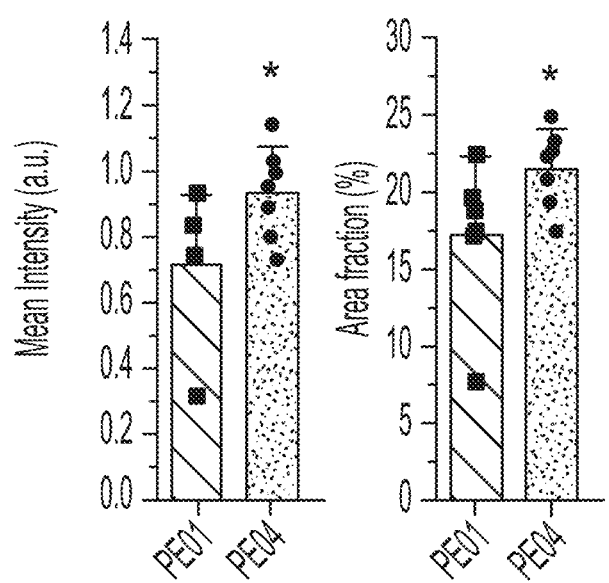

Increased Fatty Acid Uptake but not De Novo Lipogenesis Contributes to High-Level Lipid Content in Cisplatin-Resistant Ovarian Cancer Cells To identify the source of increased lipid content in cisplatin-resistant ovarian cancer cells, the contribution of de novo lipogenesis and of fatty acid uptake were examined, respectively. Using a stable isotope probing method [35], the level of lipogenesis was examined by feeding the cells with deuterium labeled glucose-$d_7$. Newly synthesized macromolecules (mostly lipids) were imaged by hyperspectral SRS microscopy at Raman shift from 2050 $cm^{-1}$ to 2350 $cm^{-1}$, covering the vibrational frequencies of C-D bonds. SRS images showed weaker C-D signal in cisplatin-resistant PEO4 cells than the signal in parental PEO1 cells (FIG. 2A). Quantitative analysis confirmed significant reduction of both signal intensity and relative area fraction in PEO4 cells when compared to PEO1 cells (FIG. 2B), indicating a decrease in glucose derived anabolism and de novo lipogenesis in cisplatin-resistant cells. Using a similar approach, the fatty acid uptake was examined by hyperspectral SRS imaging at C-D vibrational frequencies in cells fed with deuterium labeled palmitic acid-$d_{31}$ (PA-$d_{31}$). In contrast to glucose-$d_7$ fed cells, C-D signal in PA-$d_{31}$ fed PEO4 cells was stronger than PEO1 cells (FIG. 2C). Quantitative analysis revealed significant increase of both signal intensity and relative area fraction (FIG. 2D). In addition to saturated FA (PA-$d_{31}$), the uptake of an unsaturated fatty acid, oleic acid-d34 (OA-$d_{34}$) was tested. OA-$d_{34}$ uptake was significantly increased in PEO4 cells compared to PEO1 cells (FIGS. 2E and 2F). These results indicate that the increased uptake of fatty acid was not specific to a certain type of fatty acid, but rather reflects a general upregulation of fatty acid uptake pathway.

Figure 2G:
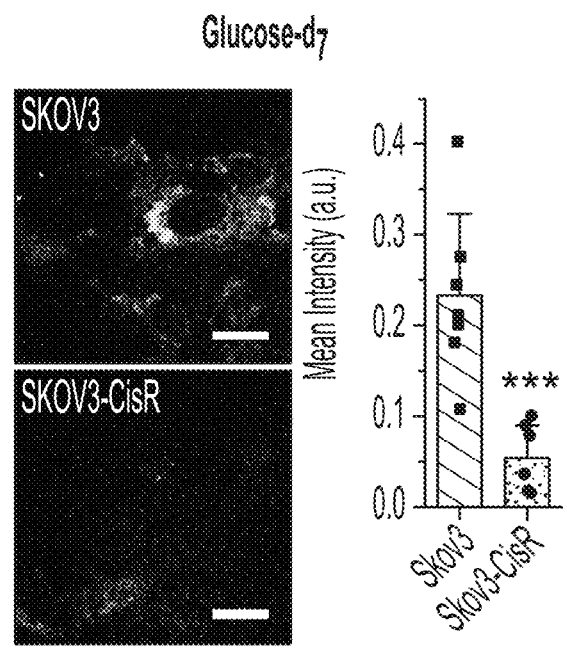
Figure 2H:
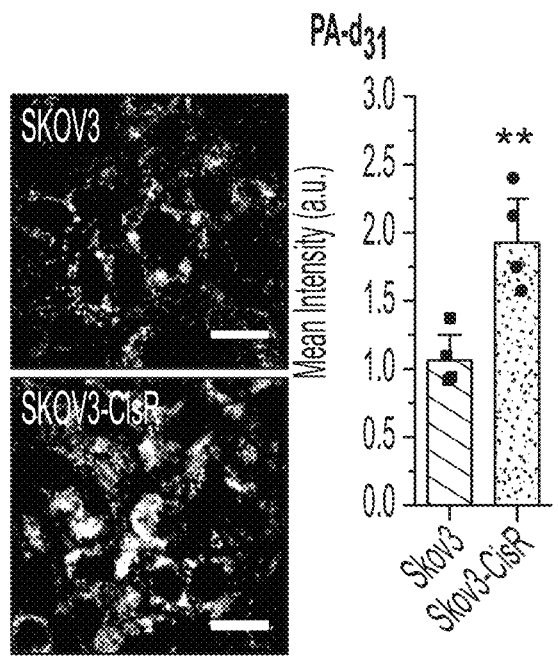
Figure 2I:
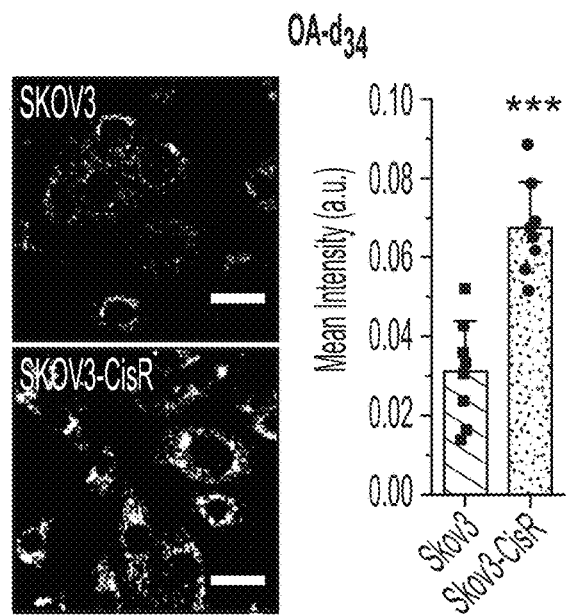
Figure 2J:
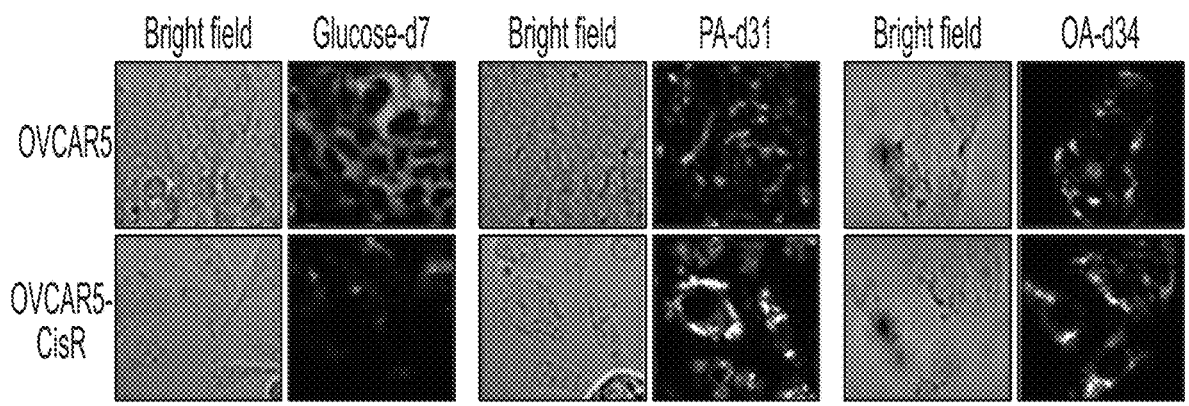
Figure 2K:
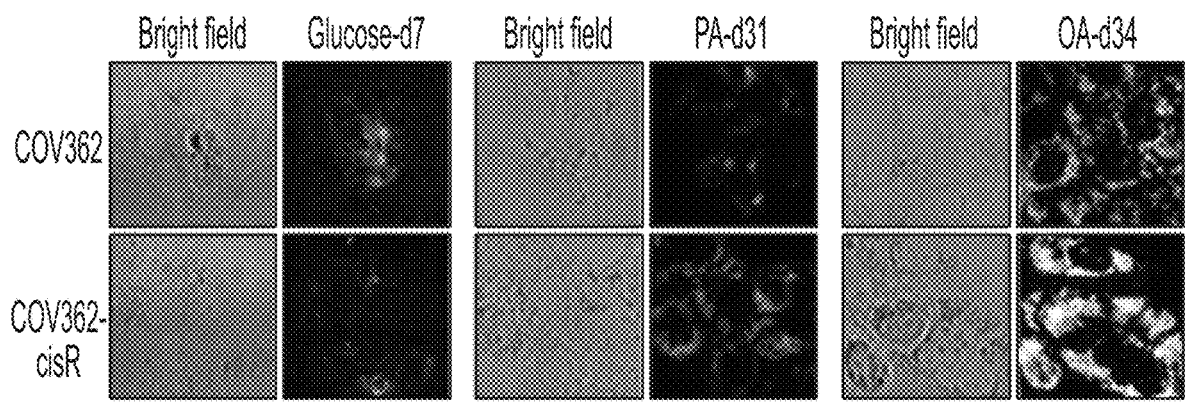
Figure 2L:
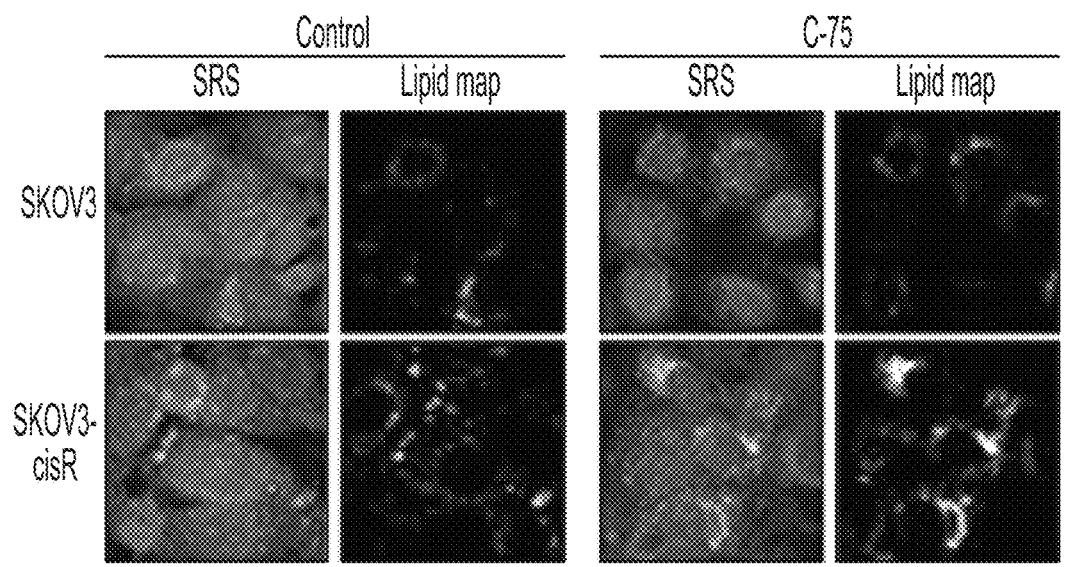
Figure 2M:
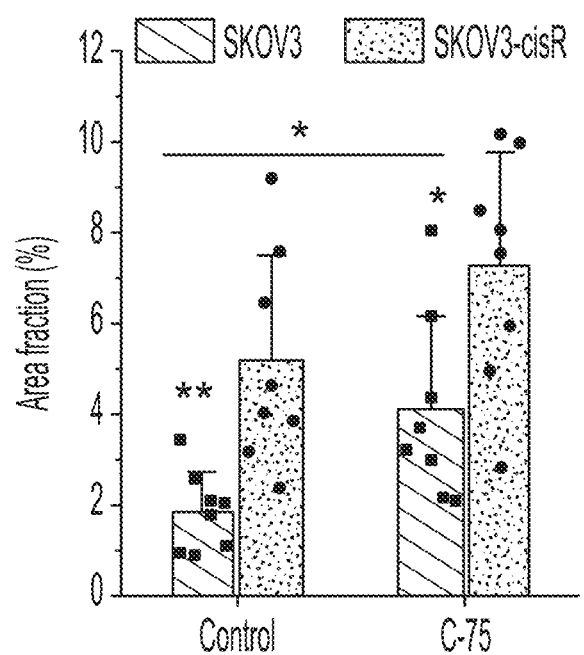

To verify if the observed phenomenon was cell type specific, the measurements were repeated in SKOV3 and SKOV3-cisR cells. Consistently, SRS images and quantitative analysis showed a significant decrease in glucose-$d_7$ derived C-D signal in SKOV3-cisR cells (FIG. 2G) and increase in PA-d31 signal (FIG. 2H) and OA-d34 signal in SKOV3-cisR cells (FIG. 2I), when compared to parental SKOV3 cells. Additionally, the same trend was observed in the other two pairs of cell lines, OVCAR5 versus OVCAR5-cisR (FIG. 2J) and COV362 versus COV362-cisR (FIG. 2K). In addition, inhibition of de novo lipogenesis by the FASN inhibitor C-75 did not affect the increased lipid content in SKOV3-cisR compared with SKOV3, indicating that the enhanced lipid amount in cisplatin resistant cells is independent of de novo lipogenesis (FIGS. 2L and 2M). These data collectively suggest a metabolic change from glucose derived anabolism to fatty acid uptake in cisplatin-resistant ovarian cancer cells.

Example 3

Metabolic Index as a Predictor of Cisplatin Resistance

Having shown decreased glucose-derived anabolism and increased fatty acid uptake in cisplatin-resistant ovarian cancer cells, whether this metabolic feature can be used for differentiation of cisplatin-resistant from cisplatin-sensitive cancer cells was explored. To quantitatively characterize resistance to cisplatin, $IC_{50}$ dose of cisplatin in various cell lines and their C-D intensities (presented as area fraction) from glucose-$d_7$, PA-$d_{31}$, or OA-$d_{34}$ were calculated (Table 2). In Table 2 below, quantitation of glucose-d7 (G-d7), PA-$d_{31}$, and OA-$d_{34}$ are shown as area fraction of C-D signal out of total cellular area, in mean values.

TABLE 2

Summary of quantitation results of glucose-$d_7$, PA-$d_{31}$, and OA-$d_{34}$ and $IC_{50}$s for cisplatin in 4 pairs of parental and cisplatin-resistant ovarian cancer cells.

| Cell lines | $IC_{50}$ for cisplatin (μM) | Intensity (area fraction (%)) | | |
|---|---|---|---|---|
| | | G-$d_7$ | PA-$d_{31}$ | OA-$d_{34}$ |
| PEO1 | 4.72 | 3.88 | 6.11 | 17.25 |
| PEO4 | 13.57 | 0.93 | 13.69 | 21.61 |

TABLE 2-continued

Summary of quantitation results of glucose-$d_7$, PA-$d_{31}$, and OA-$d_{34}$ and IC$_{50}$s for cisplatin in 4 pairs of parental and cisplatin-resistant ovarian cancer cells.

| Cell lines | IC$_{50}$ for cisplatin (μM) | Intensity (area fraction (%)) | | |
|---|---|---|---|---|
| | | G-$d_7$ | PA-$d_{31}$ | OA-$d_{34}$ |
| SKOV3 | 10.07 | 3.39 | 9.88 | 6.24 |
| SKOV3-CisR | 17.29 | 0.84 | 15.79 | 10.97 |
| OVCAR5 | 8.26 | 3.64 | 10.37 | 18.35 |
| OVCAR5-CisR | 17.43 | 2.51 | 15.91 | 23.28 |
| COV362 | 7.19 | 3.14 | 4.44 | 31.00 |
| COV362-cisR | 15.17 | 2.03 | 14.88 | 41.43 |

Interestingly, glucose-d7 derived C-D intensity was found negatively correlated to IC$_{50}$ to cisplatin (FIG. 3A), while PA-$d_{31}$ intensity was positively correlated to IC$_{50}$ to cisplatin (FIG. 3B). To integrate two measurements into one, the ratio of PA-$d_{31}$/(PA-$d_{31}$+Glucose-$d_7$) was used to give a dimensionless number ranging from 0 to 1. This ratio was defined as the "metabolic index". The index linearly correlated to the IC$_{50}$ to cisplatin (FIG. 3C), providing the ability to detect and quantitatively determine resistance to cisplatin in cancer cells.

Understanding the value of this metabolic imaging method for detecting cisplatin resistance at the single cell level, hyperspectral SRS imaging was applied to measure glucose derived anabolism and fatty acid uptake simultaneously in the same cells cultured with Raman probes of fatty acid and glucose. Specifically, glucose-$d_7$ was used to follow glucose anabolism [35, 36]. Instead of using deuterium labeled fatty acid to trace fatty acid uptake, a fatty acid analog was used, 17-octadecynoic acid (ODYA). ODYA has an endogenous CC at one end of the FA chain, which produces a strong Raman peak around 2100 cm$^{-1}$ (FIG. 3D). The distinctive Raman spectrum of ODYA enables spectral separation of C≡C labeled fatty acid (from fatty acid uptake) from C-D labeled macromolecules derived from glucose-$d_7$ (FIG. 3D). To test this in a biological environment, hyperspectral SRS imaging was performed in cells fed with both ODYA and glucose-$d_7$. Two signals were observed with distinctive spectra, from CC labeled fatty acid and C-D derived from glucose-$d_7$, respectively (FIG. 3E).

Next, this approach was applied to image OVCAR5 and OVCAR5-cisR cells. Two components, C≡C and C-D, were segmented from the raw SRS images based on the spectral phasor algorithm[39]. Consistently, stronger C≡C signal and weaker C-D signal were observed in OVCAR5-cisR cells, when compared to OVCAR5 cells (FIG. 3F). Quantitative analysis confirmed a significant increase of CC and decrease of C-D signal. The metabolic index, ratio of C≡C/(C≡C+C-D), was more significantly increased in OVCAR5-cisR cells (FIG. 3G). Following this validated protocol, metabolic indices were analyzed in the other three pairs of cell lines, including PEO1 and PEO4 (FIGS. 3H and 3I), SKOV3 and SKOV3-cisR (images not shown), and COV362 and COV362-cisR cells (images not shown). Consistently, a linear correlation was established between metabolic index and IC$_{50}$ of cisplatin in these cell lines (FIG. 3J).

To further validate the metabolic index as a predictor of platinum resistance in clinically relevant samples, this method was applied to primary ovarian cancer cells obtained from de-identified consenting patients for whom data on resistance/response to platinum was available. Patients' characteristics are included in Table 3 below. Tumor specimens were obtained at the time of cytoreductive surgery either upfront (n=4) or after neoadjuvant chemotherapy (n=7). Platinum resistance was defined as disease recurring within six months from completing carboplatin based chemotherapy, as assessed clinically, by CA125 criteria or CT scans. (n=11 patients).

TABLE 3

Patient characteristics for primary cells used for metabolic index calculation.

| Carboplatin Sensitive | | Carboplatin Resistant | |
|---|---|---|---|
| Patient ID | Chemotherapy before surgery | Patient ID | Chemotherapy before surgery |
| 1 | Yes | 8 | Yes |
| 2 | Yes | 9 | Yes |
| 3 | No | 10 | Yes |
| 4 | No | 11 | Yes |
| 5 | Yes | | |
| 6 | No | | |
| 7 | Yes | | |

As shown in FIG. 3K, in ovarian cancer cells isolated from a patient with platinum-sensitive disease, signal from ODYA was observed only in some of the cells, but the signal from glucose-$d_7$ was relatively strong. In ovarian cancer cells isolated from cisplatin-resistant tumors, ODYA signal was more evenly distributed in the cells imaged, while signal from glucose-$d_7$ was weaker. Quantitative analysis showed that the metabolic indices were higher in samples from four patients with resistant tumors, when compared to cancer cells from seven patients with sensitive disease (FIG. 3L). The histogram of metabolic index data indicated a clear separation between the sensitive and resistant groups (FIG. 3M). Receiver operating characteristic (ROC) analysis yielded a threshold value at 0.412 with high sensitivity of 1, specificity of 1 and AUC (area under curve) of 1, suggesting that the metabolic index has a high chance to successfully distinguish platinum sensitive and resistant ovarian cancer cells (FIG. 3N). This study shows clinical applicability of metabolic imaging for predicting response/resistance to platinum.

Example 4

Fatty Acid Uptake Contributes to Cisplatin Resistance

Knowing that cisplatin-resistant ovarian cancer cells uptake more fatty acid, whether the fatty acid uptake was a cause or result of cisplatin resistance was investigated. First, whether modulating exogenous fatty acid availability affect endogenous lipid amount in cisplatin-resistant ovarian cancer cells was tested. OVCAR5-cisR cells were cultured in lipid-deficient culture medium or normal medium supplemented with 1% lipid mixture for 24 hours and then examined lipid amount by SRS microscopy. Lipid-deficiency significantly reduced intra-cellular lipid amount while lipid supplementation increased the intra-cellular lipid amount (FIGS. 4A and 4B). Similar phenomenon was observed in the SKOV3-cisR cell line (FIGS. 4C and 4D). These observations are further support that fatty acid uptake, instead of de novo lipogenesis, was the major source of the lipid accumulation in cisplatin-resistant ovarian cancer cells.

Next, whether modulating exogenous lipid availability impacts cancer cell's resistance to cisplatin was examined. Lipid-deficiency increased sensitivity to cisplatin, while lipid supplementation slightly decreased sensitivity to cisplatin in OVCAR5-cisR (FIG. 4E), PEO4 (FIG. 4F), and SKOV3-cisR cells (FIG. 4G). To check whether ovarian cancer cells would upregulate glucose metabolism in a fatty acid depleted environment, glucose uptake was measured in SKOV3 and SKOV3-cisR cells cultured with regular or lipid-deficient medium using fluorescent glucose analog 2-NBDG. Glucose uptake remained similar in lipid sufficient and deficient environment (FIGS. 4H and 4I). Thus, resistance to cisplatin can be alleviated by modulating exogenous fatty acid availability.

Fatty acid uptake is a cellular process facilitated by multiple fatty acid transporters/carriers, including CD36, FATPs, and FABPs [42, 43]. One of the key proteins reported to be upregulated in ovarian cancer is the fatty acid binding protein 4 (FABP4) [12, 44]. Whether the increased fatty acid uptake in cisplatin-resistant ovarian cancer cells was regulated through upregulation of FABP4 was assessed, and showed very low FABP4 mRNA levels in OVCAR5 and OVCAR5-cisR cells, suggesting FABP4 likely does not play a major role in mediating the increased fatty acid uptake in cisplatin-resistant OVCAR5 cells. Next, the expression of a panel of other fatty acid uptake regulator genes was investigated, including CD36, FATP1-6, FABP5, and GOT2 (FABP(PM)) [45] and expression of FABP5 and FABP(PM) was found to be higher than other genes (FIG. 4J). Replication experiments confirmed a significant upregulation of FABP5 and FABP(PM) in resistant OVCAR5-cisR (FIGS. 4K-4L) and PEO4 cells (FIG. 4M) compared to their parental cells, suggesting that FABP5 and FABP(PM) may mediate fatty acid uptake in cisplatin-resistant cells. In addition, cisplatin treatment induced an acute rise of FABP5 and FABP(PM) expression in cisplatin sensitive cell OVCAR5 (FIG. 4N), further supporting the involvement of FABP5 and FABP(PM) in cisplatin resistance related fatty acid uptake. In contrast, mRNA expression levels of glucose transporter GLUT1 was reduced in resistant SKOV3-cisR compared to parental cells (FIG. 4O. GLUT1 expression was not significantly changed after cisplatin treatment in OVCAR5 cells, implying that GLUT1 downregulation may be an adaptive change in cisplatin-resistant cells rather than an acute response to cisplatin treatment (FIG. 4P). To rule out the possibility that the increased fatty acid uptake was caused by change in membrane fluidity at high concentrations of exogenous fatty acids, SRS imaging of fatty acid uptake was performed at lower concentrations of PA-d$^{31}$ and OA-d$^{34}$, which showed a similar trend of increased fatty acid uptake in resistant cells (FIGS. 4Q-4T). These data support that increased fatty update in cisplatin-resistant ovarian cancer cells is transporter mediated and likely due to an adaptive metabolic reprogramming in response to cisplatin treatment.

Next, whether a potent inhibitor of FABP, BMS309403 (BMS), can suppress fatty acid uptake in cisplatin-resistant cells was tested [46]. Treatment with BMS significantly reduced PA-d$_{33}$ uptake in OVCAR5-cisR cells (FIGS. 4U and 4V). Suppression of fatty acid uptake by BMS was also observed in SKOV3-cisR cells in a dose dependent manner (FIGS. 4W and 4X). Furthermore, inhibition of fatty acid uptake by BMS reduced resistance to cisplatin in multiple resistant cell lines, including PEO4 (FIG. 4Y), SKOV3-cisR (FIG. 4Z), and OVCAR5-cisR cells (FIG. 4AA), while the effects of BMS were less obvious in the sensitive cell lines (FIGS. 4BB-4DD). These results support deregulated fatty acid uptake in the development of cisplatin resistance in OC cells.

Example 5

Increased Fatty Acid Oxidation Rate Contributes to Cisplatin Resistance

Considering that one major function of lipids is energy production through fatty acid oxidation, whether fatty acid oxidation was increased in cisplatin resistant cancer cells was investigated. By measuring the OCR in parental and resistant cancer cells, OVCAR5-cisR cells displayed much higher levels of oxygen consumption than OVCAR5 cells (FIG. 5A). Etomoxir, an inhibitor of CPT1 that transports fatty acid into mitochondria for fatty acid oxidation, was used to test whether the increased oxidation rate arises from fatty acid oxidation. Etomoxir did not induce an obvious change in oxygen consumption in OVCAR5 cells (FIG. 5B), but significantly reduced oxygen consumption in OVCAR5-cisR cells (FIG. 5C). Quantitation of OCR confirmed a significant reduction of OCR after etomoxir treatment in OVCAR5-cisR cells, but not in OVCAR5 cells (FIG. 5D). Fatty acid oxidation was also measured through the Seahorse® FAO assay to assess etomoxir-induced mitochondrial respiration change. As shown in FIG. 5E, OVCAR5-cisR cells had an overall higher OCR than the parental cells and showed an obvious reduction of OCR after treatment with etomoxir. In contrast, OCR of OVCAR5 cells was less sensitive to etomoxir treatment. Etomoxir-induced basal respiration, ATP production, and maximal respiration reduction in resistant OVCAR5-cisR cells were significantly higher than those in sensitive OVCAR5 cells, suggesting significantly upregulated fatty acid oxidation in resistant cells (FIG. 5F). Further, Seahorse® measurement of OCR in PEO1 and PEO4 cells supports a significant increase of fatty acid oxidation rate in PEO4 cells compared to PEO1 cells (FIG. 5G). These data indicate that FAO significantly increases in cisplatin-resistant cells.

To test whether the increased fatty acid oxidation contributes to cisplatin resistance, the response to etomoxir in cisplatin-resistant cells and parental cells was investigated. Higher sensitivity to etomoxir treatment in cisplatin-resistant cell lines was observed when compared to their parental cell lines, in paired cell lines including PEO1 and PEO4 (FIG. 5H), OVCAR5 and OVCAR5-cisR (FIG. 5I), and COV362 and COV362-cisR (FIG. 5J), indicating higher dependence on fatty acid oxidation in cisplatin-resistant cells. Next, whether etomoxir treatment could reduce resistance to cisplatin was tested. The dose-response to cisplatin curves were significantly left shifted with etomoxir treatment in PEO4 (FIG. 5K), OVCA5-cisR (FIG. 5L), and COV362-cisR cells (FIG. 5M), and support the potential of etomoxir to re-sensitize resistant ovarian cancer cells to cisplatin. The observation was further confirmed by shRNA-mediated knockdown of CPT1a in OVCAR5-cisR cells (FIGS. 5N and 5O). Knockdown of CPT1a in OVCAR5-cisR cells increased its sensitivity to cisplatin treatment compared to the control group (FIG. 5P). Interestingly, the CPT1a mRNA and protein levels were similar in OVCAR5 and OVCAR5-cisR cells (FIGS. 5Q and 5R), indicating that enhanced fatty acid oxidation in cisplatin-resistant ovarian cancer is likely the result of increased activation (not upregulation) of CPT1a.

To determine whether the functional changes were caused by transcriptional reprogramming, RNA sequencing compared resistant and parental OVCAR5 and SKOV3 cells. Heatmaps show hierarchical clustering of genes related to FA metabolism and illustrate distinct separation between sensitive/resistant cells (FIGS. 5S and 5T). In both cell lines, several FAO related genes including CRAT, PPARA, ACOT8, HSD17B10, ACADVL, ACOX1 and DECR1 were upregulated in resistant cells, while FA synthesis related genes such as MEI, NSDHL, DHCR24, FASN, ELOVL5, ALDH3A2, ACSL4 and SERINC1 were downregulated (FIGS. 5S and 5T).

These transcriptomic findings show increased fatty acid oxidation activity and reduced de novo fatty acid synthesis in cisplatin-resistant ovarian cancer.

A patient-derived xenograft (PDX) model rendered platinum resistant through repeated exposure to carboplatin in vivo as described previously [40] was used to test whether interruption of fatty acid oxidation could sensitize ovarian tumors to platinum in vivo. To avoid toxicity induced by cisplatin, cisplatin was substituted with carboplatin, a second-generation agent. Carboplatin or etomoxir single-agent treatment induced a slight reduction of tumor growth, whereas the combination treatment caused a significant suppression of tumor growth (FIG. 5U). Body weights remained stable in all groups, suggesting that the combination treatment was tolerable (FIG. 5V). These data collectively support development of a combination of platinum with a fatty acid oxidation inhibitor for platinum-resistant cancer treatment.

Example 6

FAO Facilitates Cancer Cell Survival Under Cisplatin-Induced Oxidative Stress

Cisplatin has been known to cause cytotoxicity by inducing oxidative stress, in addition to DNA adduct formation [47-49]. Excess oxidative stress can inhibit glycolysis by inactivating key glycolytic enzymes, such as pyruvate kinase M2 (PKM2) and glyceraldehyde 3-phosphate dehydrogenase (GAPDH) [15, 50]. Increased reactive oxidative species (ROS) oxidizes intracellular NADPH and thus suppresses de novo lipogenesis, as NADPH is one of the precursors for lipogenesis [51]. Therefore, fatty acid uptake and oxidation may promote cancer cell survival under cisplatin-induced oxidative stress by replenishing free fatty acid and ATP, deficiency of which is caused by decreased de novo lipogenesis and glycolysis under oxidative stress. As a test, the oxidative stress level was examined by measuring intracellular ROS using a fluorescent probe, 2',7'-dichlorodihydrofluorescein diacetate (H2DCFDA). Using confocal microscopy, OVCAR5-cisR cells showed much stronger fluorescent signal than OVCAR5 cells (FIGS. 6A-6B). Similar trend of increased ROS in PEO4 cells compared to PEO1 cells was also observed (FIGS. 6C-6D). Furthermore, the change in ROS in OVCAR5 and OVCAR5-cisR cells treated with cisplatin was analyzed and showed that cisplatin treatment induced significant increase of ROS production in both cell lines (FIG. 6E).

Next, whether the reduced form of intracellular NADPH is depleted in cisplatin-resistant cells was examined. NADPH/NADP$^+$ ratios were significantly lower in cisplatin-resistant PEO4 (FIG. 6F) and OVCAR5-cisR cells (FIG. 6G), when compared to PEO1 and OVCAR5 cells, respectively. The reduced NADPH level corroborate the SRS images showing decreased de novo lipogenesis in cisplatin-resistant cells. Changes in glycolysis were analyzed by measuring ECAR by Seahorse®. Cisplatin treatment promptly lowered the ECAR rate in both PEO1 and PEO4 cells (FIG. 6H), reaching significant reduction within ~30 min of treatment (FIG. 6I). On the contrary, cisplatin treatment also induced slight increase of OCR in PEO1 and PEO4 cells (FIGS. 6J and 6K). In agreement with the observed decreased glycolysis, glucose uptake, measured by 2-NBDG under a confocal microscope, was reduced in cisplatin-treated OVCAR5 cells (FIGS. 6L and 6M). Further, OVCAR5-cisR cells took up much less 2-NBDG than OVCAR5 cells (FIGS. 6L and 6M), implying a decreased reliance on glucose metabolism in cisplatin-resistant OC cells.

With glycolysis suppressed by increased oxidative stress, it appeared that ATP production would be impaired in cisplatin-resistant cells or cisplatin treated cells. The cellular ATP/ADP level was measured and showed the ratio of ATP/ADP was significantly lower in both PEO4 (FIG. 6N) and OVCAR5-cisR cells (FIG. 6O), when compared to PEO1 and OVCAR5 cells, respectively. Furthermore, acute treatment with cisplatin reduced ATP/ADP ratio in OVCAR5 cells, but not in OVCAR5-cisR cells. Supplementation with palmitic acid significantly increased the ATP level in OVCAR5-cisR cells, but not in OVCAR5 cells (FIG. 6P). Collectively, these data suggest that cisplatin-resistant OC cells undergo metabolic reprogramming from glucose-dependent to fatty acid-dependent metabolism. This could be related to the propensity of ovarian tumors to grow and disseminate in an adipocyte-rich microenvironment. Adipocytes have been reported to provide fatty acids as energy source for ovarian cancer cells [12] and undergo increased lipolysis in response to cisplatin treatment [52]. FIG. 6Q shows glycolysis and lipogenesis are inhibited by cisplatin-induced oxidative stress, limiting the production of energy as well as the synthesis of free fatty acids. To survive and proliferate under cisplatin-induced oxidative stress, cancer cells upregulate fatty acid uptake and oxidation as an alternative route of energy production.

Example 7

Cisplatin Treatment Induces a Transient Metabolic Shift Toward Increased Fatty Acid Uptake in Multiple Types of Cancers Understanding that increased FA uptake in cisplatin-resistant ovarian cancer cells is likely a stable metabolic adaptation to cisplatin induced oxidative stress, whether the same metabolic shift occurs in other types of cancers upon cisplatin treatment was examined. Platinum is widely used across malignancies. Therefore, a few representative cancer cell lines were selected, including MIA PaCa-2 pancreatic cancer, A549 lung cancer, and MD-MBA231 breast cancer, to test whether acute cisplatin treatment changes the rate of fatty acid uptake. The $IC_{50}$ to cisplatin in these three cell lines was determined, and 6.6 µM was selected as the final treatment concentration, at which dose no significant cell death was induced (FIGS. 7A-7C). Results show that treatment with 6.6 µM cisplatin significantly increased uptake of PA-$d_{31}$ and OA-$d_{34}$ in MIA PaCa-2 cells (FIGS. 7D and 7E). The fold increase in PA uptake was more significant than OA (FIG. 7F), suggesting PA might be a preferred source of FA for cells under cisplatin induced oxidative stress. Similarly, we observed that treatment with cisplatin also induced a significant increase in PA-d31 and OA-d34 uptake in A549 (FIGS. 7G, 7H, and 7I) and MD-MBA231 cells (FIGS. 7J, 7K, and 7L). These findings are broadly applicable to multiple types of cisplatin-resistant cancers. FIG. 8 illustrates the cellular metabolism switch from glycolysis to fatty acid oxidation with decreased glucose uptake, glycolysis and de novo lipogenesis while fatty acid uptake and oxidation are increased. This shows a central metabolic alteration or change in anabolic and energetic metabolism in resistant cells. Inhibition of FAO re-sensitizes cisplatin-resistant OC cells to cisplatin treatment both in vitro and in vivo, paving the foundation towards a new combinational therapy of FAO inhibitors and cancer therapies such as chemotherapy platinum drugs.

REFERENCES

All references and publications cited in this disclosure specification with the examples and drawings are incorporated by reference herein in their entireties, including:
1. Koppenol, W. H., Bounds, P. L. and Dang, C. V., Otto Warburg's contributions to current concepts of cancer metabolism. *Nat Rev Cancer,* 11, 325-337 (2011).
2. Ward, Patrick S. and Thompson, Craig B., Metabolic Reprogramming: A Cancer Hallmark Even Warburg Did Not Anticipate. *Cancer Cell,* 21, 297-308 (2012).
3. Martinez-Outschoorn, U. E., Peiris-Pages, M., Pestell, R. G., Sotgia, F. and Lisanti, M. P., Cancer metabolism: a therapeutic perspective. *Nat. Rev. Clin. Oncol.,* 14, 11-31 (2017).
4. Kim, J. and DeBerardinis, R. J., Mechanisms and Implications of Metabolic Heterogeneity in Cancer. *Cell Metab.,* 30, 434-446 (2019).
5. Faubert, B., Solmonson, A. and DeBerardinis, R. J., Metabolic reprogramming and cancer progression. *Science,* 368, eaaw5473 (2020).
6. Pascual, G. et al., Targeting metastasis-initiating cells through the fatty acid receptor CD36. *Nature,* 541, 41-45 (2017).
7. Bergers, G. and Fendt, S. M., The metabolism of cancer cells during metastasis. *Nat Rev Cancer,* 21, 162-180 (2021).
8. Li, J. et al. Lipid desaturation Is a metabolic marker and therapeutic target of ovarian cancer stem cells. *Cell Stem Cell,* 20, 303-314 e305 (2017).
9. Chae, Y. C. and Kim, J. H. Cancer stem cell metabolism: target for cancer therapy. *BMB Reports,* 51, 319-326 (2018).
10. Sousa, C. M. et al. Pancreatic stellate cells support tumour metabolism through autophagic alanine secretion. *Nature,* 536, 479-483 (2016).
11. Miranda, F. et al. Salt-Inducible Kinase 2 Couples Ovarian Cancer Cell Metabolism with Survival at the Adipocyte-Rich Metastatic Niche. *Cancer Cell,* 30, 273-289 (2016).
12. Nieman, K. M. et al. Adipocytes promote ovarian cancer metastasis and provide energy for rapid tumor growth. *Nature Medicine,* 17, 1498-1503 (2011).
13. Schug, Zachary T. et al. Acetyl-CoA Synthetase 2 Promotes Acetate Utilization and Maintains Cancer Cell Growth under Metabolic Stress. *Cancer Cell,* 27, 57-71 (2015).
14. Peck, B. et al. Inhibition of fatty acid desaturation is detrimental to cancer cell survival in metabolically compromised environments. *Cancer Metab,* 4, 016-0146 (2016).
15. Mullarky, E. and Cantley, L. C. in Innovative Medicine. (eds. K. Nakao, N. Minato and S. Uemoto) 3-23 (Springer Japan, Tokyo; 2015).
16. Holohan, C., Van Schaeybroeck, S., Longley, D. B. and Johnston, P. G. Cancer drug resistance: an evolving paradigm. *Nat Rev Cancer,* 13, 714-726 (2013).
17. Zhao, Y., Butler, E. B. and Tan, M. Targeting cellular metabolism to improve cancer therapeutics. *Cell Death Dis,* 4, e532 (2013).
18. Rahman, M. and Hasan, M. Cancer Metabolism and Drug Resistance. *Metabolites,* 5, 571 (2015).
19. Lin, J. et al. The roles of glucose metabolic reprogramming in chemo- and radio-resistance. *J. Exp. Clin. Cancer Res.,* 38, 019-1214 (2019).
20. Wagner, W., Ciszewski, W. M. and Kania, K. D. L- and D-lactate enhance DNA repair and modulate the resistance of cervical carcinoma cells to anticancer drugs via histone deacetylase inhibition and hydroxycarboxylic acid receptor 1 activation. *Cell Commun Signal,* 13, 015-0114 (2015).
21. Cao, Y. Adipocyte and lipid metabolism in cancer drug resistance. *J. Clin. Invest.,* 129, 3006-3017 (2019).
22. Tadros, S. et al. De Novo Lipid Synthesis Facilitates Gemcitabine Resistance through Endoplasmic Reticulum Stress in Pancreatic Cancer. *Cancer Res.,* 77, 5503 (2017).
23. Iwamoto, H. et al. Cancer Lipid Metabolism Confers Antiangiogenic Drug Resistance. *Cell Metab.,* 28, 104-117.e105 (2018).
24. Cotte, A. K. et al. Lysophosphatidylcholine acyltransferase 2-mediated lipid droplet production supports colorectal cancer chemoresistance. *Nature Communications,* 9, 322 (2018).
25. Rehman, S. K. et al. Colorectal Cancer Cells Enter a Diapause-like DTP State to Survive Chemotherapy. *Cell,* 184, 226-242 e221 (2021).
26. Rottenberg, S., Disler, C. and Perego, P. The rediscovery of platinum-based cancer therapy. *Nat Rev Cancer,* 21, 37-50 (2021).
27. Wang, D. and Lippard, S. J. Cellular processing of platinum anticancer drugs. *Nat. Rev. Drug Discov.,* 4, 307-320 (2005).
28. Cheng, J. X. and Xie, X. S. Vibrational spectroscopic imaging of living systems: An emerging platform for biology and medicine. *Science,* 350, aaa8870 (2015).
29. Hu, F., Shi, L. and Min, W. Biological imaging of chemical bonds by stimulated Raman scattering microscopy. *Nat Methods,* 16, 830-842 (2019).
30. Liao, C. S. and Cheng, J. X. In situ and in vivo molecular analysis by coherent Raman scattering microscopy. *Annu. Rev. Anal. Chem.,* 9, 69-93 (2016).
31. Zhang, C., Zhang, D. and Cheng, J. X. Coherent Raman scattering microscopy in biology and medicine. *Annu. Rev. Biomed. Eng.,* 17, 415-445 (2015).
32. Yue, S. et al. Cholesteryl ester accumulation induced by PTEN loss and PI3K/AKT activation underlies human prostate cancer aggressiveness. *Cell Metabolism,* 19, 393-406 (2014).
33. Li, J. et al. Abrogating cholesterol esterification suppresses growth and metastasis of pancreatic cancer. *Oncogene,* 35, 6378-6388 (2016).
34. Zhang, L. et al. Spectral tracing of deuterium for imaging glucose metabolism. *Nat. Biomed. Eng.,* 3, 402-413 (2019).
35. Li, J. and Cheng, J. X. Direct visualization of de novo lipogenesis in single living cells. *Sci. Rep.,* 4, 6807 (2014).
36. Long, R. et al. Two-color vibrational imaging of glucose metabolism using stimulated Raman scattering. *Chem Commun (Camb),* 54, 152-155 (2018).
37. Huang, K. C., Li, J., Zhang, C., Tan, Y. and Cheng, J. X. Multiplex stimulated raman scattering Imaging cytometry reveals lipid-rich protrusions in cancer cells under stress condition. *iScience,* 23, 100953 (2020).

38. Du, J. et al. Raman-guided subcellular pharmaco-metabolomics for metastatic melanoma cells. *Nat. Commun.*, 11, 4830 (2020).
39. Fu, D. and Xie, X. S. Reliable cell segmentation based on spectral phasor analysis of hyperspectral stimulated Raman scattering imaging data. *Anal Chem*, 86, 4115-4119 (2014).
40. Wang, Y. et al. Frizzled-7 identifies platinum-tolerant ovarian cancer cells susceptible to ferroptosis. *Cancer Res.*, 81, 384-399 (2021).
41. Langdon, S. P. et al. Characterization and properties of nine human ovarian adenocarcinoma cell lines. *Cancer Res.*, 48, 6166-6172 (1988).
42. McArthur, M. J. et al. Cellular uptake and intracellular trafficking of long chain fatty acids. *Journal of Lipid Research*, 40, 1371-1383 (1999).
43. Su, X. and Abumrad, N. A. Cellular fatty acid uptake: a pathway under construction. *Trends Endocrinol. Metab.*, 20, 72-77 (2009).
44. Mukherjee, A. et al. Adipocyte-Induced FABP4 Expression in Ovarian Cancer Cells Promotes Metastasis and Mediates Carboplatin Resistance. *Cancer Res*, 80, 1748-1761 (2020).
45. Doege, H. and Stahl, A. Protein-mediated fatty acid uptake: novel insights from in vivo models. *Physiology (Bethesda)*, 21, 259-268 (2006).
46. Furuhashi, M. et al. Treatment of diabetes and atherosclerosis by inhibiting fatty-acid-binding protein aP2. *Nature*, 447, 959-965 (2007).
47. Belotte, J. et al. The role of oxidative stress in the development of cisplatin resistance in epithelial ovarian cancer. *Reprod. Sci.*, 21, 503-508 (2014).
48. Johnson, S. W. et al. Relationship between platinum-DNA adduct formation and removal and cisplatin cytotoxicity in cisplatin-sensitive and -resistant human ovarian cancer cells. *Cancer Res.*, 54, 5911-5916 (1994).
49. van de Vaart, P. J. et al. Intraperitoneal cisplatin with regional hyperthermia in advanced ovarian cancer: pharmacokinetics and cisplatin-DNA adduct formation in patients and ovarian cancer cell lines. *Eur. J. Cancer*, 34, 148-154 (1998).
50. Ghanbari Movahed, Z., Rastegari-Pouyani, M., Mohammadi, M. H. and Mansouri, K. Cancer cells change their glucose metabolism to overcome increased ROS: One step from cancer cell to cancer stem cell? *Biomed. Pharmacother.*, 112, 108690 (2019).
51. Currie, E., Schulze, A., Zechner, R., Walther, T. C. and Farese, R. V., Jr. Cellular fatty acid metabolism and cancer. *Cell Metab*, 18, 153-161 (2013).
52. Eckert, M. A., Orozco, C., Xiao, J., Javellana, M. and Lengyel, E. The Effects of Chemotherapeutics on the Ovarian Cancer Microenvironment. *Cancers (Basel)*, 13 (2021).
53. Wang, D. and Lippard, S. J. Cellular processing of platinum anticancer drugs. *Nat Rev Drug Discov*, 4, 307-320 (2005).
54. Galluzzi, L. et al. Molecular mechanisms of cisplatin resistance. *Oncogene*, 31, 1869-1883 (2012).
55. Shen, D. W., Pouliot, L. M., Hall, M. D. and Gottesman, M. M. Cisplatin resistance: a cellular self-defense mechanism resulting from multiple epigenetic and genetic changes. *Pharmacol Rev* 64, 706-721 (2012).
56. Itoh, T. et al. Cisplatin induces production of reactive oxygen species via NADPH oxidase activation in human prostate cancer cells. *Free Radical Research*, 45, 1033-1039 (2011).
57. Marullo, R. et al. Cisplatin induces a mitochondrial-ROS response that contributes to cytotoxicity depending on mitochondrial redox status and bioenergetic functions. *PLoS One*, 8, e81162 (2013).
58. Yu, W. et al. Cisplatin generates oxidative stress which is accompanied by rapid shifts in central carbon metabolism. *Sci. Rep.*, 8, 4306 (2018).
59. Zaugg, K. et al. Carnitine palmitoyltransferase 1C promotes cell survival and tumor growth under conditions of metabolic stress. *Genes & Development*, 25, 1041-1051 (2011).
60. Ma, Y. et al. Fatty acid oxidation: An emerging facet of metabolic transformation in cancer. *Cancer Lett.*, 435, 92-100 (2018).
61. Melone, M. A. B. et al. The carnitine system and cancer metabolic plasticity. *Cell Death Dis.*, 9, 228 (2018).
62. van der Vusse, G. J., van Bilsen, M., Glatz, J. F., Hasselbaink, D. M. and Luiken, J. J. Critical steps in cellular fatty acid uptake and utilization. *Molecular and Cellular Biochemistry*, 239, 9-15 (2002).
63. Koundouros, N. and Poulogiannis, G. Reprogramming of fatty acid metabolism in cancer. *Br J Cancer*, 122, 4-22 (2020).
64. Snaebjornsson, M. T., Janaki-Raman, S. and Schulze, A. Greasing the Wheels of the Cancer Machine: The Role of Lipid Metabolism in Cancer. *Cell Metab*, 31, 62-76 (2020).
65. Condello, S. et al. [beta]-Catenin-regulated ALDH1A1 is a target in ovarian cancer spheroids. *Oncogene*, 34, 2297-2308 (2015).
66. Condello, S. et al. Tissue tranglutaminase regulates interactions between ovarian cancer stem cells and the tumor niche. *Cancer Res.*, 78, 2990-3001 (2018).
67. Dong, R. et al. Histologic and molecular analysis of patient derived xenografts of high-grade serous ovarian carcinoma. *J. Hematol. Oncol.*, 9, 92 (2016).
68. Carpenter, A. E. et al. CellProfiler: image analysis software for identifying and quantifying cell phenotypes. *Genome Biology*, 7, R100 (2006).
69. Robinson, M. D., McCarthy, D. J. and Smyth, G. K. edgeR: a Bioconductor package for differential expression analysis of digital gene expression data. *Bioinformatics*, 26, 139-140 (2010).

We claim:

1. An assay for determining resistance in a target cell to a therapy, the assay comprising:
   measuring glucose and glycolysis derived anabolism in the target cell;
   measuring fatty acid uptake and oxidation in the target cell; and
   determining a change from glucose anabolism in the target cell to fatty acid uptake and oxidation energy metabolism.

2. The assay of claim 1, wherein chemical microscopy is used to measure glucose and glycolysis derived anabolism and fatty acid uptake and oxidation.

3. The assay of claim 2, wherein the chemical microscopy is Raman scattering microscopy or infrared microscopy.

4. The assay of claim 3, wherein the Raman scattering microscopy is selected from the group consisting of: spontaneous Raman scattering microscopy, surface enhanced Raman scattering microscopy, coherent anti-stokes Raman scattering (CARS), stimulated Raman scattering (SRS) microscopy, and hyperspectral stimulated Raman scattering imaging.

5. The assay of claim 3, wherein the infrared microscopy is selected from the group consisting of: mid-infrared photothermal (MIP) microscopy, direct infrared absorption based microscopy, fourier-transformed infrared (FTIR) microscopy, and quantum cascade laser (QCL) microscopy.

6. The assay of claim 1, further comprising measuring de novo lipogenesis in the target cell and determining a change from glucose and glycolysis dependent anabolism and de novo lipogenesis in the target cell to fatty acid uptake and oxidation energy metabolism.

7. The assay of claim 1, wherein the therapy induces cellular stress in the target cell.

8. The assay of claim 7, wherein the cellular stress is oxidative stress, metabolic stress, hypoxic stress, nutrient stress, thermal stress, genotoxic stress, or combinations thereof.

9. The assay of claim 1, wherein the therapy is a cancer therapy.

10. The assay of claim 9, wherein the cancer therapy is selected from chemotherapy, radiotherapy, immunotherapy, targeted therapy, hormone therapy, light therapy, laser therapy, photodynamic therapy, and combinations thereof.

11. The assay of claim 9, wherein the cancer therapy is chemotherapy comprising one or more platinum-based agents, nitrosoureas, anti-metabolites, anti-tumor antibiotics, plant alkaloids, topoisomerase inhibitors, mitotic inhibitors, hormonal agents, corticosteroids, biological response modifiers, carboplatin, and/or oxaliplatin.

12. The assay of claim 9, wherein the cancer therapy is configured to treat one or more of ovarian, prostate, testicular, bladder, head, neck, pancreatic, lung, breast, and esophageal cancer.

13. A method of treating a subject to inhibit resistance to a cancer therapy, the method comprising:
   obtaining a cancer cell from the subject;
   performing the assay of claim 1 on the cancer cell; and
   administering the cancer therapy to the subject.

14. The method of claim 13, wherein the cancer therapy is selected from chemotherapy, radiotherapy, immunotherapy, targeted therapy, hormone therapy, light therapy, laser therapy, photodynamic therapy, and combinations thereof.

15. The method of claim 14, wherein the cancer therapy is chemotherapy comprising one or more platinum-based agents, nitrosoureas, anti-metabolites, anti-tumor antibiotics, plant alkaloids, topoisomerase inhibitors, mitotic inhibitors, hormonal agents, corticosteroids, biological response modifiers, carboplatin, and/or oxaliplatin.

16. The method of claim 13, wherein the cancer cell is selected from ovarian, prostate, testicular, bladder, pancreatic, lung, breast, esophageal, head, and neck cancer.

17. The method of claim 13, further comprising administering at least one inhibitor of fatty acid oxidation to the subject.

18. The method of claim 17, wherein the at least one inhibitor of fatty acid oxidation is selected from etomoxir, oxfenicine, perhexiline, mildronate, trimetazidine, and combinations thereof.

19. The method of claim 13, wherein the subject is a mammal.

20. The method of claim 19, wherein the subject is a human.

* * * * *

SEQUENCE LISTING

```
Sequence total quantity: 24
SEQ ID NO: 1              moltype = DNA  length = 21
FEATURE                   Location/Qualifiers
misc_feature              1..21
                          note = Primer Sequence
source                    1..21
                          mol_type = other DNA
                          organism = synthetic construct
SEQUENCE: 1
```

```
tccagttggc ttatcgtggt g                                              21

SEQ ID NO: 2           moltype = DNA   length = 23
FEATURE                Location/Qualifiers
misc_feature           1..23
                       note = Primer Sequence
source                 1..23
                       mol_type = other DNA
                       organism = synthetic construct
SEQUENCE: 2
tccagagtcc gattgatttt tgc                                            23

SEQ ID NO: 3           moltype = DNA   length = 21
FEATURE                Location/Qualifiers
misc_feature           1..21
                       note = Primer Sequence
source                 1..21
                       mol_type = other DNA
                       organism = synthetic construct
SEQUENCE: 3
tgaaggagct aggagtggga a                                              21

SEQ ID NO: 4           moltype = DNA   length = 22
FEATURE                Location/Qualifiers
misc_feature           1..22
                       note = Primer Sequence
source                 1..22
                       mol_type = other DNA
                       organism = synthetic construct
SEQUENCE: 4
tgcaccatct gtaaagttgc ag                                             22

SEQ ID NO: 5           moltype = DNA   length = 21
FEATURE                Location/Qualifiers
misc_feature           1..21
                       note = Primer Sequence
source                 1..21
                       mol_type = other DNA
                       organism = synthetic construct
SEQUENCE: 5
ggaaggaaat agcaacagtg g                                              21

SEQ ID NO: 6           moltype = DNA   length = 23
FEATURE                Location/Qualifiers
misc_feature           1..23
                       note = Primer Sequence
source                 1..23
                       mol_type = other DNA
                       organism = synthetic construct
SEQUENCE: 6
tcctacacgc tcaccatata agc                                            23

SEQ ID NO: 7           moltype = DNA   length = 21
FEATURE                Location/Qualifiers
misc_feature           1..21
                       note = Primer Sequence
source                 1..21
                       mol_type = other DNA
                       organism = synthetic construct
SEQUENCE: 7
cttcgatggc tatgtcagcg a                                              21

SEQ ID NO: 8           moltype = DNA   length = 21
FEATURE                Location/Qualifiers
misc_feature           1..21
                       note = Primer Sequence
source                 1..21
                       mol_type = other DNA
                       organism = synthetic construct
SEQUENCE: 8
agcacgtcac ctgagaggta g                                              21

SEQ ID NO: 9           moltype = DNA   length = 20
FEATURE                Location/Qualifiers
misc_feature           1..20
                       note = Primer Sequence
source                 1..20
                       mol_type = other DNA
                       organism = synthetic construct
```

```
SEQUENCE: 9
atgcgagaaa agttggtgct                                                      20

SEQ ID NO: 10           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 10
tttcatcacg gacaggttca                                                      20

SEQ ID NO: 11           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 11
atacctggga gcgttttgtg                                                      20

SEQ ID NO: 12           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 12
ccgctgtcct gtgtagttga                                                      20

SEQ ID NO: 13           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 13
cttttccagc cgcttccaca                                                      20

SEQ ID NO: 14           moltype = DNA  length = 18
FEATURE                 Location/Qualifiers
misc_feature            1..18
                        note = Primer Sequence
source                  1..18
                        mol_type = other DNA
                        organism = synthetic construct
SEQUENCE: 14
tggctggcag ggaatgca                                                        18

SEQ ID NO: 15           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 15
agctcctgcg gtacttgtgt                                                      20

SEQ ID NO: 16           moltype = DNA  length = 20
FEATURE                 Location/Qualifiers
misc_feature            1..20
                        note = Primer Sequence
source                  1..20
                        mol_type = other DNA
                        organism = synthetic construct
SEQUENCE: 16
aaggtctccc acacatcagc                                                      20

SEQ ID NO: 17           moltype = DNA  length = 21
FEATURE                 Location/Qualifiers
misc_feature            1..21
                        note = Primer Sequence
source                  1..21
                        mol_type = other DNA
```

```
                                organism = synthetic construct
SEQUENCE: 17
gctgggcctt ataagcacac a                                                    21

SEQ ID NO: 18              moltype = DNA   length = 20
FEATURE                    Location/Qualifiers
misc_feature               1..20
                           note = Primer Sequence
source                     1..20
                           mol_type = other DNA
                           organism = synthetic construct
SEQUENCE: 18
caacctcagt ggttgcgaca                                                      20

SEQ ID NO: 19              moltype = DNA   length = 19
FEATURE                    Location/Qualifiers
misc_feature               1..19
                           note = Primer Sequence
source                     1..19
                           mol_type = other DNA
                           organism = synthetic construct
SEQUENCE: 19
ggctgtgacc ggaactgtg                                                       19

SEQ ID NO: 20              moltype = DNA   length = 22
FEATURE                    Location/Qualifiers
misc_feature               1..22
                           note = Primer Sequence
source                     1..22
                           mol_type = other DNA
                           organism = synthetic construct
SEQUENCE: 20
aggtctccaa ctggcattag aa                                                   22

SEQ ID NO: 21              moltype = DNA   length = 20
FEATURE                    Location/Qualifiers
misc_feature               1..20
                           note = Primer Sequence
source                     1..20
                           mol_type = other DNA
                           organism = synthetic construct
SEQUENCE: 21
actgggccag gaatttgacg                                                      20

SEQ ID NO: 22              moltype = DNA   length = 19
FEATURE                    Location/Qualifiers
misc_feature               1..19
                           note = Primer Sequence
source                     1..19
                           mol_type = other DNA
                           organism = synthetic construct
SEQUENCE: 22
ctcgtggaag tgacgccctt                                                      19

SEQ ID NO: 23              moltype = DNA   length = 21
FEATURE                    Location/Qualifiers
misc_feature               1..21
                           note = Primer Sequence
source                     1..21
                           mol_type = other DNA
                           organism = synthetic construct
SEQUENCE: 23
cccaccgtgt tcttcgacat t                                                    21

SEQ ID NO: 24              moltype = DNA   length = 22
FEATURE                    Location/Qualifiers
misc_feature               1..22
                           note = Primer Sequence
source                     1..22
                           mol_type = other DNA
                           organism = synthetic construct
SEQUENCE: 24
ggacccgtat gctttaggat ga                                                   22
```